(12) United States Patent
DeAngelis et al.

(10) Patent No.: US 7,229,796 B2
(45) Date of Patent: Jun. 12, 2007

(54) **HYALURONAN SYNTHASE GENES AND EXPRESSION THEREOF IN *BACILLUS* HOSTS**

(76) Inventors: Paul L. DeAngelis, 706 Sunnybrook Dr., Edmond, OK (US) 73034; Paul H. Weigel, 817 Hollowdale, Edmond, OK (US) 73003; Kshama Kumari, 16220 Sugar Loaf Dr., Edmond, OK (US) 73013

( * ) Notice: Subject to any disclaimer, the term of this patent is extended or adjusted under 35 U.S.C. 154(b) by 0 days.

(21) Appl. No.: 11/474,663

(22) Filed: Jun. 26, 2006

(65) Prior Publication Data

US 2006/0263858 A1    Nov. 23, 2006

Related U.S. Application Data

(60) Continuation of application No. 10/981,632, filed on Nov. 5, 2004, now Pat. No. 7,091,008, which is a division of application No. 10/172,527, filed on Jun. 13, 2002, now Pat. No. 6,951,743, which is a continuation-in-part of application No. 09/469,200, filed on Dec. 21, 1999, now Pat. No. 6,833,264, which is a continuation of application No. 09/178,851, filed on Oct. 26, 1998, now abandoned, said application No. 10/172,527 is a continuation-in-part of application No. 09/146,893, filed on Sep. 3, 1998, now Pat. No. 6,455,304, which is a continuation of application No. 08/270,581, filed on Jul. 1, 1994, now abandoned.

(60) Provisional application No. 60/305,285, filed on Jul. 13, 2001, provisional application No. 60/297,788, filed on Jun. 13, 2001, provisional application No. 60/297,744, filed on Jun. 13, 2001, provisional application No. 60/064,435, filed on Oct. 31, 1997.

(51) Int. Cl.
C12P 19/52    (2006.01)
C12P 19/04    (2006.01)

(52) U.S. Cl. .................... 435/84; 435/101; 435/252.31
(58) Field of Classification Search ..................... None
See application file for complete search history.

(56) References Cited

U.S. PATENT DOCUMENTS

| | | |
|---|---|---|
| 4,224,179 A | 9/1980 | Schneider |
| 4,235,871 A | 11/1980 | Papahadjopoulos et al. |
| 4,511,478 A | 4/1985 | Nowinski et al. |
| 4,517,295 A | 5/1985 | Bracke et al. |
| 4,708,861 A | 11/1987 | Popescu et al. |
| 4,780,414 A | 10/1988 | Nimrod et al. |
| 4,782,046 A | 11/1988 | Brown et al. |
| 4,784,990 A | 11/1988 | Nimrod et al. |
| 4,801,539 A | 1/1989 | Akasaka et al. |
| 5,015,577 A | 5/1991 | Weigel et al. |
| 5,023,175 A | 6/1991 | Hosoya et al. |
| 5,071,751 A | 12/1991 | Morita et al. |
| RE37,336 E | 8/2001 | Weigel et al. |
| 6,423,514 B1 | 7/2002 | Briskin |
| 6,455,304 B1 | 9/2002 | Weigel et al. |
| 6,492,150 B1 | 12/2002 | McDonald et al. |

FOREIGN PATENT DOCUMENTS

| | | |
|---|---|---|
| EP | 0195303 | 11/1989 |
| EP | 0144019 | 6/1990 |
| EP | 0266578 | 7/1993 |
| EP | 0244757 | 11/1994 |
| EP | 0036776 | 5/1998 |
| GB | 2249315 | 5/1992 |
| JP | 62032893 | 2/1987 |
| JP | 63094988 | 4/1988 |
| JP | 4-80202 | 3/1992 |
| JP | 4-158796 | 6/1992 |
| WO | WO 91/03559 | 3/1991 |
| WO | WO 94/00463 | 1/1994 |
| WO | WO 95/24497 | 9/1995 |
| WO | WO 95/33067 | 12/1995 |
| WO | WO 97/20061 | 6/1997 |

OTHER PUBLICATIONS

"The Combinations of Haemoglobin with Oxygen and with Carbon Monoxide.", Hill, J. Biochem., 7:471-480 (1913).
"Die Kinetik Der Invertinwirkung", Michaelis and Menton, Biochem. Z., 49: 333-338 (1913) (No trnaslation available).
"The Polysaccharide of the Vitreous Humor", Meyer et al., J. Biol. Chem., 107:629-634 (1934).
"The Role of the Mucoid Polysaccharide (Hyaluronic Acid) in the Virulence of Group A Hemolytic Streptococci", Kass et al., J. Of Exp. Med., 79:319-330 (1944).
"The Production of Capsules, Hyaluronic Acid and Hyaluronidase by Group A and Group C Streptocooci", MacLennan, J. Gen. Microbiol., 14:134-142 (1956).
"The Isolation and Characterization of a Hyaluronidase Produced by a Capsulated Strain of Group C Streptococcus", MacLennan, J. Gen. Microbiol., 14:143-152 (1956).
"The Biosynthesis of Hyaluronic Acid by Group a Streptococcus", Markovitz et al., J. Biol. Chem., 234 (9):2343-2350 (1959).
"The Biosynthesis of Hyaluronic Acid by Streptococcus," Stoolmiller, et al., Journal of Biological Chemistry, vol. 244, No. 2, pp. 236-246 (1969).
"Cleavage of Structural Proteins During The Assembly of the Head of Bacteriophage T4", Laemmli, Nature, 227:680-685 (1970).
"The Isolation and Characterization of Hyaluronic Acid From Pasteurella Multocida", Cifonelli, et al., Carbohydrate Research, 14, 272-276, (1970).

(Continued)

Primary Examiner—Robert A. Wax
(74) Attorney, Agent, or Firm—Dunlap, Codding & Rogers, P.C.

(57) ABSTRACT

The present invention relates to a recombinant *Bacillus* host cell containing a recombinant vector including a nucleic acid segment having a coding region segment encoding enzymatically active hyaluronan synthase (HAS). The recombinant *Bacillus* host cell is utilized in a method for producing hyaluronic acid (HA).

37 Claims, 22 Drawing Sheets

OTHER PUBLICATIONS

"A Rapid and Sensitive Method for the Quantitation of Microgram Quantities of Protein Utilizing The Principle of Protein-Dye Binding", Bradford, Analytical Biochemistry, 72:248-254 (1976).

"Synthesis and Assembly of the Membrane Proteins in *E. coli*", Ito et al., Cell, 11:551-559 (1977).

"Electrophoretic Transfer of Proteins from Polyacrylamide Gels to Nitrocellulose Sheets: Procedure and Some Applications", Biochemistry, 76: 4350-4354 (1979).

"Biosynthesis of Hyaluronic Acid by Streptococcus", Sugahara et al., J. Biol. Chem., 254:6252-6261 (1979).

"Modern Genetics", Ayala, et al., Benjamin/Cummings Publishing Col., Menlo Park CA, p. 45 (1980).

"Hyaluronidase Production by Type B Pasteurella Multocida from Cases of Hemorrhagic Septicemia", Carter, et al., Journal of Clinical Microbiology, p. 94-96, (1980).

"Hyaluronate Capsule Prevents Attachment of Group A Streptococci to Mouse Peritoneal Macrophages", Whitnack et al., Infection and Immunity, 31(3):985-991 (1981).

"Strains of *Escherichia coli* Carrying the Structural Gene for Histidyl-tRNA Synthetase on a High Copy-Number Plasmid", Eisenbeis, et al., Mol. Gen. Genet. 183:115-122 (1981).

"Synthesis of Hyaluronate in Differentiated Teratocarcinoma Cells," Prehm, et al., J. Biochem, vol. 211, pp. 181-189 (1983).

"Streptococcal Hyaluronic Acid: Proposed Mechanisms of Degradation and Loss of Synthesis During Stationary Phase", Van de Rijn, J. Bacteriol., 156(3):1059-1065 (1983).

"Hyaluronate is Synthesized at Plasma Membranes", Prehm, Biochem. J., 220:597-600 (1984).

"Subcellular Localization of Hyaluronate Synthase in Oligodendroglioma Cells", Philipson et al., J. Biol. Chem., 259(8):5017-5023 (1984).

"Solubilization of Hyaluronic Acid Synthetic Activity from Streptococci and its Activation with Phospholipids", Triscott et al., J. Biol. Chem., 261(13):6004-6009 (1986).

"Isolation of Streptococcal Hyaluronate Synthase", Prehm et al., Biochem. J., 235:887-889 (1986).

"Isolation, Structure and Expression of Mammalian Genes for Histidyl-tRNA Synthetase," Tsui, et al., Nucleic Acids Research, vol. 15, No. 8, pp. 3349-3367, (1987).

"Role of Cysteine Residues in Glutathione Synthase from *Escherichia coli* B", Kato et al., J. Biol. Chem., 263(24):11646-11651 (1988).

"The Biology of Hyaluronan", Evered and Whelan Eds., CIBA Foundation Symposium 143 (1989).

"The Role of Bacterial Polysaccharide Capsules as Virulence Factors", Moxon et al., Current Topics in Microbiology and Immunology, 150:65-85 (1990).

"Hyaluronic Acid Capsule is a Virulence Factor for Mucoid Group A Streptococci", Wessels et al., Microbiology, 88:8317-8321 (1991).

"Shuttle Vectors Containing a Multiple Cloning Site and a Lacza Gena for Conjugal Transfer of DNA from *Escherichia coli* to Gram-Positive Bacteria," Trieu-Cout, et al., Gene, vol. 102, pp. 99-104, (1991).

"Analysis of the Streptococcal Hyaluronic Acid Synthase Complex Using the Photoaffinity Probe 5-Azido-UDP-Glucuronic Acid," Van de Rijn, et al., J. Biol., Chem., vol. 267, No. 34, pp. 24302-24306, (1992).

"Molecular Characterization of a Locus Required for Hyaluronic Acid Capsule Production in Group A Streptococci," Dougherty, et al., J. Exp. Med., vol. 175, pp. 1291-1299, (1992).

"Hyaluronan," Laurent, et al., FASEB Journal, vol. 6, pp. 2397-2404, (1992).

"Role of Cysteins 640, 656, and 661 in Steroid Binding to Rat Glucocorticoid Receptors", Chakraborti et al., J. Biol. Chem., 267(16):11366-11373 (1992).

"Hyaluronic Acid and A (1-4)-B-D-XYLAN, Extracellular Polysaccharides of *Pasteurella multocida* (Carter Type A) Strain 880", Rosner, et al., Carbohydrate Research, 223, 329-333 (1992).

"Localization of Hyaluronan in Mouse Embryos During Implantation, Gastrulation and Organogenesis", Fenderson et al., Differentiation, 54:85-98 (1993).

"Hyaluronan-Binding Proteins in Development, Tissue Homeostasis, and Disease", Knudson et al., FASEB, 7:1233-1241 (1993).

"Molecular Cloning, Identification, and Sequence of the Hyaluronan Synthase Gene from Group A Streptococcus Pyogenes", DeAngelis et al., J. Biol. Chem., 268(26):19181-19184 (1993).

"Isolation of a Streptococcus Pyogenes Gene Locus That Directs Hyaluronan Biosynthesis in Acapsular Mutants and in Heterologous Bacteria," DeAngelis, et al., J. Biol. Chem., vol. 268, No. 20, pp. 14568-14571, (1993).

"Hyaluronate Synthase: Cloning and Sequencing of the Gene from Streptococcus SP.," Lansing, et al., J. Biochem., vol. 289, pp. 179-184, (1993).

"Molecular Characterization of HASB from an Operon Required for Hyaluronic Acid Synthesis in Group A Streptococci," Dougherty, et al., J. Biol. Chem., vol. 268, No. 10, pp. 7118-7124, (1993).

"Capsular Hyaluronic Acid in *Pasteurella multocida* Type A and its Counterpart in Type D", Pandit, Research in Veterinary Science 54, 20-24 (1993).

"Effects on Virulence of Mutations in a Locus Essential for Hyaluronic Acid Capsule Expression in Group A Streptococci", Wessels et al., Infection and Immunity, 62(2):433-441 (1994).

"A Hyaluronidase Activity of the Sperm Plasma Membrane Protein PH-20 Enables Sperm to Penetrate the Cumulus Cell Layer Surrounding the Egg", Lin et al., The Journal of Cell Biology, 125(5):1157-1163 (1994).

"Dynamics of Lactose Permease of *Escherichia coli* Determined by Site-Directed Fluorescense Labeling", Jung et al., Biochemistry, 33:3980-3985 (1994).

"Cysteine 148 in the Lactose Permease of *Escherichia coli* is a Component of a Substrate Binding Site", Wu et al., Biochemistry, 33:12166-12171 (1994).

"Molecular Characterization of HASA from an Operon Required for Hyaluronic Acid Synthesis in Group A Streptococci," Dougherty, et al., J. Biol. Chem., vol. 269, No. 1, pp. 169-175, (1994).

"The Streptococcus Pyogenes Hyaluronan Sytnhase: Sequence Comparison and Conservation Among Various Group A Strains," DeAngelis, et al., Biochem. and Biophy. Res. Comm., vol. 199, No. 1, pp. 1-10, (1994).

"Molecular Fingerprinting of *Pasteurella multocida* Associated with Progressive Atrophic Rhinitis in Swine Herds". Gardner et al. Database Medline on Diaolog, US Nat'l. Library of Medicine (Bethesda, MD, USA) No. 95161494, Abstract, J. Vet. Diagn. Invest. Oct. 1994, vol. 6, No. 4 pp. 442-447, see entire abstract.

"Hyaluronidase and Chondroitinase Activity of *Pasteurella multocida* Serotype B:2 Involved in Haemorrhagic Septicaemia", Rimler, et al., Veterinary Record 134, 67-68 (1994).

The Elucidation of Novel Capsular Genotypes of Haemophilus Influenzae Type B with the Polymerase Chain Reaction. Leaves et al. J. Medical Microbiology. 1995, vol. 43, pp. 120-124, entire document.

"Homologs of the Xenopus Developmental Gene DG42 are Present in Zebrafish and Mouse and Are Involved in the Synthesis of Nod-Like Chitin Oligosaccharides During Early Embryogenesis", Semino et al., Proc. Natl Acad. Sci. USA, 93:4548-4553 (1996).

"Enzymological Characterization of the *Pasteurella multocida* Hyaluronic Acid Synthase", DeAngelis, Biochemistry, 35 (30): 9768-9771 (1996).

"Construction and Characterization of Potential Live Oral Carrier-Based Vaccine Against Vibrio Chlolerae". Favre et al. Infection and Immunity. Sep. 1996. Vol. 64, No. 9 pagres 3565-3570, entire document.

"Functional Cloning of the cDNA for a Human Hyaluronan Synthase", Shyjan et al., J. Biol. Chem., 271(38):23395-23399 (1996).

"Coating the Surface: A Model for Expression of Capsular Polysialic Acid in *Escherchia coli* K1", Bliss et al., Molecular Microbiology, 21(2):221-231 (1996).

"Molecular Cloning and Characterization of a Putative Mouse Hyaluronan Synthase", Spicer et al., J. Biol. Chem., 271 (38):23400-23406 (1996).

"Expression Cloning and Molecular Characterization of has Protein, a Eukaryotic Hyaluronan Synthase", Itano et al., J. Biol. Chem., 271 (17):9875-9878 (1996).

"Molecular Identification of a Putative Human Hyaluronan Synthase", Watanabe et al., J. Biol. Chem., 271(38):22945-22948 (1996).

"Molecular Cloning of a Human Hyaluronan Synthase", Itano et al., Biochemical and Biophysical Research Communications, 222:816-820 (1996).

"Capsular Hyaluronic Acid-Mediated Adhesion of *Pasteurella multocida* to Turkey Air Sac Macrophages", Pruimboom, et al., Avian Diseases 40:887-893, (1996).

"Molecular Cloning, Expression, and Characterization of the Authentic Hyaluronan Synthase from Group C Streptococcus EQUISIMILIS", Kumari and Weigel, J. Biol. Chem., 272(51): 32539-32546 (1997).

"Identification of Sulfhydryl-Modified Cysteine Residues in the Ligand Binding Pocket or Retinoic Acid Retinoic Acid Receptor β", Wolfgang et al., J. Biol. Chem., 272(2):746-753 (1997).

"Hyaluronan in Morphogenesis", B.P. Toole, Journal of Internal Medicine, 242:35-40 (1997).

"Hyaluronan Synthases", Weigel et al., J. Biol. Chem., 272(22):13997-14000 (1997).

"Hyaluronan Synthase of Chlorella Virus PBCV-1", DeAngelis et al, Science, 278:1800-1803 (1997).

"Site-Directed Spin Labeling of Transmembrane Domain VII and the 4B1 Antibody Epitope in the Lactose Permease of *Escherichia coli*", Voss et al., Biochemistry, 36:15055-15061 (1997).

"Reactive Cysteines of the Yeast Plasma-Membrane H-ATPase (PMA1)", Petrov et al., J. Biol. Chem., 272(3):1688-1693 (1997).

"Identification and Molecular Cloning of a Unique Hyaluronan Synthase from *Pasteurella multocida*", DeAngelis et al., J. Biol. Chem., 273(14): 8454-8458 (1998).

The Capsule Biosynthetic Locus of *Pasteurella multocida* A:1. Chung, et al. FEMS Microbiol. Lett. Sep. 15, 1998, vol. 166, No. 2, pp. 289-296, entire document.

"CYS-Scanning Mutagenesis: A Novel Approach to Structure-Function Relationships in Polytopic Membrane Proteins", Frillingos et al., FASEB, 12:1281-1299 (Oct. 1998).

"Characterization and Molecular Evolution of Vertebrate Hyaluronan Synthase Gene Family", Spicer et al., J. Biol. Chem., 273(4):1923-1932 (1998).

"Eukaryotic Hyaluronan Synthases", Spicer and McDonald, Glycoforum, Sep. 15, 1998.

"The Active Streptococcal Hyaluronan Synthases (HASs) Contain a Single has Monomer and Multiple Cardiolipin Molecules", Tlapak-Simmons et al., J. Biol. Chem., 273(40):26100-26109 (1998).

"Transposon Tn916 Insertional Mutagenesis of *Pasteurella multocida* and Direct Sequencing of Disruption Site", Paul L. DeAngelis, Microbial Pathogenesis, 24: 203-209 (1998).

"Hyaluronan Synthase Expression in Bovine Eyes", Usui et al., Investigative Ophythamology & Visual Science, 40(3):563-567 (Mar. 1999).

Heldermon Coy et al: "Streptococcal Hyaluronan Synthases and the Synthesis of "Designer" Hyaluronan" International Congress Series; New Frontier in Medical Sciences: Redefining Hyaluronan Elsevier Science B.V. {A}, Sarah Burgerhartstraat 25, 1000 AE, Amsterdam, Netherlands Series: International Congress Series (ISSN 0531-5131), 2000, pp. 41-50, XP009047179 & Symposium on New Frontiers in Medical Sciences; Redefining Hyaluronan; Padua, Italy; Jun. 17-19, 1999 ISSN: 0-444-50357-9 *Abstract*.

"Three Isoforms of Mammalian Hyaluronan Synthases Have Distinct Enzymatic Properties", Itano et al., J. Biol. Chem., 274(35):25085-25092 (1999).

"Hyaluronan Synthases: Fascinating Glycosyltransferases from Vertebrates, Bacterial Pathogens and Algal Viruses", P.L. DeAngelis, CMLS, 56:670-682 (1999).

"Membrane Protein Folding and Stability: Physical Principles", White and Wimley, Annu. Rev. Biophys. Biomol. Struc., 28:319-365 (1999).

"Location of Helix III in the Lactose Permease of *Escherichia coli* as Determined by Site-Directed Thiol Cross-Linking", Wang and Kaback, Biochemistry, 38:16777-16782 (1999).

"Kinetic Characterization of the Recombinant Hyaluronan Synthases from Streptococcus Pyogenes and Streptococcus Equisimilis", Tlapak-Simmons, J. Biol. Chem., 274(7):4246-4253 (1999).

"Purification and Lipid Dependence of the Recombinant Hyaluronan Synthases from Streptococcus Pyogenes and Streptococcus Equisimilis", Tlapak-Simmons, J. Biol. Chem., 274(7):4239-4245 (1999).

"Structure/Function Studies of Glycoslytransferases", Breton and Imberty, Current Opinion in Structural Biology, 9:563-571 (1999).

"New Frontiers in Medical Sciences: Redefining Hyaluronan", Abatangelo and Weigel Eds., (2000).

"In Vitro Synthesis of Hyaluronan by a Single Protein Derived from Mouse HAS1 Gene and Characterization of Amino Acid Residues Essential for the Activity", Yoshida et al., J. Biol. Chem., 275(1):497-506 (2000).

"Regulation of Plasminogen Activator Inhibitor-1 and Urokinase by Hyaluronan Fragments in Mouse Macrophages", Horton et al., Am. J. Physiol. Lung Cell Mol. Physiol., 279:L707-L715 (2000).

Jing Wei et al: "Dissection of the Two Transferase Activities of the *Pasteurella multocida* Hyaluronan Synthase: Two Active Sites Exist in One Polypeptide" Glycobiology, vol. 10, No. 9, Sep. 2000, pp. 883-889, XP002326785 ISSN: 0959-6658 *Abstract; Table II*.

"Complete Cysteine-Scanning Mutagenesis and Site Directed Chemical Modification of the Tn10-Encoded Metal-Tetracycline/H Antiporter", Tamura et al., J. Biol. Chem., 276(23):20330-20339 (2001).

"Identification and Disruption of Two Discrete Loci Encoding Hyaluronic Acid Capsule Biosynthesis Genes hasA, hasB, and hasC in Streptococcus Uberis", Ward et al., Infection and Immunity, 69(1):392-399 (2001).

"Topological Organization of the Hyaluronan Synthase from Streptococcus Pyogenes", Heldermon et al., J. Biol. Chem., 276(3):2037-2046 (2001).

"Site-Directed Mutation of Conserved Cysteine Residues Does not Inactivate the Streptococcus Pyogenes Hyaluronan Synthase", Heldermon et al., Glycobiology, 11(12):1017-1024 (2001).

"Molecular Cloning of Rabbit Hyaluronic Acid Synthases and Their Expression Patterns in Synovial Membrane and Articular Cartilage", Ohno et al., Biochimica et Biophysica Acta, 1520 (71-78) (2001).

Kumari Kshama et al: "The Streptococcal Hyaluronan Synthases are Inhibited by Sulfhydryl-Modifying Reagents, but Conserved Cysteine Residues are not Essential for Enzyme Function" Journal of Biological Chemistry, vol. 277(16), Apr. 19, 2002, pp. 13943-13951, XP002326787 ISSN: 0021-9258 *abstract*.

"The Streptococcal Hyaluronan Synthases are Inhibited by Sulfhydryl-Modifying Reagents, But Conserved Cysteine Residues are not Essential for Enzyme Function", Kumari et al., J. Biol. Chem., 277(16):13943-13952 (2002).

```
              211       220       230       240       250       260       270       280
              |---------+---------+---------+---------+---------+---------+---------+---------|
      hHAS1   ALVRTRRCVCVAQRHGGKREVMYTAFKA---LGDSVDYVQVCDSDTRLDPMALLELVRVLDEDPRVGAYGG
      mHAS1   ALVRTRRCVCVAQRHGGKREVMYTAFKA---LGDSVDYVQVCDSDTRLDPMALLELVRVLDEDPRVGAYGG
     xlHAS1   ELVRNQRCVCIMQQHGGKREVMYTAFQA---IGTSVDYVQVCDSDTKLDELATVEMVKVLESMDMYGAVGG
      hHAS2   QLVLSMKSICIMQKHGGKREVMYTAFRA---LGRSVDYVQVCDSDTMLDPASSVEMVKVLEEDPMVGGVGG
     ocHAS2   QLVLSMKSVCIMQKHGGKREVMYTAFRA---LGRSVDYVQVCDSDTMLDPASSVEMVKVLEEDPMVGGVGG
     rnHAS2   QLVLSMKSICIMQKHGGKREVMYTAFRA---LGRSVDYVQVCDSDTMLDPASSVEMVKVLEEDPMVGGVGG
     btHAS2   QLVLSMKSICTMQKHGGKREVMYTAFRA---LGRSVDYVQVCDSDTMLDPASSVEMVKVLEEDPMVGGVGG
      mHAS2   QLVLSMKSICIMQKHGGKREVMYTAFRA---LGRSVDYVQVCDSDTMLDPASSVEMVKVLEEDPMVGGVGG
     ggHAS2   QLVLSMKSVCIMQKHGGKREVMYTAFKA---LGERHNYVQVCDSDTMLDPASSVEMVKVLEEDPMVGGVGG
     xlHAS2   QMVLSMRNVCIMQKHWGKREVMYTAFKA---LGRSVDYVQVCDSDTVLDPASSVEMVKVLEEDIMVGGVGG
      mHAS3   AVVMASTFSCIMQKHGGKREVMYTAFKA---LGNSVDYIQVCDSDTVLDPACTIEMLRVLEEDPQVGGVGG
     ocHAS3   AVVRTSTFSCIMQKHGGKREVMYTAFKA---LGDSVDYIQVCDSDTVLDPACTIEMLRVLEEDPQVGGVGG
      cvHAS   SDF---SRDICVLQPHRGKRECLYTGFQLAKMDPSVNRVVLIDSDTVLEKDAILEVVYPLACDPEIQAYAG
       vNC    SDF---SRDICVLQPHRGKRECLYTGFQLAKMDPSVNRVVLIDSDTVLEKDAILEVVYPLACDPEIQAYAG
       vMA    SDF---SRDICVLQPHRGKRECLYTGFQLAKMDPSVNRVVLIDSDTVLEKDAILEVVYPLACDPEIQAYAG
       vAL    SDF---SRDICVLQPHRGKRECLYTGFQLAKMDPSVNRVVLIDSDTVLEKDAILEVVYPLACDPEIQAYAG
       vCA    SDF---SRDICVLQPHRGKRECLYTGFQLAKMDPSVNRVVLIDSDTVLEKDAILEVVYPLACDPEIQAYAG
      spHAS   VDICRMVIVMRSLVNKGKRHAQAHAFER----SDADVFLTVDSDTYIYPMRLEELLKSFM-DETVYAATG
      seHAS   GDLSSMVIVMRSEKMQGKRHAQAHAFER----SDADVFLTVDSDTYIYPDRLEELLKTFM-DPTVFAATG
      suHAS   G-FGDQVIVHQMPENVGKRHAQAHAFER----SDADVFLTVDSDTYIYPDRLEELLKTFM-DPEVYAATG
   Consensus  ........vc.nq...GKRe..ytaF........sv#.v....DSDT.l.p.a..E.vk.l..#p.v.av.G 281       290       300       310       320       330       340       350
              |---------+---------+---------+---------+---------+---------+---------+---------|
      hHAS1   DVRILNPLDSHVSFLSSLRYHVAFMVERACQSYFHCVSCISGPLGLYRNNLLQQFLEAHYNQKFLGTHCT
      mHAS1   DVRILNPLDSHVSFLSSLRYHVAFMVERACQSYFHCVSCISGPLGLYRNNLLQQFLEAHYNQKFLGTHCT
     xlHAS1   DVRILNPYDSFISFMSSLRYHMAFMVERACQSYFDCVSCISGPLGMYRNDILQVFLEAHYROKFLGTYCT
      hHAS2   DVQILNKYDSHISFLSSVRYHMAFNIERACQSYFGCVQCISGPLGMYRNSLLHEFVEDHYNQEFMGNQCS
     ocHAS2   DVQILNKYDSHISFLSSVRYHMAFNIERACQSYFGCVQCISGPLGMYRNSLLHEFVEDHYNQEFMGNQCS
     rnHAS2   DVQILNKYDSHISFLSSVRYHMAFNIERACQSYFGCVQCISGPLGMYRNSLLHEFVEDHYNQEFMGNQCS
     btHAS2   DVQILNKYDSHISFLSSVRYHMAFNIERACQSYFGCVQCISGPLGMYRNSLLHEFVEDHYNQEFMGSQCS
      mHAS2   DVQILNKYDSHISFLSSVRYHMAFNIERACQSYFGCVQCISGPLGMYRNSLLHEFVEDHYNQEFMGNQCS
     ggHAS2   DVQILNKYDSHISFLSSVRYHMAFNIERACQSYFGCVQCISGPLGMYRNSLLHEFVEDHYNQEFMGSQCS
     xlHAS2   DVQILNKYDSHISFLSSVRYHMAFNIERACQSYFGCVQCISGPLGMYRNSLLHEFIEDHYNQEFLGSQCS
      mHAS3   DVQILNKYDSHISFLSSVRYHMAFNVERACQSYFGCVQCISGPLGMYRNSLLQQFLEDHYHQKFLGSKCS
     ocHAS3   DVQILNKYDSHISFLSSVRYHMAFNVERACQSYFGCVQCISGPLGMYRNSLLQQFLEDHYHQKFLGSKCS
      cvHAS   ECKIHNT-DTLLSLLVAHRYYSAFCVERSAQSFFRTVQCVGGPLGAYK-DIIKEIKDPHISQRFLGQKCT
       vNC    ECKIHNT-DTLLSLLVAHRYYSAFCVERSAQSFFRTVQCVGGPLGAYKIDIIKEIKDPHISQRFLGQKCT
       vMA    ECKIHNT-DTLLSLLVAHRYYSAFCVERSAQSFFRTVQCVGGPLGAYKIDIIKEIKDPHISQRFLGQKCT
       vAL    ECKIHNT-DTLLSLLVAHRYYSAFCVERSAQSFFRTVQCVGGPLGAYKIDIIKEIKDPHISQRFLGQKCT
       vCA    ECKIHNT-DTLLSLLVAHRYYSAFCVERSAQSFFRTVQCVGGPLGAYKIDIIKEIKDPHISQRFLGQKCT
      spHAS   HLNARNRQTNLLTRLTDIRYDNAFGVERAAQSLTGNILVCSGPLSIYRREVIIPNLERYKNQTFLGLPVS
      seHAS   HLNYRNRQTNLLTRLTDIRYDNAFGVERAAQSVTGNILVCSGPLSVYRREVVYPNIDRYIHQTFLGIPVS
      suHAS   HLNARHRQTNLLTRLTDIRYDNAFGVERAAQSVTGNILVCSGPLSIYRRSVGIPNLERYTSQTFLGVPVS
   Consensus  ...i.N...d.Ils.$...RY..AF.!ERaaQS.fg.!.c.sGPLg.Yr.........#.u.nQ.F$G...cs
```

FIG. 2

```
            351       360       370       380       390       400       410       420
            |---------+---------+---------+---------+---------+---------+---------+---------|
     hHAS1  FGDDRHLTNRMLSHGYATKYTSRSRCYSETPSSFLRWLSQQTRWSKSYFREWLYNALWWHRHHA----WMT
     nHAS1  FGDDRHLTNRMLSHGYATKYTSRSRCYSETPSSFLRWLSQQTRWSKSYFREWLYNALWWHRHHA----WMT
    xlHAS1  LGDDRHLTNRVLSHGYRTKYTHKSRAFSETPSLYLRWLNQQTRWTKSYFREWLYNAQWWHKHHI----WMT
     hHAS2  FGDDRHLTNRVLSLGYATKYTARSKCLTETPIEYLRWLNQQTRWSKSYFREWLYNAMWFHKHHL----WMT
    ocHAS2  FGDDRHLTNRVLSLGYATKYTARSKCLTETPIEYLRWLNQQTRWSKSYFREWLYNAMWFHKHHL----WMT
    rnHAS2  FGDDRHLTNRVLSLGYATKYTARSKCLTETPIEYLRWLNQQTRWSKSYFREWLYNAMWFHKHHL----WMT
    btHAS2  FGDDRHLTNRVLSLGYATKYTARSKCLTETPIEYLRWLNQQTRWSKSYFREWLYNAMWFHKHHL----WMT
     nHAS2  FGDDRHLTNRVLSLGYATKYTARSKCLTETPIEYLRWLNQQTRWSKSYFREWLYNAMWFHKHHL----WMT
    ggHAS2  FGDDRHLTNRVLSLGYATKYTARSKCLTETPIEYLRWLNQQTRWSKSYFREWLYNAMWFHKHHL----WMT
    xlHAS2  FGDDRHLTNRVLSLGYATKYTARSKCLTETPTEYLRWLNQQTRWSKSYFREWLYNSLWFHKHHL----WMT
     nHAS3  FGDDRHLTNRVLSLGYRTKYTARSKCLTETPTRYLRWLNQQTRWSKSYFREWLYNSLWFHKHHL----WMT
    ocHAS3  FGDDRHLTNRVLSLGYRTKYTARSKCLTETPTKYLRWLNQQTRWSKSYFREWLYNSLWFHKHHL----WMT
     cvHAS  YGDDRRLTNEILMRGKKVVFTPFAVGWSDSPTNVFRYIVQQTRWSKSWCREIWYTLFAAWKHGLSGIWLA
      vNC  YGDDRRLTNEILMRGKKVVFTPFAVGWSDSPTNVFRYIVQQTRWSKSWCREIWYALFAAWKHGLSGIWLA
       vHA  YGDDRRLTNEILMRGKKVVFTPFAVGWSDSPTNVFRYIVQQTRWSKSWCREIWYTLFAAWKHGLSGIWLA
       vAL  YGDDRRLTNEILMRGKKVVFTPFAVGWSDSPTNVFRYIVQQTRWSKSWCREIWYTLFAAWKHGLSGIWLA
       vCA  YGDDRRLTNEILMRGKKVVFTPFAVGWSDSPTNVFRYIVQQTRWSKSWCREIWYTLFAAWKHGLSGIWLA
     spHAS  IGDDRCLTHYAIDLG-RTVYQSTARCDTDVPFQLKSYLKQQNRWNKSFFRESIISVKKILSWPIVALWTI
     seHAS  IGDDRCLTHYATDLG-KTVYQSTAKCITDVPDKMSTYLKQQNRWNKSFFRESIISVKKIMWNPFVALWTI
     suHAS  IGDDRCLTHYATDLG-KTVYQSTARCDTDVPDKFKVFIKQQNRWNKSFFRESIISVKKLLATPSYAVWTI
 Consensus  .GDDR.LTN..l.lG..tv%t...a.c.t#.P....r.l.QQtRWsKS.fRE..y.......kh.....W..
```

FIG. 2 Continued

SEQUENCE ID NO. 3

5'-GCTGATGAG ACAG G TAT TAAGC primer: se1 (sense, nucleotides $G^{316}$ - $C^{337}$)

SEQUENCE ID NO. 4

5'-ATCAAATTCTCTGACATTGC primer: se2 (antisense, for sense nucleotides $G^{1031}$ - $T^{1050}$)

SEQUENCE ID NO. 5

5'-GACTCAGATACTTATATCTA primer: sesp1 (sense, for nucleotides $G^{475}$ - $A^{494}$)

SEQUENCE ID NO. 6

5'-TTTTTACGTGTTCCCCA primer: sesp2 (antisense, for sense nucleotides $T^{1221}$ - $A^{1244}$)

FIG. 15

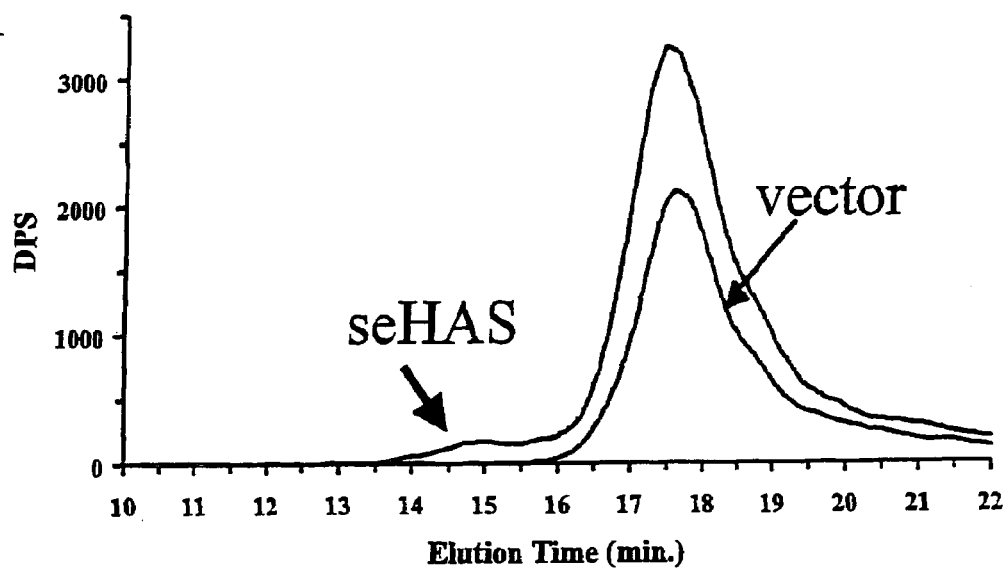
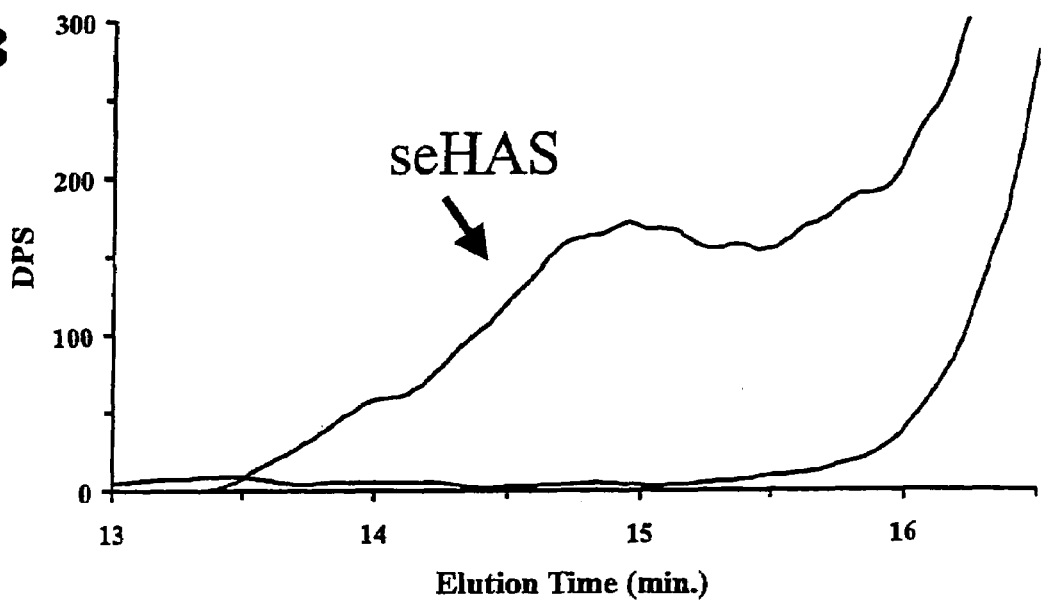
FIGURE 16

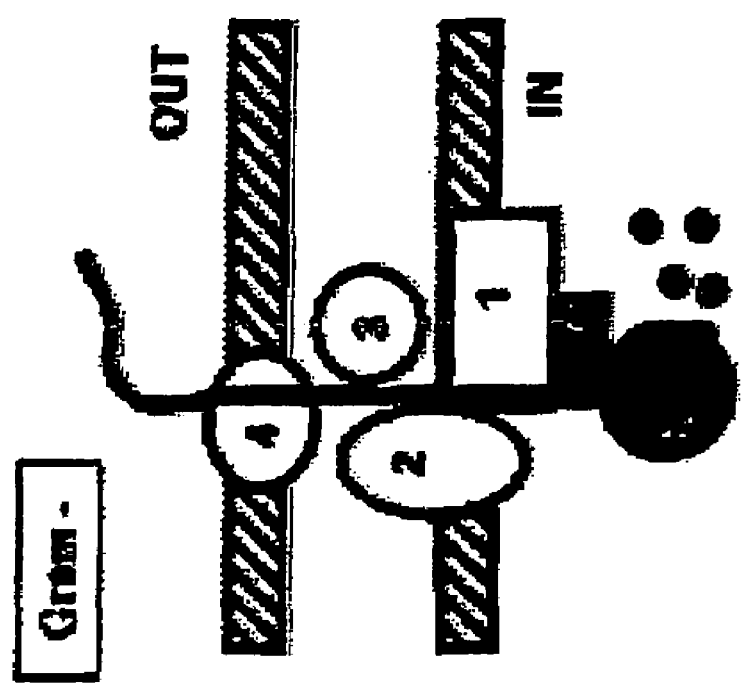
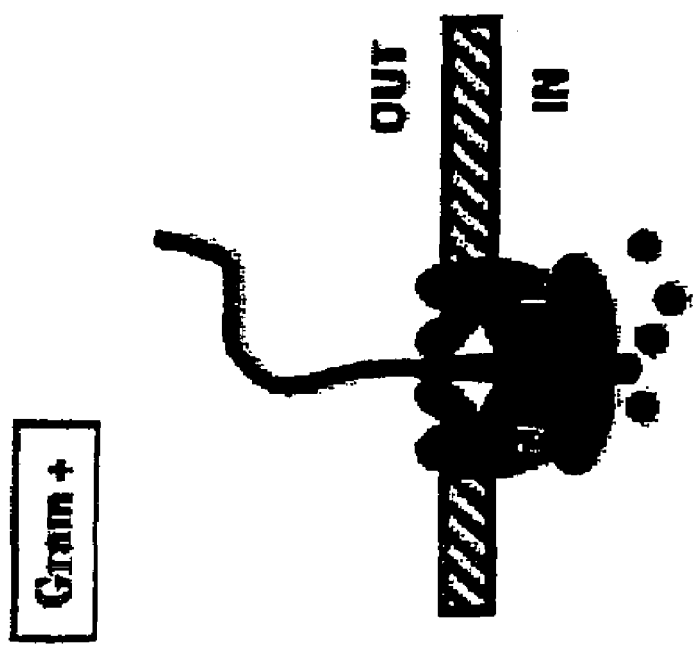
FIGURE 19

HA synthase activity from *Streptococcus pyogenes*, *Streptococcus equisimilis* and *Streptococcus uberis*

HYALURONAN SYNTHASE GENES AND EXPRESSION THEREOF IN *BACILLUS* HOSTS

CROSS-REFERENCE TO RELATED APPLICATIONS

This application is a continuation of U.S. Ser. No. 10/981,632, filed Nov. 5, 2004 now U.S. Pat. No. 7,091,008; which is a divisional of U.S. Ser. No. 10/172,527, filed Jun. 13, 2002, now U.S. Pat. No. 6,951,743, issued Oct. 4, 2005; which is a continuation-in-part of U.S. Ser. No. 09/469,200, filed Dec. 21, 1999, now U.S. Pat. No. 6,833,264, issued Dec. 21, 2004; which is a continuation of U.S. Ser. No. 09/178,851, filed Oct. 26, 1998, now abandoned; and which also claims the benefit under 35 U.S.C. 119(e) of U.S. Provisional Application U.S. Ser. No. 60/064,435, filed Oct. 31, 1997. Said U.S. Ser. No. 10/172,527 is also a continuation-in-part of U.S. Ser. No. 09/146,893, filed Sep. 3, 1998, now U.S. Pat. No. 6,455,304, issued Sep. 24, 2002; which is a continuation of U.S. Ser. No. 08/270,581, filed Jul. 1, 1994, now abandoned. The contents of each of the above-references patent applications/issued patents are hereby expressly incorporated herein by reference in their entirety.

Said application U.S. Ser. No. 10/172,527 also claims benefit under 35 U.S.C. 119(e) of provisional applications U.S. Ser. No. 60/297,788, filed Jun. 13, 2001; U.S. Ser. No. 60/297,744, filed Jun. 13, 2001; and U.S. Ser. No. 60/305,285, filed Jul. 13, 2001; the contents of each of which are hereby expressly incorporated herein by reference in their entirety.

STATEMENT REGARDING FEDERALLY SPONSORED RESEARCH OR DEVELOPMENT

The government owns certain rights in the present invention pursuant to grant number GM35978 from the National Institutes of Health.

BACKGROUND OF THE INVENTION

1. Field of the Invention

The present invention relates to a nucleic acid segment having a coding region encoding enzymatically active hyaluronate synthase (HAS), and to the use of this nucleic acid segment in the preparation of recombinant cells which produce hyaluronate synthase and its hyaluronic acid product. Hyaluronate is also known as hyaluronic acid or hyaluronan.

2. Brief Description of the Related Art

The incidence of streptococcal infections is a major health and economic problem worldwide, particularly in developing countries. One reason for this is due to the ability of Streptococcal bacteria to grow undetected by the body's phagocytic cells, i.e., macrophages and polymorphonuclear cells (PMNs). These cells are responsible for recognizing and engulfing foreign microorganisms. One effective way the bacteria evades surveillance is by coating themselves with polysaccharide capsules, such as a hyaluronic acid (HA) capsule. The structure of HA is identical in both prokaryotes and eukaryotes.

Since HA is generally nonimmunogenic, the encapsulated bacteria do not elicit an immune response and are therefore not targeted for destruction. Moreover, the capsule exerts an antiphagocytic effect on PMNs in vitro and prevents attachment of *Streptococcus* to macrophages. Precisely because of this, in Group A and Group C Streptococci, the HA capsules are major virulence factors in natural and experimental infections. Group A *Streptococcus* are responsible for numerous human diseases including pharyngitis, impetigo, deep tissue infections, rheumatic fever and a toxic shock-like syndrome. The Group C *Streptococcus equisimilis* is responsible for osteomyelitis, pharyngitis, brain abscesses, and pneumonia.

Structurally, HA is a high molecular weight linear polysaccharide of repeating disaccharide units consisting of N-acetylglucosamine (GlcNAc) and glucuronic acid (GlcUA). The number of repeating disaccharides in an HA molecule can exceed 30,000, a $M_r > 10^7$. HA is the only glycosaminogylcan synthesized by both mammalian and bacterial cells, particularly Groups A and C Streptococci and Type A *Pasteurella multocida*. These strains make HA which is secreted into the medium as well as HA capsules. The mechanism by which these bacteria synthesize HA is of broad interest medicinally since the production of the HA capsule is a very efficient and clever way that Streptococci use to evade surveillance by the immune system. Additionally, organic or inorganic molecules coated with HA have properties allowing them to escape detection and destruction by a host's immune system.

HA is synthesized by mammalian and bacterial cells by the enzyme hyaluronate synthase which has been localized to the plasma membrane. It is believed that the synthesis of HA in these organisms is a multi-step process. Initiation involves binding of an initial precursor, UDP-GlcNAc or UDP-GlcUA. This is followed by elongation which involves alternate addition of the two sugars to the growing oligosaccharide chain. The growing polymer is extruded across the plasma membrane region of the cell and into the extracellular space. Although the HA biosynthetic system was one of the first membrane heteropolysaccharide synthetic pathways studied, the mechanism of HA synthesis is still not well understood. This may be because in vitro systems developed to date are inadequate in that de novo biosynthesis of HA has not been accomplished.

The direction of HA polymer growth is still a matter of disagreement among those of ordinary skill in the art. Addition of the monosaccharides could be to the reducing or nonreducing end of the growing HA chain. Furthermore, questions remain concerning (i) whether nascent chains are linked covalently to a protein, to UDP or to a lipid intermediate, (ii) whether chains are initiated using a primer, and (iii) the mechanism by which the mature polymer is extruded through the plasma membrane of the *Streptococcus*. Understanding the mechanism of HA biosynthesis may allow development of alternative strategies to control Streptococcal and *Pasteurella* infections by interfering in the process.

HA has been identified in virtually every tissue in vertebrates and has achieved widespread use in various clinical applications, most notably and appropriately as an intra-articular matrix supplement and in eye surgery. The scientific literature has also shown a transition from the original perception that HA is primarily a passive structural component in the matrix of a few connective tissues and in the capsule of certain strains of bacteria to a recognition that this ubiquitous macromolecule is dynamically involved in many biological processes: from modulating cell migration and differentiation during embryogenesis to regulation of extracellular matrix organization and metabolism to important roles in the complex processes of metastasis, wound healing, and inflammation. Further, it is becoming clear that HA is highly metabolically active and that cells focus much attention on the processes of its synthesis and catabolism. For example, the half-life of HA in tissues ranges from 1 to 3 weeks in cartilage to <1 day in epidermis. HA is also used in numerous technical applications (e.g., lubricating compounds), cosmetics and neutraceuticals.

It is now clear that a single protein utilizes both sugar substrates to synthesize HA, i.e., that HA synthases are single enzymes that have dual catalytic properties. The abbreviation HAS, for HA synthase, has gained widespread support for designating this class of enzymes. Markovitz et al. successfully characterized the HAS activity from *Streptococcus pyogenes* and discovered the enzymes's membrane localization and its requirements for sugar nucleotide precursors and $Mg^{2+}$. Prehm found that elongating HA, made by B6 cells, was digested by hyaluronidase added to the medium and proposed that HAS resides at the plasma membrane. Philipson and Schwartz also showed that HAS activity cofractionated with plasma membrane markers in mouse oligodendroglioma cells.

HAS assembles high $M_r$ HA that is simultaneously extruded through the membrane into the extracellular space (or to make the cell capsule in the case of bacteria) as glycosaminoglycan synthesis proceeds. This mode of biosynthesis is unique among macromolecules since nucleic acids, proteins, and lipids are synthesized in the nucleus, endoplasmic reticulum/Golgi, cytoplasm, or mitochondria. The extrusion of the growing chain into the extracellular space also allows for unconstrained polymer growth, thereby achieving the exceptionally large size of HA, whereas confinement of synthesis within a Golgi or post-Golgi compartment limits the overall amount or length of the polymers formed. High concentrations of HA within a confined lumen may also create a high viscosity environment that might be deleterious for other organelle functions.

Several studies have attempted to solubilize, identify, and purify HAS from strains of Streptococci that make a capsular coat of HA as well as from eukaryotic cells. Although the streptococcal and murine oligodendroglioma enzymes were successfully detergent-solubilized and studied, efforts to purify an active HAS for further study or molecular cloning remained unsuccessful for decades. Prehm and Mausolf used periodate-oxidized UDP-GlcUA or UDP-GlcNAc to affinity label a protein of ~52 kDa in streptococcal membranes that co-purified with HAS. This led to a report claiming that the Group C streptococcal HAS had been cloned, which was unfortunately erroneous. This study failed to demonstrate expression of an active synthase and may have actually cloned a peptide transporter. Triscoft and van de Rijn used digitonin to solubilize HAS from streptococcal membranes in an active form. Van de Rijn and Drake selectively radiolabeled three streptococcal membrane proteins of 42, 33, and 27 kDa with 5-azido-UDP-GlcUA and suggested that the 33-kDa protein was HAS. As shown later, however, HAS actually turned out to be the 42-kDa protein.

Despite these efforts, progress in understanding the regulation and mechanisms of HA synthesis was essentially stalled, since there were no molecular probes for HAS mRNA or HAS protein. A major breakthrough occurred in 1993 when DeAngelis et al. reported the molecular cloning and characterization of the Group A streptococcal gene encoding the protein HasA. This gene was known to be part of an operon required for bacterial HA synthesis, although the function of this protein, which is now designated as spHAS (the *S. pyogenes* HAS), was unknown. spHAS was subsequently proven to be responsible for HA elongation and was the first glycosaminoglycan synthase identified and cloned and then successfully expressed. The *S. pyogenes* HA synthesis operon encodes two other proteins. HasB is a UDP-glucose dehydrogenase, which is required to convert UDP-glucose to UDP-GlcUA, one of the substrates for HA synthesis. HasC is a UDP-glucose pyrophosphorylase, which is required to convert glucose 1-phosphate and UTP to UDP-glucose. Co-transfection of both hasA and hasB genes into either acapsular *Streptococcus* strains or *Enterococus faecalis* conferred them with the ability to synthesize HA and form a capsule. This provided the first strong evidence that spHAS (hasA) was an HA synthase.

The elusive HA synthase gene was finally cloned by a transposon mutagenesis approach, in which an acapsular mutant Group A strain was created containing a transposon interruption of the HA synthesis operon. Known sequences of the transposon allowed the region of the junction with streptococcal DNA to be identified and then cloned from wild-type cells. The encoded spHAS was 5–10% identical to a family of yeast chitin synthases and 30% identical to the *Xenopus laevis* protein DG42 (developmentally expressed during gastrulation), whose function was unknown at the time. DeAngelis and Weigel expressed the active recombinant spHAS in *Escherichia coli* and showed that this single purified gene product synthesizes high $M_r$ HA when incubated in vitro with UDP-GlcUA and UDP-GlcNAc, thereby showing that both glycosyltransferase activities required for HA synthesis are catalyzed by the same protein, as first proposed in 1959. Utilizing the knowledge that (i) spHAS was a dual action single enzyme, and (ii) the areas of sequence homology between the spHAS, chitin synthase, and DG42, the almost simultaneous identification of eukaryotic HAS cDNAs in 1996 by four laboratories, further strengthened the inventor's protein hypothesis that HAS is a multigene family encoding distinct isozymes. Two genes (HAS1 and HAS2) were quickly discovered in mammals, and a third gene HAS3 was later discovered. A second streptococcal seHAS or *Streptococcus equisimilis* hyaluronate synthase, was identified and is disclosed in detail in U.S. Ser. No. 09/469,200, filed Dec. 21, 1999, the contents of which are expressly incorporated herein in their entirety by reference. The seHAS protein has a high level of identity (approximately 70 percent) to the spHAS enzyme. This identity, however, is interesting because the seHAS gene does not cross-hybridize to the spHAS gene.

Membranes prepared from *E. coli* expressing recombinant seHAS synthesize HA when both substrates are provided. The results confirm that the earlier report of Lansing et al. claiming to have cloned the Group C HAS was wrong. Unfortunately, several studies have employed antibodies to this uncharacterized 52-kDa streptococcal protein to investigate what was believed to be eukaryotic HAS.

Itano and Kimata used expression cloning in a mutant mouse mammary carcinoma cell line, unable to synthesize HA, to clone the first putative mammalian HAS cDNA (mmHAS1). Subclones defective in HA synthesis fell into three separate classes that were complementary for HA synthesis in somatic cell fusion experiments, suggesting that at least three proteins are required. Two of these classes maintained some HA synthetic activity, whereas one showed none. The latter cell line was used in transient transfection experiments with cDNA prepared from the parental cells to identify a single protein that restored HA synthetic activity. Sequence analyses revealed a deduced primary structure for a protein of ~65 kDa with a predicted membrane topology similar to that of spHAS. mmHAS1 is 30% identical to spHAS and 55% identical to DG42. The same month this report appeared, three other groups submitted papers describing cDNAs encoding what was initially thought to be the same mouse and human enzyme. However, through an extraordinary circumstance, each of the four laboratories had discovered a separate HAS isozyme in both species.

Using a similar functional cloning approach to that of Itano and Kimata, Shyjan et al. identified the human homolog of HAS 1. A mesenteric lymph node cDNA library was used to transfect murine mucosal T lymphocytes that were then screened for their ability to adhere in a rosette assay. Adhesion of one transfectant was inhibited by antisera to CD44, a known cell surface HA-binding protein, and was abrogated directly by pretreatment with hyaluronidase. Thus, rosetting by this transfectant required synthesis of HA. Cloning and sequencing of the responsible cDNA identified hsHAS1. Itano and Kimata also reported a human HAS1 cDNA isolated from a fetal brain library. The hsHAS1 cDNAs reported by the two groups, however, differ in length; they encode a 578 or a 543 amino acid protein. HAS activity has only been demonstrated for the longer form.

Based on the molecular identification of spHAS as an authentic HA synthase and regions of near identity among DG42, spHAS, and NodC (a β-GlcNAc transferase nodulation factor in *Rhizobium*), Spicer et al. used a degenerate RT-PCR approach to clone a mouse embryo cDNA encoding a second distinct enzyme, which is designated mmHAS2. Transfection of mmHAS2 cDNA into COS cells directed de novo production of an HA cell coat detected by a particle exclusion assay, thereby providing strong evidence that the HAS2 protein can synthesize HA. Using a similar approach, Watanabe and Yamaguchi screened a human fetal brain cDNA library to identify hsHAS2. Fulop et al. independently used a similar strategy to identify mmHAS2 in RNA isolated from ovarian cumulus cells actively synthesizing HA, a critical process for normal cumulus oophorus expansion in the pre-ovulatory follicle. Cumulus cell-oocyte complexes were isolated from mice immediately after initiating an ovulatory cycle, before HA synthesis begins, and at later times when HA synthesis is just beginning (3 h) or already apparent (4 h). RT-PCR showed that HAS2 mRNA was absent initially but expressed at high levels 3–4 h later suggesting that transcription of HAS2 regulates HA synthesis in this process. Both hsHAS2 are 552 amino acids in length and are 98% identical. mmHAS1 is 583 amino acids long and 95% identical to hsHAS1, which is 578 amino acids long.

Most recently Spicer et al. used a PCR approach to identify a third HAS gene in mammals. The mmHAS3 protein is 554 amino acids long and 71, 56, and 28% identical, respectively, to mmHAS1, mmHAS2, DG42, and spHAS. Spicer et al. have also localized the three human and mouse genes to three different chromosomes (HAS1 to hsChr 19/mmChr 17; HAS2 to hsChr 8/mmChr 15; HAS3 to hsChr 16/mmChr 8). Localization of the three HAS genes on different chromosomes and the appearance of HA throughout the vertebrate class suggest that this gene family is ancient and that isozymes appeared by duplication early in the evolution of vertebrates. The high identity (~30%) between the bacterial and eukaryotic HASs also suggests that the two had a common ancestral gene. Perhaps primitive bacteria usurped the HAS gene from an early vertebrate ancestor before the eukaryotic gene products became larger and more complex. Alternatively, the bacteria could have obtained a larger vertebrate HAS gene and deleted regulatory sequences nonessential for enzyme activity.

The discovery of *X. laevis* DG42 by Dawid and co-workers played a significant role in these recent developments, even though this protein was not known to be an HA synthase. Nonetheless, that DG42 and spHAS were 30% identical was critical for designing oligonucleotides that allowed identification of mammalian HAS2. Ironically, definitive evidence that DG42 is a bona fide HA synthase was reported only after the discoveries of the Mammalian isozymes, when DeAngelis and Achyuthan expressed the recombinant protein in yeast (an organism that cannot synthesize HA) and showed that it synthesizes HA when isolated membranes are provided with the two substrates. Meyer and Kreil also showed that lysates from cells transfected with cDNA for DG42 synthesize elevated levels of HA. Now that its function is known, DG42 can, therefore, be designated XlHAS.

There are common predicted structural features shared by all the HAS proteins, including a large central domain and clusters of 2–3 transmembrane or membrane-associated domains at both the amino and carboxyl ends of the protein. The central domain, which comprises up to ~88% of the predicted intracellular HAS protein sequences, probably contains the catalytic regions of the enzyme. This predicted central domain is 264 amino acids long in spHAS (63% of the total protein) and 307–328 residues long in the eukaryotic HAS members (54–56% of the total protein). The exact number and orientation of membrane domains and the topological organization of extracellular and intracellular loops have not yet been experimentally determined for any HAS.

spHAS is a HAS family member that has been purified and partially characterized. Initial studies using spHAS/alkaline phosphatase fusion proteins indicate that the N terminus, C terminus, and the large central domain of spHAS are, in fact, inside the cell. spHAS has 6 cysteines, whereas HAS1, HAS2, and HAS3 have 13, 14 and 14 Cys residues, respectively. Two of the 6 Cys residues in spHAS are conserved and identical in HAS1 and HAS2. Only one conserved Cys residue is found at the same position (Cys-225 in spHAS) in all the HAS family members. This may be an essential Cys whose modification by sulfhydryl poisons partially inhibits enzyme activity. The possible presence of disulfide bonds or the identification of critical Cys residues needed for any of the multiple HAS functions noted below has not yet been elucidated for any members of the HAS family.

In addition to the proposed unique mode of synthesis at the plasma membrane, the HAS enzyme family is highly unusual in the large number of functions required for the overall polymerization of HA. At least six discrete activities are present within the HAS enzyme: binding sites for each of the two different sugar nucleotide precursors (UDP-GlcNAc and UDP-GlcUA), two different glycosyltransferase activities, one or more binding sites that anchor the growing HA polymer to the enzyme (perhaps related to a $B-X_7-B$ motif, and a ratchet-like transfer mechanism that moves the growing polymer one or two sugars at a time. This later activity is likely coincident with the stepwise advance of the polymer through the membrane. All of these functions, and perhaps others as yet unknown, are present in a relatively small protein ranging in size from 419 (spHAS) to 588 (xHAS) amino acids.

Although all the available evidence supports the conclusion that only the spHAS protein is required for HA biosynthesis in bacteria or in vitro, it is possible that the larger eukaryotic HAS family members are part of multicomponent complexes. Since the eukaryotic HAS proteins are ~40% larger than spHAS, their additional protein domains could be involved in more elaborate functions, such as intracellular trafficking and localization, regulation of enzyme activity, and mediating interactions with other cellular components.

The unexpected finding that there are multiple vertebrate HAS genes encoding different synthases strongly supports the emerging consensus that HA is an important regulator of cell behavior and not simply a structural component in tissues. Thus, in less than six months, the field moved from one known, cloned HAS (spHAS) to recognition of a multigene family that promises rapid, numerous, and exciting future advances in our understanding of the synthesis and biology of HA.

For example, disclosed hereinafter are the sequences of HAS genes from *Pasteurella multocida, Paramecium bursaria* Chlorella virus (PBCV-1), *Streptococcus pyogenes, Streptococcus uberis, Sulfolobus solfataricus, Bacillus anthracis* plasmid pXO1, and *Ectocarpus siliculosus* virus. The presence of hyaluronan synthase in these systems and the purification and use of the hyaluronan synthase from these different systems indicates an ability to purify and isolate nucleic acid sequences encoding enzymatically active hyaluronan synthase in many different prokaryotic and viral sources, indeed, from microbial sources in general.

Group C *Streptococcus equisimilis* strain D181 synthesizes and secretes hyaluronic acid (HA). Investigators have used this strain and Group A *Streptococcus pyogenes* strains, such as S43 and A111, to study the biosynthesis of HA and to characterize the HA-synthesizing activity in terms of its divalent cation requirement, precursor (UDP-GlcNAc and UDP-GlcUA) utilization, and optimum pH.

Traditionally, HA has been prepared commercially by isolation from either rooster combs or extracellular media from Streptococcal cultures. One method which has been developed for preparing HA is through the use of cultures of HA-producing Streptococcal bacteria. U.S. Pat. No. 4,517, 295, incorporated by reference herein in its entirety, describes such a procedure wherein HA-producing Streptococci are fermented under anaerobic conditions in a $CO_2$-enriched growth medium. Under these conditions, HA is produced and can be extracted from the broth. It is generally felt that isolation of HA from rooster combs is laborious and difficult, since one starts with HA in a less pure state. The advantage of isolation from rooster combs is that the HA produced is of higher molecular weight. However, preparation of HA by bacterial fermentation is easier, since the HA is of higher purity to start with. Usually, however, the molecular weight of HA produced in this way is smaller than that from rooster combs. Additionally, HA prepared by Streptococcal fermentation oftentimes elicits immune responses as does HA obtained from rooster combs. Therefore, a technique that allows for the production of high molecular weight HA by bacterial fermentation is a distinct improvement over existing procedures.

As mentioned previously, high molecular weight HA has a wide variety of useful applications—ranging from cosmetics to eye surgery. Due to its potential for high viscosity and its high biocompatibility, HA finds particular application in eye surgery as a replacement for vitreous fluid. HA has also been used to treat racehorses for traumatic arthritis by intra-articular injections of HA, in shaving cream as a lubricant, and in a variety of cosmetic products due to its physiochemical properties of high viscosity and its ability to retain moisture for long periods of time. In fact, in August 1997 the U.S. Food and Drug Agency approved the use of high molecular weight HA in the treatment of severe arthritis through the injection of such high molecular weight HA directly into the affected joints. In general, the higher the molecular weight of HA that is employed the better. This is because HA solution viscosity increases with the average molecular weight of the individual HA polymer molecules in the solution. Unfortunately, very high molecular weight HA, such as that ranging up to $10^7$, has been difficult to obtain by currently available isolation procedures. The recombinant methods of production disclosed herein, however, allow for the production of HA having a molecular weight of up to $10^7$ and greater.

To address these or other difficulties, there is a need for new methods and constructs that can be used to produce HA having one or more improved properties such as greater purity or ease of preparation. In particular, there is a need to develop methodology for the production of larger amounts of relatively high molecular weight and relatively pure HA than is currently commercially available. There is yet another need to be able to develop methodology for the production of HA having a modified size distribution ($HA_{\Delta size}$) as well as HA having a modified structure ($HA_{\Delta mod}$).

Industrial enzyme production is a $1.5 billion per year business, and seventy percent of these products are produced from *Bacillus* species. The advantage of using an expression system effective in *Bacillus* strains is that *Bacillus* is an effective secretor of proteins, and therefore substitution of *Bacillus* for *E. coli* or yeast in processes for the production of genetically-engineered proteins yields an enhanced secretion of the protein in question. *Bacillus* strains are also "Generally Recognized As Safe" or "GRAS" micro-organisms, as opposed to other commonly used bacterial strains, such as *E. coli*. *Bacillus* has long been used in the food and drink industry and in the production of antibiotics. One advantage of *Bacillus* is that it does not contain pyrogenic substances or produce toxins. There is extensive industrial experience in using *Bacillus* in fermentations, such as in the production of detergent proteases and alpha-amylase.

The present invention addresses one or more shortcomings in the art. Using recombinant DNA technology, methods of producing enzymatically active HAS in a *Bacillus* cell into which a purified nucleic acid segment having a coding region encoding enzymatically active HAS has been introduced is disclosed and claimed in conjunction with the preparation of recombinant *Bacillus* cells which produce HAS and its hyaluronic acid product.

BRIEF SUMMARY OF THE INVENTION

The present invention involves the application of recombinant DNA technology to solving one or more problems in the art of hyaluronic acid (HA) preparation. These problems are addressed through the isolation and use of a nucleic acid segment having a coding region encoding an enzymatically active hyaluronate synthase (HAS) gene, a gene responsible for HA chain biosynthesis, such as a HAS gene from Group A or C *Streptococcus, Pasteurella multocida, Sulfolobus solfataricus,* and *Ectocarpus siliculosus* virus. The HAS gene disclosed herein were cloned from DNA of an appropriate microbial source and engineered into useful recombinant constructs which were introduced into a *Bacillus* cell for the preparation of HA and for the preparation of large quantities of the HAS enzyme itself.

The terms "hyaluronic acid synthase", "hyaluronate synthase", "hyaluronan synthase" and "HA synthase", are used interchangeably to describe an enzyme that polymerizes a glycosaminoglycan polysaccharide chain composed of alternating glucuronic acid and N-acetylglucosamine sugars, β1,3 and β1,4 linked. The term "seHAS", for example, describes the HAS enzyme derived from *Streptococcus equisimilis*, wherein expression of the gene encoding the seHAS enzyme correlates with virulence of Streptococcal Group A and Group C strains by providing a means of escaping phagocytosis and immune surveillance.

The present invention concerns the isolation and characterization of hyaluronate or hyaluronic acid synthase genes, cDNAs, and gene products (HAS), as may be used for the polymerization of glucuronic acid and N-acetylglucosamine into the glycosaminoglycan hyaluronic acid. The present invention identifies the HAS locus and discloses the nucleic acid sequences which encode for enzymatically active HAS genes from *Streptococcus equisimilis, Streptococcus pyogenes, Streptococcus uberis, Pasteurella multocida, Sulfolobus solfactaricus, Bacillus anthracis* pXO1, and *Ectocarpus siliculosus* virus. The HAS genes also provides new probes to assess the potential of bacterial specimens to produce hyaluronic acid.

Through the application of techniques and knowledge set forth herein, those of skill in the art will be able to obtain additional nucleic acid segments encoding HAS genes. As those of skill in the art will recognize, in light of the present disclosure, these advantages provide significant utility in being able to control the expression of the HAS gene and control the nature of the HAS gene product, the HAS enzyme, that is produced.

Accordingly, the invention is directed to the isolation of a purified nucleic acid segment which has a coding region encoding enzymatically active HAS, whether it be from prokaryotic or eukaryotic sources. This is possible because the enzyme, and indeed the gene, is one found in both eukaryotes and some prokaryotes. Eukaryotes are also known to produce HA and thus have HA synthase genes that can be employed in connection with the invention.

HA synthase-encoding nucleic acid segments of the present invention are defined as being isolated free of total chromosomal or genomic DNA such that they may be readily manipulated by recombinant DNA techniques. Accordingly, as used herein, the phrase "a purified nucleic acid segment" refers to a DNA segment isolated free of unrelated chromosomal or genomic DNA and retained in a state rendering it useful for the practice of recombinant techniques, such as DNA in the form of a discrete isolated DNA fragment, or a vector (e.g., plasmid, phage or virus) incorporating such a fragment.

The present invention comprises a recombinant host cell, wherein the recombinant host cell is a *Bacillus* cell comprising a recombinant vector comprising a purified nucleic acid segment having a coding region encoding enzymatically active hyaluronan synthase of SEQ ID NO:2, 10, 12, 14, 16, 18 or 20. The purified nucleic acid segment may comprise a nucleotide sequence in accordance with SEQ ID NO:1, 9, 11, 13, 15, 17 or 19. The recombinant vector may be introduced into the *Bacillus* cell by at least one of transformation, transfection, transduction, and electroporation.

The coding region described herein above may be under the control of a promoter, such as a Gram-positive compatible promoter or a *Bacillus*-compatible promoter. The recombinant host cell may also include at least one modified RNA polymerase promoter wherein, when the modified RNA polymerase promoter is recognized by an RNA polymerase, the RNA polymerase is capable of expressing RNA in an amount greater than an endogenous RNA polymerase promoter. Such modification may be a mutation or the presence of tandem promoter elements, which may be the same or different promoter elements. In addition, the recombinant host cell may further include at least one additional mRNA stabilizing or destabilizing element than is found in a native *Bacillus* cell.

The *Bacillus* cell may have enhanced production of at least one of UDP-GlcUA and UDP-GlcNAc. Optionally, the recombinant host cell may further have at least one purified nucleic acid segment having a coding region encoding a functionally active enzyme in a UDP-sugar precursor pathway enzyme, such as an enzymatically active UDP-GlcUA biosynthetic pathway enzyme selected from the group consisting of UDP-glucose dehydrogenase, UDP-glucose pyrophosphorylase, and combinations thereof. Such purified nucleic acid segment may be provided on the above-described recombinant vector or may be provided on a different recombinant vector. When provided on the same vector, the two coding regions may be under the control of at least one copy of at least one promoter or under the control of different promoters. The presence of the at least one nucleic acid segment encoding a UDP-sugar precursor biosynthesis pathway enzyme will provide the recombinant host cell with an activity greater than a native host cell expressing an endogenous UDP-sugar precursor biosynthesis pathway enzyme.

In a further alternative, the recombinant host cell may include at least one mutated UDP-sugar precursor biosynthesis gene, wherein the mutation increases the half-life of a mRNA transcribed therefrom, encodes a mRNA having an increased translational efficiency or occurs in a ribosome binding site in the UDP-sugar precursor biosynthesis gene such that a ribosome has an increased binding affinity for the ribosome binding site.

The present invention further comprises a method of producing hyaluronic acid, which comprises constructing the recombinant host cell described herein above by introducing the purified nucleic acid segment(s) described herein above and growing the recombinant host cell in a medium to secrete hyaluronic acid. The *Bacillus* host may be grown at a temperature in the range of from about 25° C. to about 42° C. in chemically defined media, complex media or a medium containing glucose and at least one of N-acetylglucosamine and glucosamine. The secreted hyaluronic acid is then recovered, and the recovered hyaluronic acid may further be extracted from the medium and then purified. For example, the hyaluronic acid may be separated from cells and debris by at least one of filtration, centrifugation and flocculation, followed by concentrating the hyaluronic acid and then separated the concentrated hyaluronic acid from the medium by at least one method selected from the group consisting of precipitation, ultrafiltration and dialysis. This separation may further include the addition of trichloroacetic acid, which facilitates in separating cells and debris from the hyaluronic acid. The precipitation agent may be at least one of an alcohol, an organic solvent or compound and an aliphatic positively-charged salt, and may be selected from the group consisting of ethanol, isopropanol, acetone, cetyl triammonium bromide or cetyl pyridinium chloride.

The present invention further comprises hyaluronic acid prepared by the methods described herein above.

BRIEF DESCRIPTION OF THE SEVERAL VIEWS OF THE DRAWINGS

FIG. 1 depicts that cross hybridization between seHAS and spHAS genes does not occur. The Group A probe used in lanes 1 and 2 only hybridizes with Group A DNA (lane 2) while the Group C probe used in lanes 3 and 4 only hybridizes with lane 3.

FIG. 2 figuratively depicts the relatedness of seHAS to the bacterial, viral and eukaryotic HAS proteins.

FIG. 3 figuratively depicts possible evolutionary relationships and similarities among some of the known hyaluronan synthases.

FIG. 4 depicts the HA size distribution produced by various engineered Streptococcal HAS enzymes.

FIG. 5 figuratively depicts the overexpression of recombinant seHAS and spHAS in *E. coli*.

FIG. 6 depicts recombinant HA production in *Bacillus subtilis* and *Bacillus licheniformis*. Digital image of an agarose gel stained for hyaluronan. Different bacterial species were transformed with the indicated plasmids containing the hasB gene and either a functional hasA gene (pPD41Δ5) or a nonfunctional hasA gene (pPD41ΔEcoRV). Each lane represents an independent colony seeded into fresh growth medium and all cultures were harvested at the same time. The Absorbance at 600 nm when the cultures were harvested is noted at the bottom. Medium was removed after centrifugation of cells and analyzed by agarose gel electrophoresis. HA was demonstrated by the dark staining with StainsAll. In a separate experiment virtually all the stained material produced by the transformed bacteria was removed by treatment with the specific hyaluronic acid lyase, confirming that the material is HA. The bacterial strains containing pPD41ΔEcoRV should not be able to make HA and they were all, in fact, negative. The *B. licheniformis* cultures also demonstrated HA production.

Figure 11:
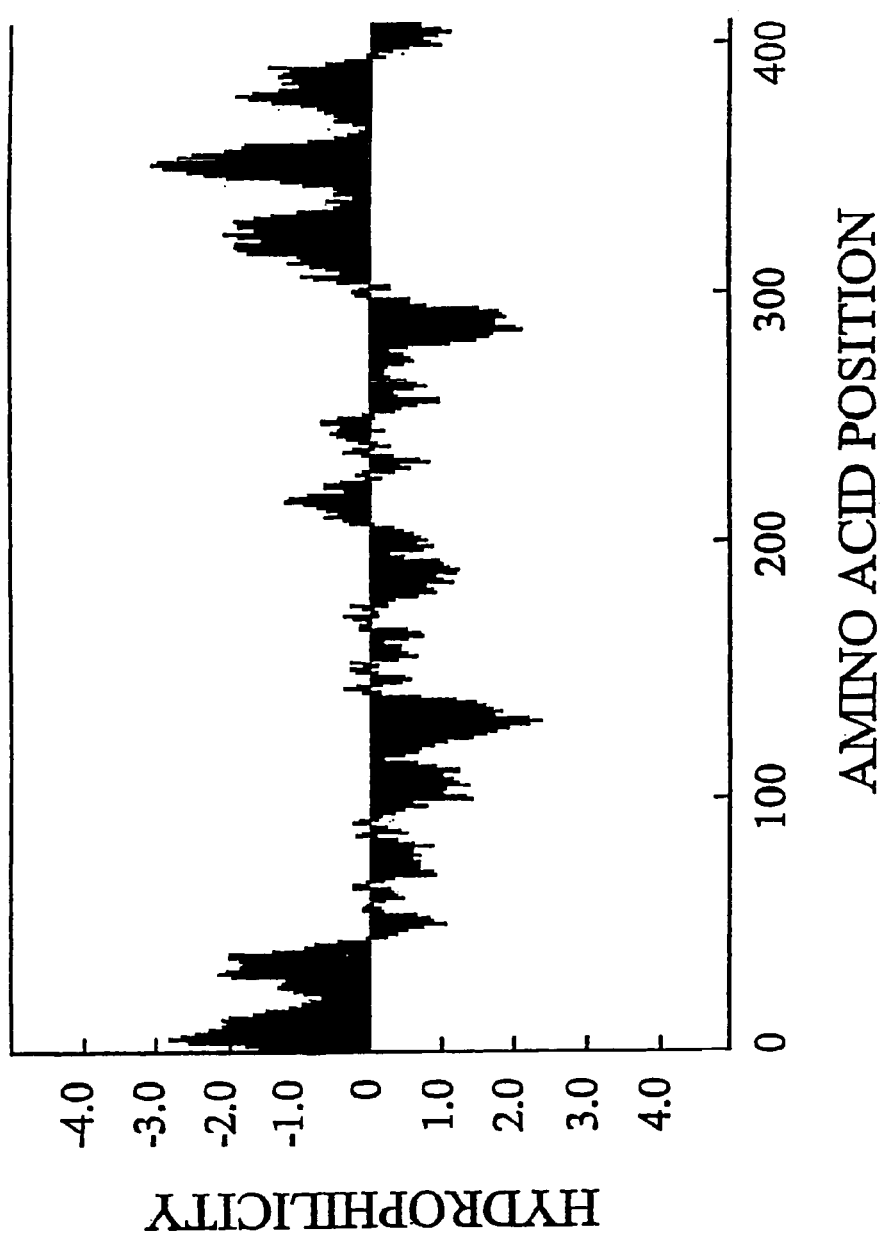

FIG. 11 graphically depicts the hydropathy plots for seHAS and predicted membrane associated regions.

Figure 12:
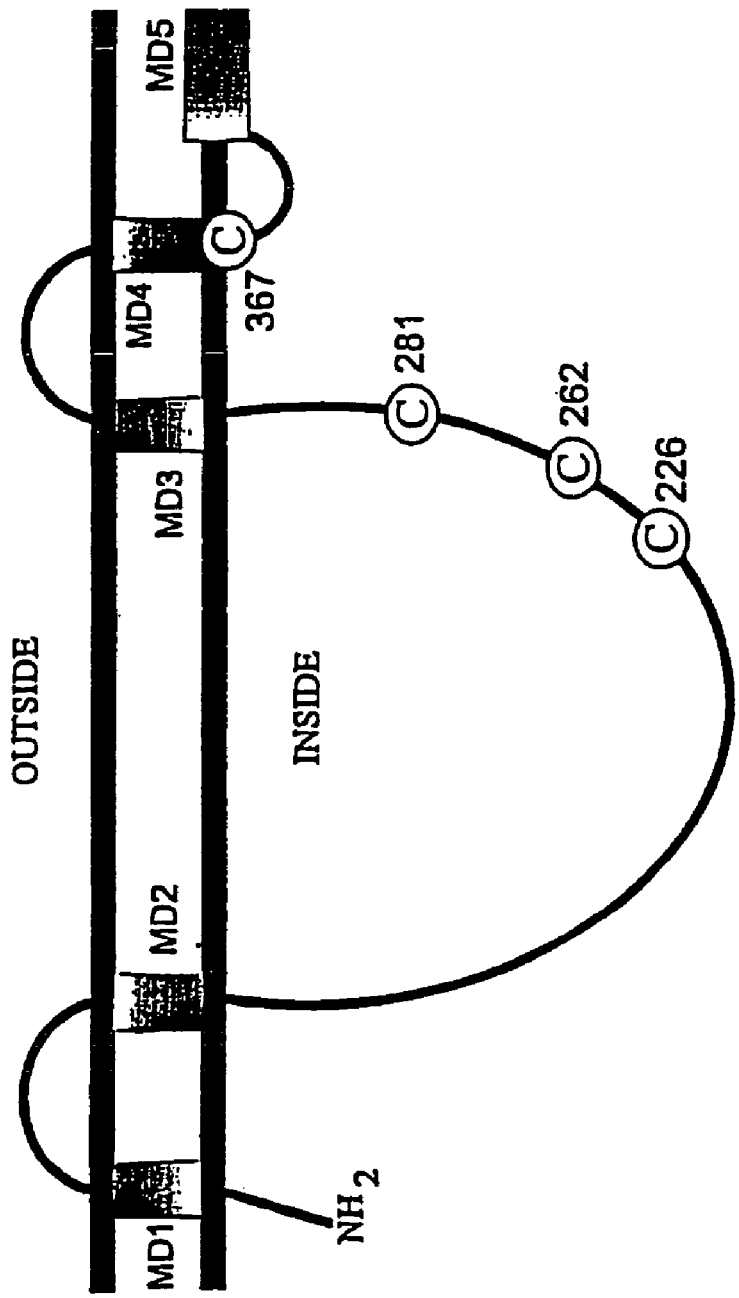

FIG. 12 is a graphical model for the topologic organization of seHAS in the membrane.

Figure 13:
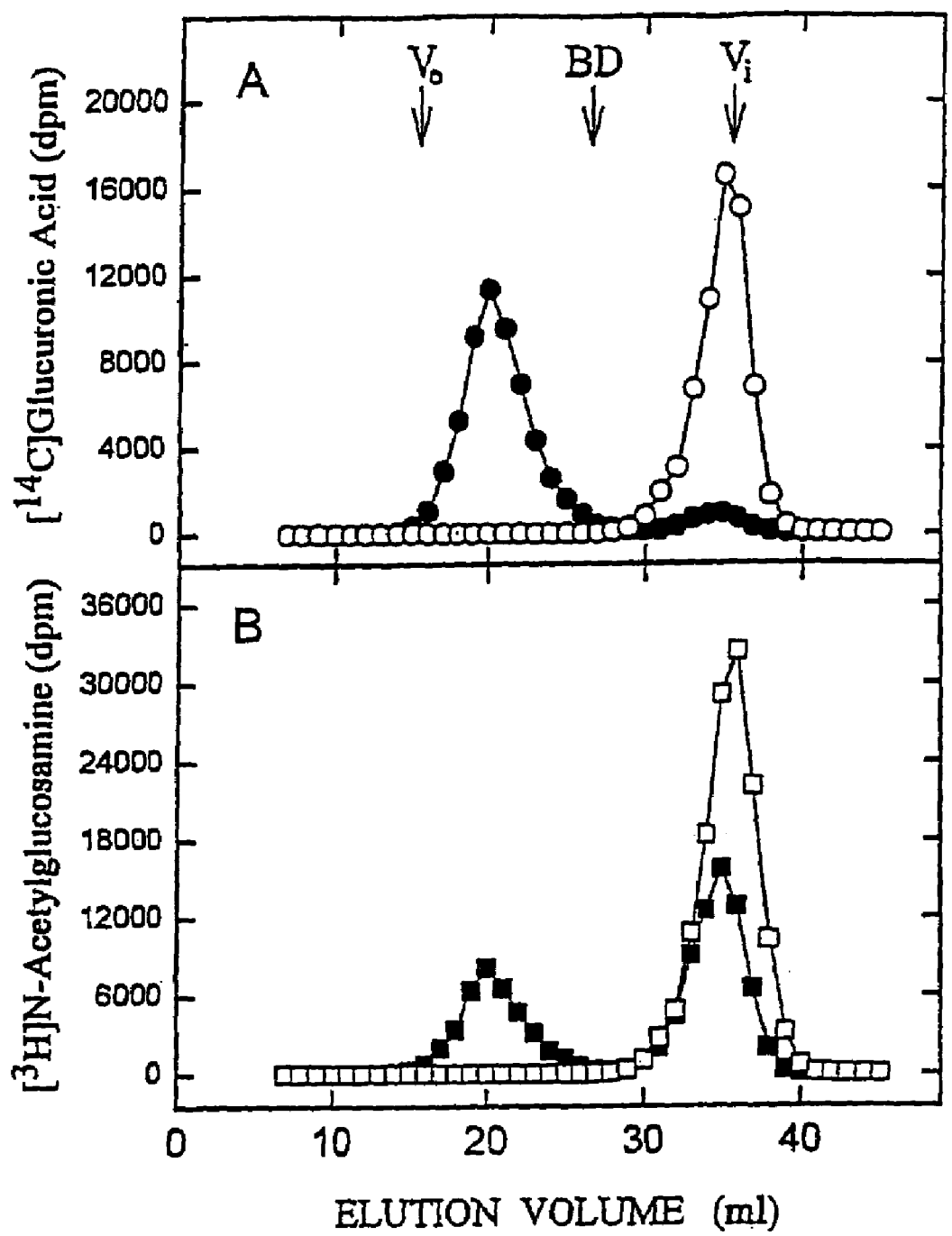

FIG. 13 is a demonstration of the synthesis of authentic HA by the recombinant seHAS.

Figure 14:
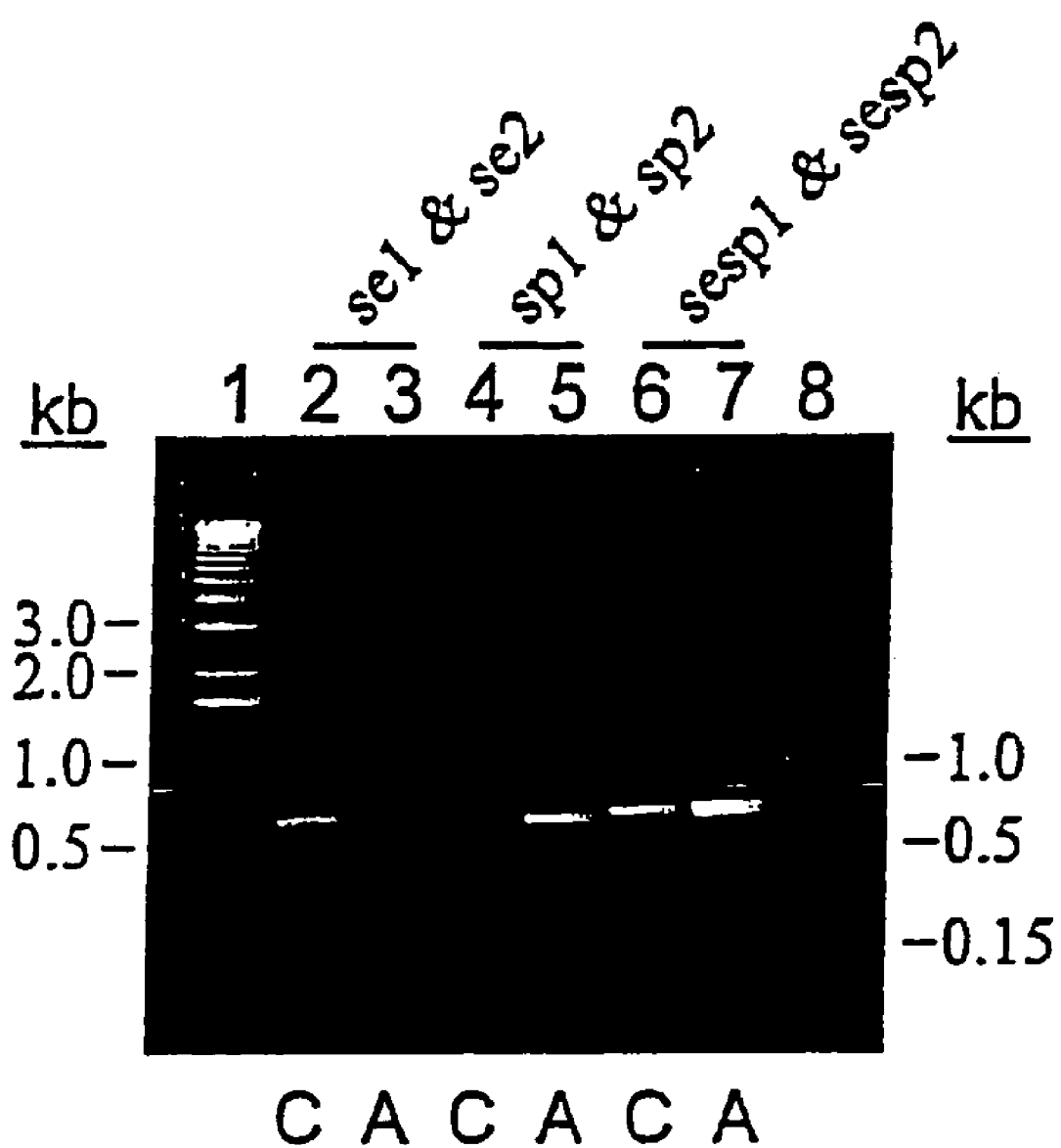

FIG. 14 depicts the recognition of nucleic acid sequences encoding seHAS, encoding spHAS, or encoding both seHAS and spHAS using specific oligonucleotides and PCR.

FIG. 15 depicts oligonucleotides used for specific PCR hybridization.

FIG. 16A is a plot depicting recombinant HA production in live *Bacillus subtilis* by comparing HA production by *Bacillus subtilis* 168 (pSM143 vector alone) to a *Bacillus subtilis* 168 (pSM143 containing seHAS). FIG. 16B is an enlargement of a section of the plot in FIG. 16A.

Figure 17:
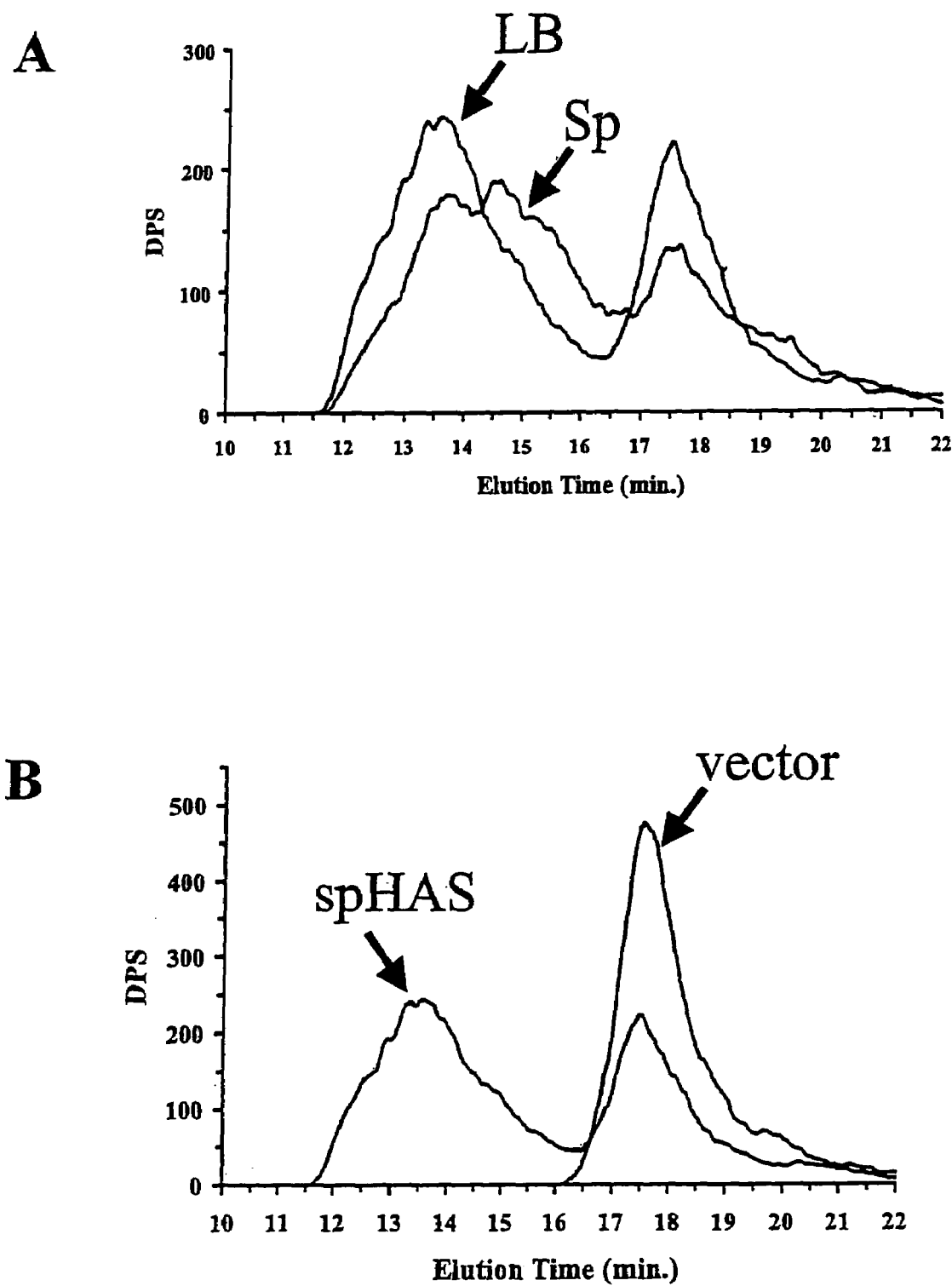

FIG. 17A is a plot depicting nutritional control of recombinant HA size distribution produced by spHAS in live *Bacillus subtilis*.

FIG. 17B is a plot depicting recombinant HA production in live *Bacillus subtilis* 168 compared to *Bacillus subtilis* that contains vector alone.

Figure 18:
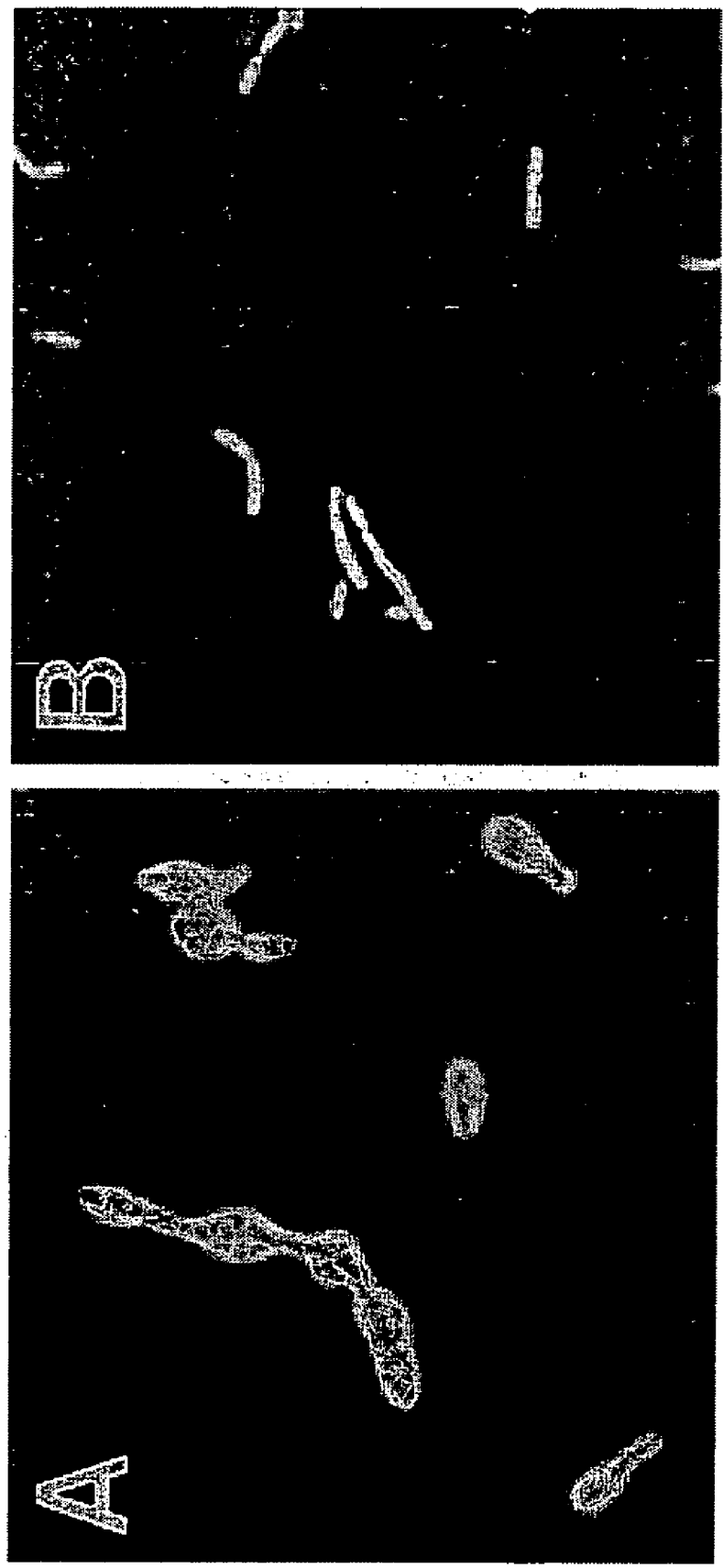

FIGS. 18A and 18B are photomicrographs of recombinant *E. coli*. In FIG. 18A, India ink staining (1,000× magnification) reveals that *E. coli* K5 cells with pPmHAS produce a substantial capsule that appears as a white halo around the cells. In FIG. 18B, the capsular material could be removed from the *E. coli* K5(pPmHAS) cells by brief treatment with *Streptomyces* HA lyase. PmHAS directs polymerization of the HA polysaccharide.

FIG. 19 is a schematic model of GAG biosynthesis in Gram positive and Gram negative bacteria.

Figure 20:
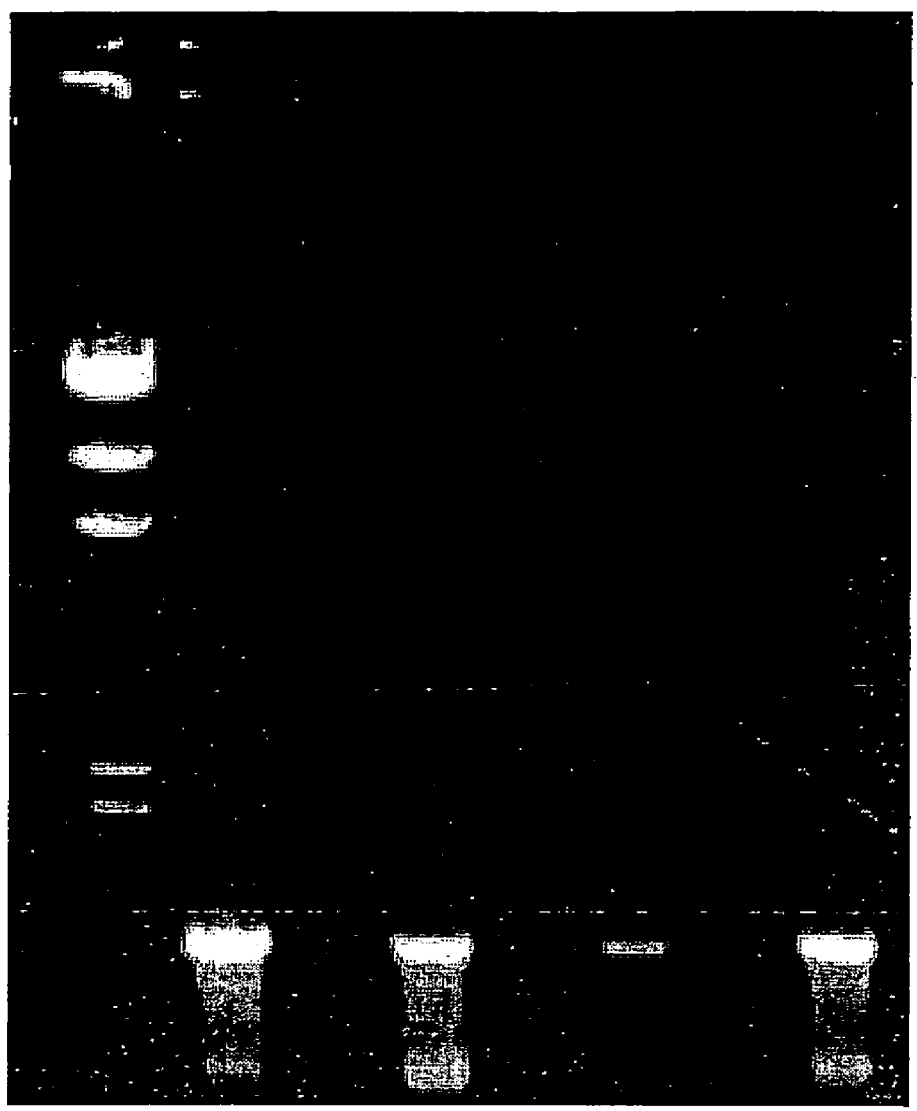

FIG. 20 is an agarose gel demonstrating the PCR amplification of the HAS gene from *Streptococcus uberis*. Genomic DNA was prepared from four separate mucoid colonies of *S. uberis* (lanes 2–5) and subjected to PCR using primers designed to amplify the entire coding region. The 5' (forward) primer, which contains 5' BamHI and pstI restriction enzyme sites (italics), was: AGGATCCGAATTC ATG GAA AAA CTA AAA AAT CTC. The 3' (reverse) primer, which contains 5' EcoRI and pstI sites (italics), was: AGAATTCTGCAG TTA TTT ACT TGT CTT TTT ACG. Reaction products were analyzed by agarose gel electrophoresis, stained with ethidium bromide and a digital image was prepared. In each sample, a band was apparent at the expected size of ~1.25 kb (indicated by the arrow) corresponding to the complete reading frame of suHAS plus the added restriction sites. Lane 1 contains a HindIII digest of lambda DNA as a set of standards or markers.

Figure 21:
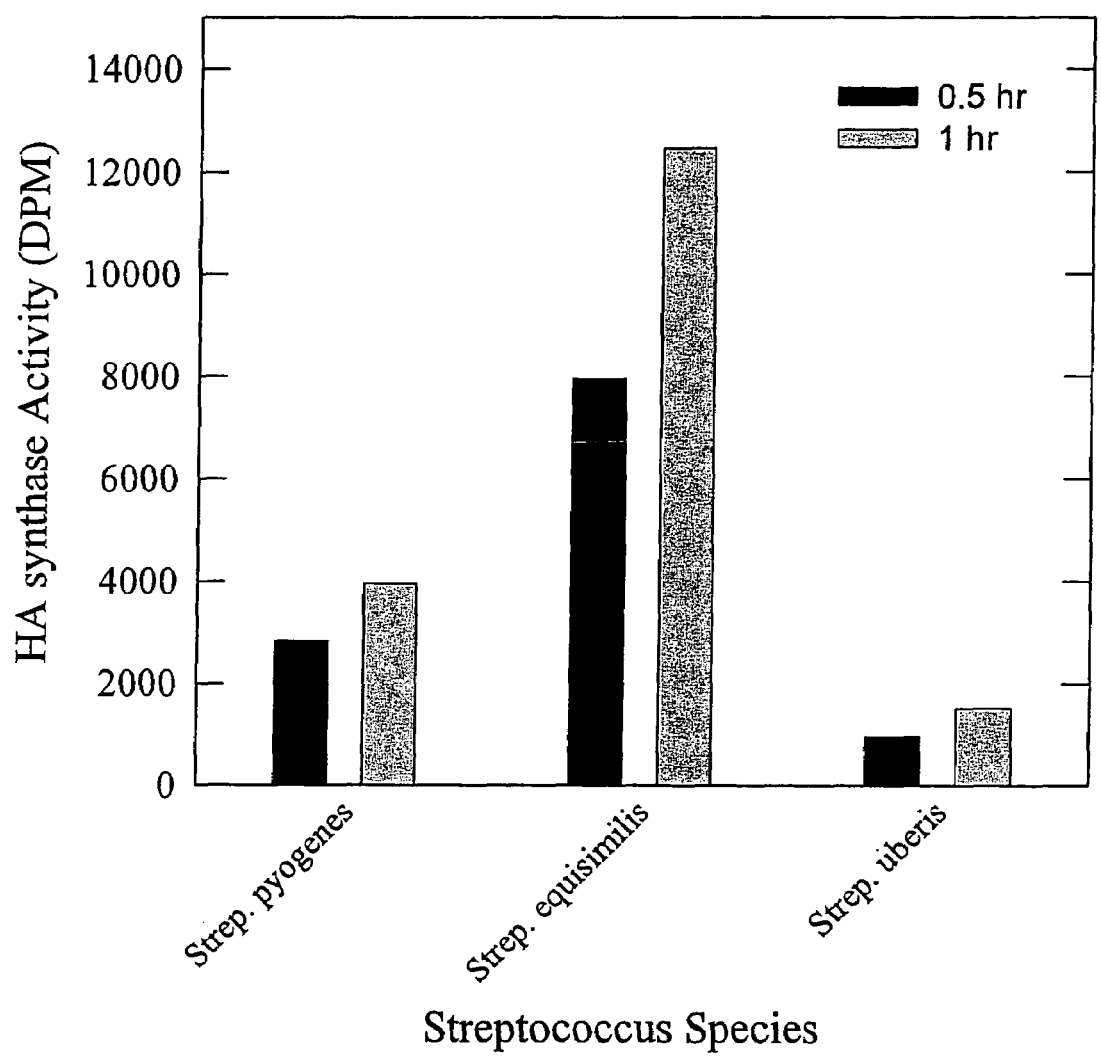

FIG. 21 depicts HA synthase activity from *Streptococcus pyogenes, Streptococcus equisimilis,* and *Streptococcus uberis*. HA synthesis activity was measured (for 5–12 μg membrane protein) by the incorporation of [$^{14}$C]UDP-GlcUA into HA using a paper chromatography assay.

DETAILED DESCRIPTION OF THE INVENTION

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for purpose of description and should not be regarded as limiting.

As used herein, the term "nucleic acid segment" and "DNA segment" are used interchangeably and refer to a DNA molecule which has been isolated free of total genomic DNA of a particular species. Therefore, a "purified" DNA or nucleic acid segment as used herein, refers to a DNA segment which contains a Hyaluronate Synthase ("HAS") coding sequence yet is isolated away from, or purified free from, unrelated genomic DNA of the source cell. Included within the term "DNA segment", are DNA segments and smaller fragments of such segments, and also recombinant vectors, including, for example, plasmids, cosmids, phage, viruses, and the like.

Similarly, a DNA segment comprising an isolated or purified HAS gene refers to a DNA segment including HAS coding sequences isolated substantially away from other naturally occurring genes or protein encoding sequences. In this respect, the term "gene" is used for simplicity to refer to a functional protein, polypeptide or peptide encoding unit. As will be understood by those in the art, this functional term includes genomic sequences, cDNA sequences or combinations thereof. "Isolated substantially away from other coding sequences" means that the gene of interest, in this case HAS, forms the significant part of the coding region of the DNA segment, and that the DNA segment does not contain large portions of naturally-occurring coding DNA, such as large chromosomal fragments or other functional genes or DNA coding regions. Of course, this refers to the DNA segment as originally isolated, and does not exclude genes or coding regions later added to, or intentionally left in the segment by the hand of man.

Due to certain advantages associated with the use of prokaryotic sources, one will likely realize the most advantages upon isolation of the HAS gene from prokaryotes. In particular, one may choose to utilize a Class I or Class II HAS, such as a Class I HAS from *S. equisimilis* or *S. pyogenes*, or a Class II HAS from *P. multocida*.

*Streptococcus* is subdivided taxonomically into Lancefield Groups based on different cell wall carbohydrate antigens. There are 18 distinct groups, but the most common pathogens are A, B, C and D. Historically, the most common pathogens are also often given specific species names, but the unified Lancefield testing method is recognized as being a clear method of typing and thus a useful classification scheme. *Streptococcus* species that may be utilized as the source of the HAS gene include Group A *Streptococcus*, such as *S. pyogenes* and *S. haemolyticus*, and Group C *Streptococcus*, such as *S. equi, S. equisimilis, S. zooepidemicus, S. uberis* and *S. dysgalactiae*.

One such advantage of isolating the HAS gene from prokaryotes is that, typically, eukaryotic enzymes may require significant post-translational modifications that can only be achieved in a eukaryotic host. This will tend to limit the applicability of any eukaryotic HA synthase gene that is obtained. Moreover, those of ordinary skill in the art will likely realize additional advantages in terms of time and ease of genetic manipulation where a prokaryotic enzyme gene is sought to be employed. These additional advantages include (a) the ease of isolation of a prokaryotic gene because of the relatively small size of the genome and, therefore, the reduced amount of screening of the corresponding genomic library, and (b) the ease of manipulation because the overall size of the coding region of a prokaryotic gene is significantly smaller due to the absence of introns. Furthermore, if the product of the HAS gene (i.e., the enzyme) requires posttranslational modifications, these would best be achieved in a similar prokaryotic cellular environment (host) from which the gene was derived.

Preferably, DNA sequences in accordance with the present invention will further include genetic control regions which allow the expression of the sequence in a selected recombinant host. Of course, the nature of the control region employed will generally vary depending on the particular use (e.g., cloning host) envisioned.

In particular embodiments, the invention concerns isolated DNA segments and recombinant vectors incorporating DNA sequences and which encode a HAS gene, that includes within its amino acid sequence an amino acid sequence in accordance with at least one of SEQ ID NOs:2, 10, 12, 14, 16, 18 and 20. Moreover, in other particular embodiments, the invention concerns isolated DNA segments and recombinant vectors incorporating DNA sequences which encode a gene that includes within its amino acid sequence the amino acid sequence of an HAS gene or DNA, and in particular to an HAS gene or cDNA, corresponding to at least one of *Streptococcus equisimilis* HAS, *Streptococcus pyogenes* HAS, *Streptococcus uberis* HAS, *Pasteurella multocida* HAS, *Sulfolobus solfataricus* HAS, *Ectocarpus siliculosus* virus HAS, and *Bacillus anthracis* plasmid pXO1 HAS. For example, where the DNA segment or vector encodes a full length HAS protein, or is intended for use in expressing the HAS protein, preferred sequences are those which are essentially as set forth in at least one of SEQ ID NOs:2, 10, 12, 14, 16, 18 and 20.

Nucleic acid segments having HA synthase activity may be isolated by the methods described herein. The term "a sequence essentially as set forth in SEQ ID NO:X" means that the sequence substantially corresponds to a portion of SEQ ID NO:X and has relatively few amino acids which are not identical to, or a biologically functional equivalent of, the amino acids of SEQ ID NO:X. The term "biologically functional equivalent" is well understood in the art and is further defined in detail herein, as a gene having a sequence essentially as set forth in SEQ ID NO:X, and that is associated with the ability of prokaryotes to produce HA or a hyaluronic acid coat.

Figure 1:
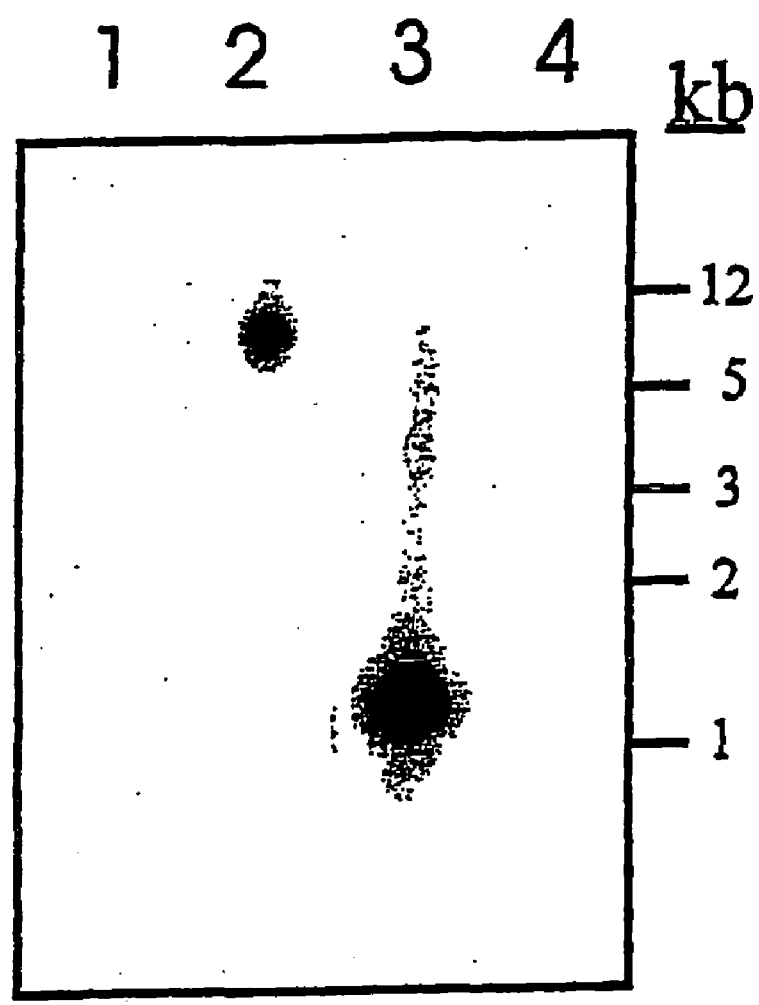

For instance, the seHAS and spHAS coding sequences are approximately 70% identical and rich in the bases adenine (A) and thymine (T). SeHAS base content is A-26.71%, C-19.13%, G-20.81%, and T-33.33% (A/T=60%), whereas spHAS is A-31.34%, C-16.42%, G-16.34%, and T-35.8% (A/T=67%). Those of ordinary skill in the art would be surprised that the seHAS coding sequence does not hybridize with the spHAS gene and vice versa, despite their being 70% identical. This unexpected inability to cross-hybridize could be due to short interruptions of mismatched bases throughout the open reading frames. The inability of spHAS and seHAS to cross-hybridize is shown in FIG. 1. The longest stretch of identical nucleotides common to both the seHAS and the spHAS coding sequences is only 20 nucleotides. In addition, the very A-T rich sequences will form less stable hybridization complexes than G-C rich sequences. Another possible explanation could be that there are several stretches of As or Ts in both sequences that could hybridize in a misaligned and unstable manner. This would put the seHAS and spHAS gene sequences out of frame with respect to each other, thereby decreasing the probability of productive hybridization.

Because of this unique phenomena of two genes encoding proteins which are 70% identical not being capable of cross-hybridizing to one another, it is beneficial to think of the claimed nucleic acid segment in terms of its function; i.e., a nucleic acid segment which encodes enzymatically active hyaluronate synthase. One of ordinary skill in the art would appreciate that a nucleic acid segment encoding enzymatically active hyaluronate synthase may contain conserved or semi-conserved substitutions to the sequences set forth in SEQ ID NOS: 1, 2 and 9–20 and yet still be within the scope of the invention.

In particular, the art is replete with examples of practitioners ability to make structural changes to a nucleic acid segment (i.e., encoding conserved or semi-conserved amino acid substitutions) and still preserve its enzymatic or functional activity. See for example: (1) Risler et al. "Amino Acid Substitutions in Structurally Related Proteins. A Pattern Recognition Approach." J. Mol. Biol. 204:1019–1029 (1988) [" . . . according to the observed exchangeability of amino acid side chains, only four groups could be delineated; (I) Ile and Val; (ii) Leu and Met, (iii) Lys, Arg, and Gln, and (iv) Tyr and Phe."]; (2) Niefind et al. "Amino Acid Similarity Coefficients for Protein Modeling and Sequence Alignment Derived from Main-Chain Folding Anoles." J. Mol. Biol. 219:481–497 (1991) [similarity parameters allow amino acid substitutions to be designed]; and (3) Overington et al. "Environment-Specific Amino Acid Substitution Tables: Tertiary Templates and Prediction of Protein Folds," Protein Science 1:216–226 (1992) ["Analysis of the pattern of observed substitutions as a function of local environment shows that there are distinct patterns . . . " Compatible changes can be made.], the contents of each being expressly incorporated herein by reference in their entirety.

These references and countless others indicate that one of ordinary skill in the art, given a nucleic acid sequence, could make substitutions and changes to the nucleic acid sequence without changing its functionality. Also, a substituted nucleic acid segment may be highly identical and retain its enzymatic activity with regard to its unadulterated parent, and yet still fail to hybridize thereto.

The invention discloses nucleic acid segments encoding enzymatically active hyaluronate synthases, such as seHAS, spHAS, suHAS and pmHAS. Although seHAS and spHAS are 70% identical and both encode enzymatically active hyaluronate synthase, they do not cross hybridize. Thus, one of ordinary skill in the art would appreciate that substitutions can be made to the seHAS nucleic acid segment listed in SEQ ID NO: 1 without deviating outside the scope and claims of the present invention. Standardized and accepted functionally equivalent amino acid substitutions are presented in Table I.

TABLE I

| Amino Acid Group | Conservative and Semi-Conservative Substitutions |
| --- | --- |
| NonPolar R Groups | Alanine, Valine, Leucine, Isoleucine, Proline, Methionine, Phenylalanine, Tryptophan |
| Polar, but uncharged, R Groups | Glycine, Serine, Threonine, Cysteine, Asparagine, Glutamine |
| Negatively Charged R Groups | Aspartic Acid, Glutamic Acid |
| Positively Charged R Groups | Lysine, Arginine, Histidine |

Another preferred embodiment of the present invention is a purified nucleic acid segment that encodes a protein in accordance with SEQ ID NOs:2, 10, 12, 14, 16, 18 or 20 further defined as a recombinant vector. As used herein, the term "recombinant vector" refers to a vector that has been modified to contain a nucleic acid segment that encodes an HAS protein, or fragment thereof. The recombinant vector may be further defined as an expression vector comprising a promoter operatively linked to said HAS encoding nucleic acid segment.

A further preferred embodiment of the present invention is a host cell, made recombinant with a recombinant vector comprising an HAS gene. The preferred recombinant host cell may be a prokaryotic cell. In another embodiment, the recombinant host cell is a eukaryotic cell. As used herein, the term "engineered" or "recombinant" cell is intended to refer to a cell into which a recombinant gene, such as a gene encoding HAS, has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene, a copy of a genomic gene, or will include genes positioned adjacent to a promoter not naturally associated with the particular introduced gene.

Where one desires to use a host other than *Streptococcus*, as may be used to produce recombinant HA synthase, it may be advantageous to employ a prokaryotic system such as *E. coli*, *Bacillus* strains, *Lactococcus* sp., or even eukaryotic systems such as yeast or Chinese hamster ovary, African green monkey kidney cells, VERO cells, or the like. Of course, where this is undertaken it will generally be desirable to bring the HA synthase gene under the control of sequences which are functional in the selected alternative host. The appropriate DNA control sequences, as well as their construction and use, are generally well known in the art as discussed in more detail hereinbelow. For example, in a preferred embodiment, the host cell may be a *Bacillus* cell, such as a *Bacillus subtilis* or *Bacillus licheniformis* cell, and the vector introduced therein contains a *Bacillus*-compatible promoter to which the has gene is operably linked.

In a more preferred embodiment, the host cell is a *Bacillus* cell, such as *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus metaterium, Bacillus pumilus, Bacillus stearothermophilus, Bacillus subtilis* and *Bacillus thuringienisis*.

In preferred embodiments, the HA synthase-encoding DNA segments further include DNA sequences, known in the art functionally as origins of replication or "replicons", which allow replication of contiguous sequences by the particular host. Such origins allow the preparation of extrachromosomally localized and replicating chimeric segments or plasmids, to which HA synthase DNA sequences are ligated. In more preferred instances, the employed origin is one capable of replication in bacterial hosts suitable for biotechnology applications. However, for more versatility of cloned DNA segments, it may be desirable to alternatively or even additionally employ origins recognized by other host systems whose use is contemplated (such as in a shuttle vector).

The isolation and use of other replication origins such as the SV40, polyoma or bovine papilloma virus origins, which may be employed for cloning or expression in a number of higher organisms, are well known to those of ordinary skill in the art. In certain embodiments, the invention may thus be defined in terms of a recombinant transformation vector which includes the HA synthase coding gene sequence together with an appropriate replication origin and under the control of selected control regions.

Thus, it will be appreciated by those of skill in the art that other means may be used to obtain the HAS gene or cDNA, in light of the present disclosure. For example, polymerase chain reaction or RT-PCR produced DNA fragments may be obtained which contain full complements of genes or cDNAs from a number of sources, including other strains of *Streptococcus*, or from eukaryotic sources, such as cDNA libraries. Virtually any molecular cloning approach may be employed for the generation of DNA fragments in accordance with the present invention. Thus, the only limitation generally on the particular method employed for DNA isolation is that the isolated nucleic acids should encode a biologically functional equivalent HA synthase.

Once the DNA has been isolated, it is ligated together with a selected vector. Virtually any cloning vector can be employed to realize advantages in accordance with the invention. Typical useful vectors include plasmids and phages for use in prokaryotic organisms and even viral vectors for use in eukaryotic organisms. Examples include pKK223-3, pSA3, recombinant lambda, SV40, polyoma, adenovirus, bovine papilloma virus and retroviruses. However, it is believed that particular advantages will ultimately be realized where vectors capable of replication in both *Lactococcus* or *Bacillus* strains and *E. coli* are employed.

Vectors such as these, exemplified by the pSA3 vector of Dao and Ferretti or the pAT19 vector of Trieu-Cuot, et al., allow one to perform clonal colony selection in an easily manipulated host such as *E. coli*, followed by subsequent transfer back into a food grade *Lactococcus* or *Bacillus* strain for production of HA. These are benign and well studied organisms used in the production of certain foods and biotechnology products. These are advantageous in that one can augment the *Lactococcus* or *Bacillus* strain's ability to synthesize HA through gene dosaging (i.e., providing extra copies of the HA synthase gene by amplification) and/or inclusion of additional genes to increase the availability of HA precursors. The inherent ability of a bacterium to synthesize HA can also be augmented through the formation of extra copies, or amplification, of the plasmid that carries the HA synthase gene. This amplification can account for up to a 10-fold increase in plasmid copy number and therefore the HA synthase gene copy number.

Another procedure that would further augment HA synthase gene copy number is the insertion of multiple copies of the gene into the plasmid. Another technique would include integrating the HAS gene into chromosomal DNA. This extra amplification would be especially feasible, since the bacterial HA synthase gene size is small. In some scenarios, the chromosomal DNA-ligated vector is employed to transfect the host that is selected for clonal screening purposes such as E. coli, through the use of a vector that is capable of expressing the inserted DNA in the chosen host.

In another preferred embodiment, the HA synthase gene is introduced into the host cell chromosome via homologous or heterologous recombination. The has gene may be more stable in this configuration, especially without drug selection. Various vectors may be employed to introduce the has gene into Bacillus, such as pTLH or pKSV7, or into yeast, such as YIp211, or into animal cells, such as pcDNA/FRT. The DNA is first introduced into the host cell by transformation, transduction or electroporation. The DNA segment with the has gene is then stably integrated into the host chromosome. For example, the spHAS gene was used to repair a mutant Streptococcus chromosome by transduction and integration; this operation resulted in HA production (DeAngelis et al., 1993).

Where a eukaryotic source such as dermal or synovial fibroblasts or rooster comb cells is employed, one will desire to proceed initially by preparing a cDNA library. This is carried out first by isolation of mRNA from the above cells, followed by preparation of double stranded cDNA using an enzyme with reverse transcriptase activity and ligation with the selected vector. Numerous possibilities are available and known in the art for the preparation of the double stranded cDNA, and all such techniques are believed to be applicable. A preferred technique involves reverse transcription. Once a population of double stranded cDNAs is obtained, a cDNA library is prepared in the selected host by accepted techniques, such as by ligation into the appropriate vector and amplification in the appropriate host. Due to the high number of clones that are obtained, and the relative ease of screening large numbers of clones by the techniques set forth herein, one may desire to employ phage expression vectors, such as λgt11, λgt12, λGem11, and/or λZAP for the cloning and expression screening of cDNA clones.

In certain other embodiments, the invention concerns isolated DNA segments and recombinant vectors that include within their sequence a nucleic acid sequence essentially as set forth at least one of in SEQ ID NOS:1, 9, 11, 13, 15, 17 and 19. The term "essentially as set forth in SEQ ID NO:1", for example, is used in the same sense as described above and means that the nucleic acid sequence substantially corresponds to a portion of SEQ ID NO:1, and has relatively few codons which are not identical, or functionally equivalent, to the codons of SEQ ID NO:1. The term "functionally equivalent codon" is used herein to refer to codons that encode the same amino acid, such as the six codons for arginine or serine, and also refers to codons that encode biologically equivalent amino acids as set forth in Table I.

It will also be understood that amino acid and nucleic acid sequences may include additional residues, such as additional N- or C-terminal amino acids or additional 5' or 3' nucleic acid sequences, and yet still be essentially as set forth in one of the sequences disclosed herein, so long as the sequence meets the criteria set forth above, including the maintenance of biological protein activity where protein expression and enzyme activity are concerned. The addition of terminal sequences particularly applies to nucleic acid sequences which may, for example, include various non-coding sequences flanking either of the 5' or 3' portions of the coding region or may include various internal sequences, which are known to occur within genes. In particular, the amino acid sequence of the has gene product in eukaryotes appears to be 40% larger than that found in prokaryotes.

Allowing for the degeneracy of the genetic code as well as conserved and semi-conserved substitutions, sequences which have between about 40% and about 80%; or more preferably, between about 80% and about 90%; or even more preferably, between about 90% and about 99%; of nucleotides which are identical to the nucleotides of SEQ ID NOS:1, 9, 11, 13, 15, 17 or 19 will be sequences which are "essentially as set forth in SEQ ID NOS:1, 9, 11, 13, 15, 17 or 19". Sequences which are essentially the same as those set forth in SEQ ID NOS:1, 9, 11, 13, 15, 17 or 19 may also be functionally defined as sequences which are capable of hybridizing to a nucleic acid segment containing the complement of SEQ ID NOS:1, 9, 11, 13, 15, 17 or 19 under standard or less stringent hybridizing conditions. Suitable standard hybridization conditions will be well known to those of skill in the art and are clearly set forth herein.

The term "standard hybridization conditions" as used herein, is used to describe those conditions under which substantially complementary nucleic acid segments will form standard Watson-Crick base-pairing. A number of factors are known that determine the specificity of binding or hybridization, such as pH, temperature, salt concentration, the presence of agents, such as formamide and dimethyl sulfoxide, the length of the segments that are hybridizing, and the like. When it is contemplated that shorter nucleic acid segments will be used for hybridization, for example fragments between about 14 and about 100 nucleotides, salt and temperature preferred conditions for hybridization will include 1.2–1.8× High Phosphate Buffer (HPB) at 40–50° C.

Naturally, the present invention also encompasses DNA segments which are complementary, or essentially complementary, to the sequence set forth in SEQ ID NOS:1, 9, 11, 13, 15, 17 or 19. Nucleic acid sequences which are "complementary" are those which are capable of base-pairing according to the standard Watson-Crick complementarity rules. As used herein, the term "complementary sequences" means nucleic acid sequences which are substantially complementary, as may be assessed by the same nucleotide comparison set forth above, or as defined as being capable of hybridizing to the nucleic acid segment of SEQ ID NOS:1, 9, 11, 13, 15, 17 or 19.

The nucleic acid segments of the present invention, regardless of the length of the coding sequence itself, may be combined with other DNA sequences, such as promoters, polyadenylation signals, additional restriction enzyme sites, multiple cloning sites, epitope tags, poly histidine regions, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

Naturally, it will also be understood that this invention is not limited to the particular nucleic acid and amino acid sequences of SEQ ID NOS:1, 9, 11, 13, 15, 17 and 19 and SEQ ID NOS:2, 10, 12, 14, 16, 18 and 20, respectively. Recombinant vectors and isolated DNA segments may therefore variously include the HAS coding regions themselves, coding regions bearing selected alterations or modifications in the basic coding region, or they may encode larger polypeptides which nevertheless include HAS-coding regions or may encode biologically functional equivalent proteins or peptides which have variant amino acids sequences.

The capsule of Carter Type A *P. multocida* was long suspected of containing hyaluronic acid (HA). Characterization of the HA synthase of *P. multocida* led to interesting enzymological differences between it and the seHAS and spHAS proteins.

*P. multocida* cells produce a readily visible extracellular HA capsule, and since the two streptococcal HASs are membrane proteins, membrane preparations of the fowl cholera pathogen were tested. In early trials, crude membrane fractions derived from ultrasonication alone possessed very low levels of UDP-GlcNAc-dependent UDP-[$^{14}$C]GlcUA incorporation into HA[~0.2 pmol of GlcUA transfer (μg of proteins)$^{-1}$h$^{-1}$] when assayed under conditions similar to those for measuring streptococcal HAS activity. The enzyme from *E. coli* with the recombinant hasA plasmid was also recalcitrant to isolation at first. These results were in contrast to the easily detectable amounts obtained from *Streptococcus* by similar methods.

An alternative preparation protocol using ice-cold lysozyme treatment in the presence of protease inhibitors in conjunction with ultrasonication allowed the substantial recovery of HAS activity from both species of Gram-negative bacteria. Specific activities for HAS of 5–10 pmol of GlcUA transferred (μg of protein)$^{-1}$h$^{-31\ 1}$ were routinely obtained for crude membranes of wild-type *P. multocida* with the new method. In the absence of UDP-GlcNAc, virtually no radioactivity (<1% of identical assay with both sugar precursors) from UDP-[$^{14}$C]GlcUA was incorporated into higher molecular weight material. Membranes prepared from the acapsular mutant, TnA, possessed no detectable HAS activity when supplemented with both sugar nucleotide precursors (data not shown). Gel-filtration analysis using a Sephacryl S-200 column indicates that the molecular mass of the majority of the $^{14}$C-labeled product synthesized in vitro is ≧8×10$^4$ Da since the material elutes in the void volumes, such a value corresponds to a HA molecule composed of at least 400 monomers. This product is sensitive to *Streptomyces* hyaluronidase digestion but resistant to protease treatment.

The parameters of the HAS assay were varied to maximize incorporation of UDP-sugars into polysaccharide by *P. multocida* membranes. Streptococcal spHAS requires $Mg^{2+}$, and therefore this metal ion was included in the initial assays of *P. multocida* membranes. The *P. multocida* HAS (pmHAS) was relatively active from pH 6.5 to 8.6 in Tris-type buffers with an optimum at pH 7. The HAS activity was linear with respect to the incubation time at neutral pH for at least 1 h. The pmHAS was apparently less active at higher ionic strengths because the addition of 100 mM NaCl to the reaction containing 50 mM Tris, pH 7, and 20 mM $MgCl_2$ reduced sugar incorporation by ~50%.

The metal ion specificity of the pmHAS was assessed at pH 7. Under metal-free conditions in the presence of EDTA, no incorporation of radiolabeled precursor into polysaccharide was detectable (<0.5% of maximal signal). $Mn^{2+}$ gave the highest incorporation rates at the lowest ion concentrations for the tested metals (Mg, Mn, Co, Cu, and Ni). $Mg^{2+}$ gave about 50% of the $Mn^{2+}$ stimulation but at 10-fold higher concentrations. $Co^{2+}$ or $Ni^{2+}$ at 10 mM supported lower levels of activity (20% or 9%, respectively, of 1 mM $Mn^{2+}$ assays), but membranes supplied with 10 mM $Cu^{2+}$ were inactive. Indeed, mixing 10 mM $Cu^{2+}$ and 20 mM$^{2+}$ Mg2$^+$ with the membrane preparation resulted in almost no incorporation of label into polysaccharide (<0.8% of Mg only value).

Initial characterization of the pmHAS was performed in the presence of $Mg^{2+}$. The binding affinity of the enzyme for its sugar nucleotide precursors was assessed by measuring the apparent $K_M$ value. Incorporation of [$^{14}$C]GlcUA or [$^3$H]GlcNAc into polysaccharide was monitored at varied concentrations of UDP-GlcNAc or UDP-GlcUA, respectively. In $Mg^{2+}$-containing buffers, the apparent $K_M$ values of ~20 μM for UDP-GlcUA and ~75 μM for UDP-GlcNAc were determined utilizing Hanes-Woolf plots ([S]/v versus [S]) of the titration data. The $V_{max}$ values for both sugars were the same because the slopes, corresponding to $1/V_{max}$, of the Hanes-Woolf plots were equivalent. In comparison to results from assays with $Mg^{2+}$, the $K_M$ value for UDP-GlcNAc was increased by about 25–50% to ~105 μM and the $V_{max}$ increased by a factor of 2–3-fold in the presence of $Mn^{2+}$.

The HA synthase enzymes from either *P. multocida, S. equisimilis,* or *S. pyogenes* utilizes UDP-sugars, but they possess somewhat different kinetic optima with respect to pH and metal ion dependence and $K_M$ values. The enzymes are most active at pH 7; however, the pmHAS reportedly displays more activity at slightly acidic pH and is relatively inactive above pH 7.4. The pmHAS utilizes $Mn^{2+}$ more efficiently than $Mg^{2+}$ under the in vitro assay conditions, but the identity of the physiological metal cofactor in the bacterial cell is unknown. In comparison, in previous studies with the streptococcal enzyme, $Mg^{2+}$ was much better than $Mn^{2+}$ but the albeit smaller effect of $Mn^{2+}$ was maximal at ~10-fold lower concentrations than the optimal $Mg^{2+}$ concentration. The pmHAS apparently binds the UDP-sugars more tightly than spHAS. The measured $K_M$ values for the pmHAS in crude membranes are about 2–3-fold lower for each substrate than those obtained from the HAS found in streptococcal membranes: 50 or 39 μM for UDP-GlcUA and 500 or 150 μM for UDP-GlcNAc, respectively.

By kinetic analyses, the $V_{max}$ of the pmHAS was 2–3-fold higher in the presence of $Mn^{2+}$ than $Mg^{2+}$, but the UDP-GlcNAc $K_M$ value was increased slightly in assays with the former ion. This observation of apparent lowered affinity suggests that the increased polymerization rate was not due to better binding of the $Mn^{2+}$ ion/sugar nucleotide complex to the enzyme active site(s). Therefore, it is possible that $Mn^{2+}$ enhances some other reaction step, alters another site/structure of the enzyme, or modifies the phospholipid membrane environment. The gene sequence and the protein sequence of pmHAS are shown in SEQ ID NOS:9 and 10, respectively.

Chlorella virus PBCV-1 encodes a functional glycosyltransferase that can synthesize hyaluronan. This finding is contrary to the general observation that viruses either: (a) utilize host cell glycosyltransferases to create new carbohydrate structures, or (b) accumulate host cell glycoconjugates during virion maturation. Furthermore, HA has been generally regarded as restricted to animals and a few of their virulent bacterial pathogens. Though many plant carbohydrates have been characterized, neither HA nor a related analog has previously been detected in cells of plants or protists.

The vertebrate, bacterial and viral HAS enzymes have several regions of sequence similarity. While sequencing the double-stranded DNA genome of virus PBCV-1 [*Paramecium bursaria* Chlorella virus], an ORF [open reading frame], A98R (Accession #442580), encoding a 567 residue protein with 28 to 33% amino acid identity to the various HASs was discovered. This protein is designated cvHAS (Chlorella virus HA synthase). The gene sequence encoding PBCV-1 and the protein sequence it encodes are shown in SEQ ID NOS:7 and 8, respectively.

PBCV-1 is the prototype of a family (Phycodnarviridae) of large (175–190 nm diameter) polyhedral, plaque-forming viruses that replicate in certain unicellular, eukaryotic chlorella-like green algae. PBCV-1 virions contain at least 50 different proteins and a lipid component located inside the outer glycoprotein capsid. The PBCV-1 genome is a linear, nonpermuted 330-kb dsDNA molecule with covalently closed hairpin ends.

Based on its deduced amino acid sequence, the A98R gene product should be an integral membrane protein. To test this hypothesis, recombinant A98R was produced in *Escherichia coli* and the membrane fraction was assayed for HAS activity. UDP-GlcUA and UDP-GlcNAc were incorporated into the polysaccharide by the membrane fraction derived from cells containing the A98R gene on a plasmid, pCVHAS, (average specific activity 2.5 pmoles GlcUA transfer/µg protein/min) but not by samples from control cells (<0.001 pmoles GlcUA transfer/µg protein/min). No activity was detected in the soluble fraction of cells transformed with pCVHAS. UDP-GlcUA and UDP-GlcNAc were simultaneously required for polymerization. The activity was optimal in Hepes buffer at pH 7.2 in the presence of 10 mM $MnCl_2$, whereas no activity was detected if the metal ion was omitted. $Mg^{2+}$ and $Co^{2+}$ were ~20% as effective as $Mn^{2+}$ at similar concentrations. The pmHAS has a similar metal requirement, but other HASs prefer $Mg^{2+}$.

The recombinant A98R enzyme synthesized a polysaccharide with an average molecular weight of $3-6\times10^6$ Da which is smaller than that of the HA synthesized by recombinant spHAS or DG42 xlHAS in vitro (~$10^7$ Da and ~$5-8\times10^6$ Da, respectively). The polysaccharide was completely degraded by *Streptomyces hyaluroniticus* HA lyase, an enzyme that depolymerizes HA, but not structurally related glycosaminoglycans such as heparin and chondroitin.

PBCV-1 infected Chlorella cells were examined for A98R gene expression. A ~1,700-nucleotide A98R transcript appeared at ~15 min post-infection and disappeared by 60 min after infection indicating that A98R is an early gene. Consequently, membrane fractions from uninfected and PBCV-1 infected chlorella cells were assayed at 50 and 90 min post-infection for HAS activity. Infected cells, but not uninfected cells, had activity. Like the bacterially derived recombinant A98R enzyme, radiolabel incorporation from UDP-[$^{14}$C]GlcUA into polysaccharide depended on both $Mn^{2+}$ and UDP-GlcNAc. This radiolabeled product was also degraded by HA lyase. Disrupted PBCV-1 virions had no HAS activity.

PBCV-1 infected Chlorella cells were analyzed for HA polysaccharide using a highly specific $^{125}$I-labeled HA-binding protein. Extracts from cells at 50 and 90 min post-infection contained substantial amounts of HA, but not extracts from uninfected algae or disrupted PBCV-1 virions. The labeled HA-binding protein also interacted with intact infected cells at 50 and 90 min post-infection, but not healthy cells. Therefore, a considerable portion of the newly synthesized HA polysaccharide was immobilized at the outer cell surface of the infected algae. The extracellular HA does not play any obvious role in the interaction between the virus and its algal host because neither plaque size nor plaque number was altered by including either testicular hyaluronidase (465 units/ml) or free HA polysaccharide (100 µg/ml) in the top agar of the PBCV-1 plaque assay.

The PBCV-1 genome also has additional genes that encode for an UDP-glucose dehydrogenase (UDP-Glc DH) and a glutamine:fructose-6-phosphate aminotransferase (GFAT). UDP-Glc DH converts UDP-Glc into UDP-GlcUA, a required precursor for HA biosynthesis. GFAT converts fructose-6-phosphate into glucosamine-6-phosphate, an intermediate in the UDP-GlcNAc metabolic pathway. Both of these PBCV-1 genes, like the A98R HAS, are expressed early in infection and encode enzymatically active proteins. The presence of multiple enzymes in the HA biosynthesis pathway indicates that HA production must serve an important function in the life cycle of the Chlorella viruses.

HA synthases of *Streptococcus*, vertebrates, and PBCV-1 possess many motifs of a pattern of at least 2 to 4 identical residues that occur in the same relative order. These conserved motifs probably reflect domains crucial for HA biosynthesis as shown in FIG. 2. FIG. 2 is an alignment of the protein sequences of Group C seHAS and suHAS from *S. equisimilis* and *S. uberis*, respectively; Group A spHAS from *S. pyogenes;* the mouse isozymes mHAS1, mHAS2 and mHAS3; the human isozymes hHAS1, hAS2 and hHAS3; the frog isozymes x1HAS1 and x1HAS2; the original PBCV-1 virus HAS, cvHAS, as well as the newer viral HASs vNC, vMA, vAL and vCA; the rat rnHAS2; the chicken ggHAS2; the bovine btHAS2; and the rabbit isozymes ocHAS2 and ocHAS3. The alignment of FIG. 2 was accomplished using the Mutalin version 5.4.1 multiple alignment program (copyright I.N.R.A. France 1989, 1991, 1994, 1996; Multiple sequence alignment with hierarchical clustering, Corpet, *Nucl. Acids Res.,* 16:10881 (1988)). A consensus line is provided on the lower line of the alignment. Capital letters in the consensus line represent identical residues in all HAS proteins listed, while lower case letters represent consensus residues that are not identical in all cases. The consensus line also contains the following symbols: ! is any one of I, V; $ is any one of L, M; % is any one of F, Y; # is any one of N, D, Q, E, B, Z. The symbol comparison table was blosum62, the gap weight was 12, and the gap length weight was 2.

Regions of similarity between HASs and other enzymes that synthesize β-linked polysaccharides from UDP-sugar precursors are also being discovered as more glycosyltransferases are sequenced. Examples include bacterial cellulose synthase, fungal and bacterial chitin synthases, and the various HASs. The significance of these similar structural motifs will become more apparent as the three-dimensional structures of glycosyltransferases accumulate.

Figure 3:
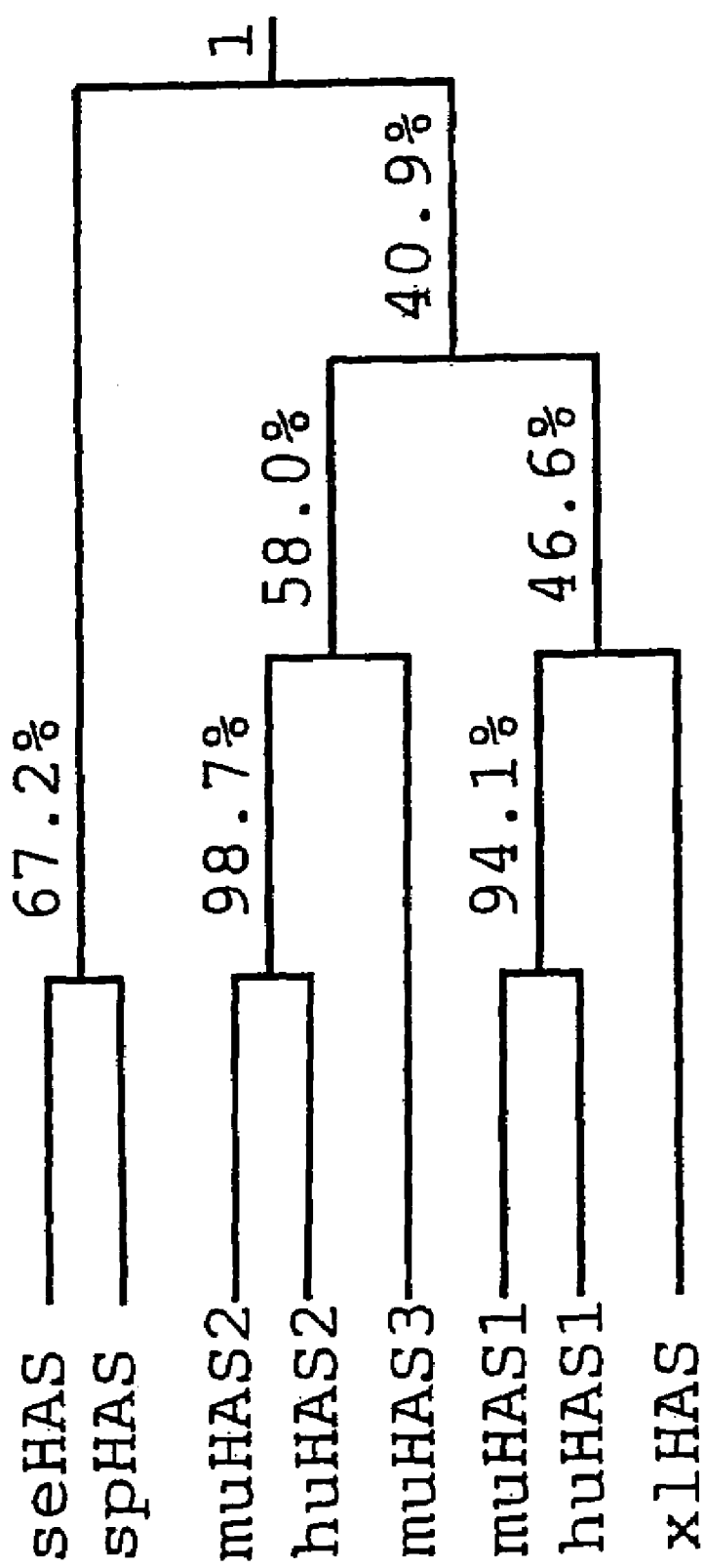

FIG. 3 depicts the possible evolutionary relationships among the known hyaluronan synthases. The phylogenetic tree of FIG. 3 was generated by the Higgins-Sharp algorithm using the DNAsis multiple alignment program. The calculated matching percentages are indicated at each branch of the dendrogram.

The DNA segments of the present invention encompass biologically functional equivalent HAS proteins and peptides. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the enzyme activity or to antigenicity of the HAS protein or to test HAS mutants in order to examine HA synthase activity at the molecular level.

Also, specific changes to the HAS coding sequence can result in the production of HA having a modified size distribution or structural configuration. One of ordinary skill in the art would appreciate that the HAS coding sequence can be manipulated in a manner to produce an altered hyaluronate synthase which in turn is capable of producing hyaluronic acid having differing polymer sizes and/or functional capabilities. For example, the HAS coding sequence may be altered in such a manner that the hyaluronate synthase has an altered sugar substrate specificity so that the hyaluronate synthase creates a new hyaluronic acid-like polymer incorporating a different structure such as a previously unincorporated sugar or sugar derivative. This newly incorporated sugar could result in a modified hyaluronic acid having different functional properties, a hyaluronic acid having a smaller or larger polymer size/molecular weight, or both. As will be appreciated by one of ordinary skill in the art given the HAS coding sequences, changes and/or substitutions can be made to the HAS coding sequence such that these desired property and/or size modifications can be accomplished. Table II lists sugar nucleotide specificity and magnesium ion requirement of recombinant seHAS.

TABLE II

Sugar nucleotide specificity and Magnesium ion requirement of recombinant seHAS

| Second Sugar nucleotide present (µM) | UDP-[$^{14}$C]GlcUA dpm (%) | HA Synthesis* UDP-[$^{3}$H]GlcNAc dpm (%) |
|---|---|---|
| None | 90 (2.1%) | 8 (1.2%) |
| UDP-GlcNAc (300) | 4134 (100%) | — |
| UDP-GlcUA (120) | — | 635 (100%) |
| UDP-Glc (160) | 81 (1.9%) | 10 (1.5%) |
| UDP-GalNAc (280) | 74 (1.7%) | 19 (2.9%) |
| UDP-GalA (150) | 58 (1.4%) | 19 (2.9%) |
| UDP-GlcNAc + EDTA | 31 (0.7%) | — |
| UDP-GlcUA + EDTA | — | 22 (3.4%) |

*Membranes (324 ng protein) were incubated at 37° C. for 1 h with either 120 µM UDP-[$^{14}$C] GlcUA (2.8 × 10$^4$ dpm) or 300 µM UDP-[$^3$H]GlcNAc (2 × 10$^4$ dpm). The radiolabeled sugar nucleotide was used in the presence of the indicated second nonlabeled sugar nucleotide. HA synthase activity was determined as described in the application.

The term "modified structure" as used herein denotes a hyaluronic acid polymer containing a sugar or derivative not normally found in the naturally occurring HA polysaccharide. The term "modified size distribution" refer to the synthesis of hyaluronic acid molecules of a size distribution not normally found with the native enzyme; the engineered size could be much smaller or larger than normal.

Various hyaluronic acid products of differing size have application in various areas, such as drug delivery. Applications in angiogenesis and wound healing are potentially large if hyaluronic acid polymers of from about 4 to about 20 monosaccharides can be made in good quantities.

Another particular application for small hyaluronic acid oligosaccharides is in the stabilization of recombinant human proteins used for medical purposes. A major problem with such proteins is their clearance from the blood and a short biological half life. One present solution to this problem is to couple a small molecule shield that prevents the protein from being cleared from the circulation too rapidly. Very small molecular weight hyaluronic acid is well suited for this role and would be nonimmunogenic and biocompatible. Larger molecular weight hyaluronic acid attached to a drug or protein may be used to target the reticuloendothelial cell system which has endocytic receptors for hyaluronic acid.

One of ordinary skill in the art given this disclosure would appreciate that there are several ways in which the size distribution of the hyaluronic acid polymer made by the hyaluronate synthase could be regulated to give different sizes. First, the kinetic control of product size can be altered by decreasing temperature, decreasing time of enzyme action and by decreasing the concentration of one or both sugar nucleotide substrates. Decreasing any or all of these variables will give lower amounts and smaller sizes of hyaluronic acid product. The disadvantages of these approaches are that the yield of product will also be decreased and it may be difficult to achieve reproducibility from day to day or batch to batch.

Secondly, the size distribution of the HA polymer can be regulated by altering the intrinsic ability of the enzyme to synthesize a large hyaluronic acid product. Changes to the protein can be engineered by recombinant DNA technology, including substitution, deletion and addition of specific amino acids (or even the introduction of prosthetic groups through metabolic processing). Such changes that result in an intrinsically slower enzyme then allows more reproducible control of hyaluronic acid size by kinetic means. The final hyaluronic acid size distribution is determined by certain characteristics of the enzyme, that rely on particular amino acids in the sequence. Among the 20% of residues absolutely conserved between the streptococcal enzymes and the eukaryotic hyaluronate synthases, there is a set of amino acids at unique positions that control or greatly influence the size of the hyaluronic acid polymer that the enzyme can make. Specific changes in any of these residues can produce a modified HAS that produces an HA product having a modified size distribution. Engineered changes to seHAS, spHAS, suHAS, pmHAS, or cvHAS that decrease the intrinsic size of the hyaluronic acid that the enzyme can make before the hyaluronic acid is released will provide powerful means to produce hyaluronic acid product of smaller or potentially larger size than the native enzyme.

Finally, larger molecular weight hyaluronic acid may be degraded with specific hyaluronidases to make lower molecular weight hyaluronic acid. This practice, however, is very difficult to achieve reproducibility and one must meticulously repurify the hyaluronic acid to remove the hyaluronidase and unwanted digestion products.

Figure 4:
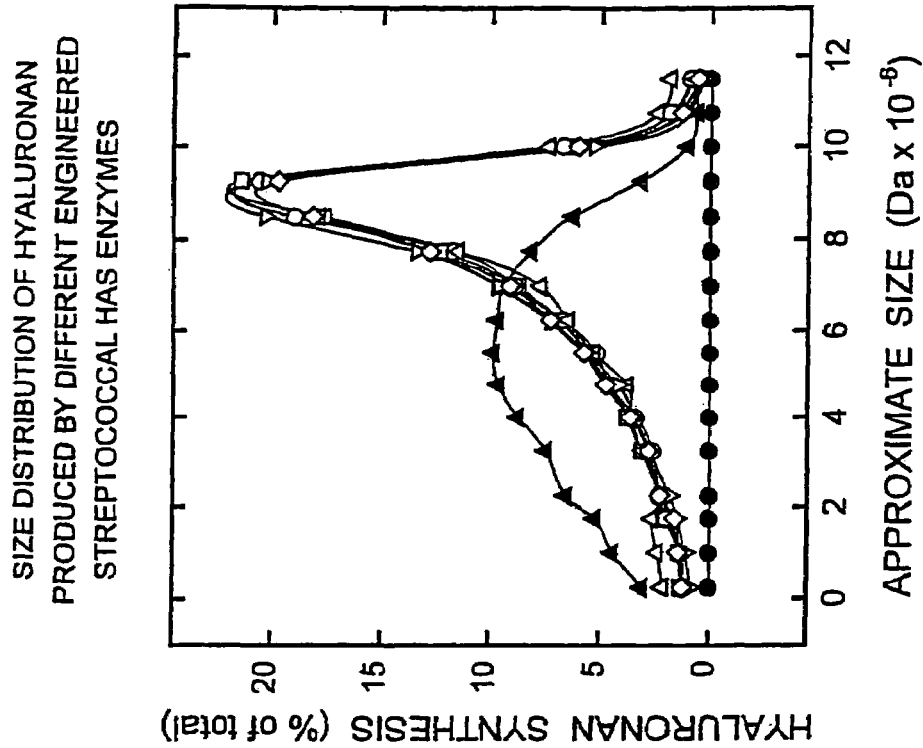

As shown in FIG. 4, hyaluronan synthase can be engineered to produce hyaluronic acid polymers of different size, in particular smaller, than the normal wildtype enzyme. The figure shows the distribution of HA sizes (in millions of Daltons, a measure of molecular weight) for a series of spHAS enzymes, each of which was engineered by site directed mutagenesis to have a single amino acid change from the native enzyme. Each has a different Cysteine residue replaced with Alanine. The cluster of five curves with open symbols represent the following spHAS proteins:

wildtype, C124A, C261A, C366A, and C402A. The filled circles represent the poorly expressed C225A protein which is only partially active.

The filled triangles represent the C280A spHAS protein, which is found to synthesize a much smaller range of HA polymers than the normal enzyme or the other variants shown. This reduction to practice shows that it is feasible to engineer the hyaluronate synthase enzyme to synthesize a desired range of HA product sizes. Any of the HAS genes encoding hyaluronate synthase disclosed herein can also be manipulated by site directed mutagenesis to produce an enzyme which synthesizes a desired range of HA product sizes.

Structurally modified hyaluronic acid is no different conceptually than altering the size distribution of the hyaluronic acid product by changing particular amino acids in the desired HAS or the spHAS. Derivatives of UDP-GlcNAc, in which the N-acetyl group is missing UDP-GlcN or replaced with another chemically useful group, are expected to be particularly useful. The strong substrate specificity must rely on a particular subset of amino acids among the 20% that are conserved. Specific changes to one or more of these residues creates a functional synthase that interacts less specifically with one or more of the substrates than the native enzyme. This altered enzyme could then utilize alternate natural or special sugar nucleotides to incorporate sugar derivatives designed to allow different chemistries to be employed for the following purposes: (i) covalently coupling specific drugs, proteins, or toxins to the structurally modified hyaluronic acid for general or targeted drug delivery, radiological procedures, etc. (ii) covalently cross linking the hyaluronic acid itself or to other supports to achieve a gel, or other three dimensional biomaterial with stronger physical properties, and (iii) covalently linking hyaluronic acid to a surface to create a biocompatible film or monolayer.

Bacteria can also be engineered to produce hyaluronic acid. For instance, we have created strains of *B. subtilis* containing a HAS gene, as well as the gene for one of the sugar nucleotide precursors. We chose this bacteria since it is frequently used in the biotech industry for the production of products for human use. These bacteria were intended as first generation prototypes for the generation of a bacterium able to produce hyaluronic acid in larger amounts than presently available using a wild type natural strain.

For example, three *Bacillus subtilis* strains were constructed to contain one or both of the *Streptococcus pyogenes* genes for hyaluronan synthase (spHAS) and UDP-glucose dehydrogenase (hasB), the results of which are shown in Table III. Based on a sensitive commercial radiometric assay to detect and quantitate HA, it was determined that the strain with both genes (strain #3) makes and secretes HA into the medium. The parent strain or the strain with just the dehydrogenase gene (strain #1) does not make HA. Strain #2, which contains just the spHAS gene alone makes HA, but only about 10% of what strain #3 makes. Agarose gel electrophoresis showed that the HA secreted into the medium by strain #3 is very high molecular weight.

The data in Table III demonstrates that *B. subtilis* 168 can be engineered to produce and secrete HA by the introduction by recombinant DNA techniques of the spHAS gene and the hasB gene. Although HA is made by this modified strain even without inclusion of the latter gene, the level of HA made with it is greatly elevated. *B. subtilis* 168 contains two genes (tauD and gtaB) that increase the levels of both sugar nucleotides needed for HA synthesis. Table IV demonstrates that *B. subtilis* 168 also makes HA, even in the absence of the hasB gene, when engineered to contain and express (on the plasmid pSM143, ATCC) seHAS as well as specific seHAS variants engineered to produce HA of different size than the wildtype. In particular, the variants seHAS(C226A) and seHAS(C281A) supported HA synthesis in live *B. subtilis* 168 cells. The level of HA synthesis in these latter cases was less than observed with cells expressing spHAS and the hasB gene, due to the lower endogenous level of the two precursors needed for HA synthesis.

In vitro experiments using isolated membranes from *B. subtilis* 168 cells transformed with plasmids containing hasB and the seHAS(C226A) or seHAS(C281A) variants demonstrated that the HA size distribution made by these modified HAS enzymes was larger and smaller, respectively, than that made by wildtype seHAS. The approximate size of HA produced in *B. subtilis* from wildtype seHAS is 1.5 MDa.

Figure 6:
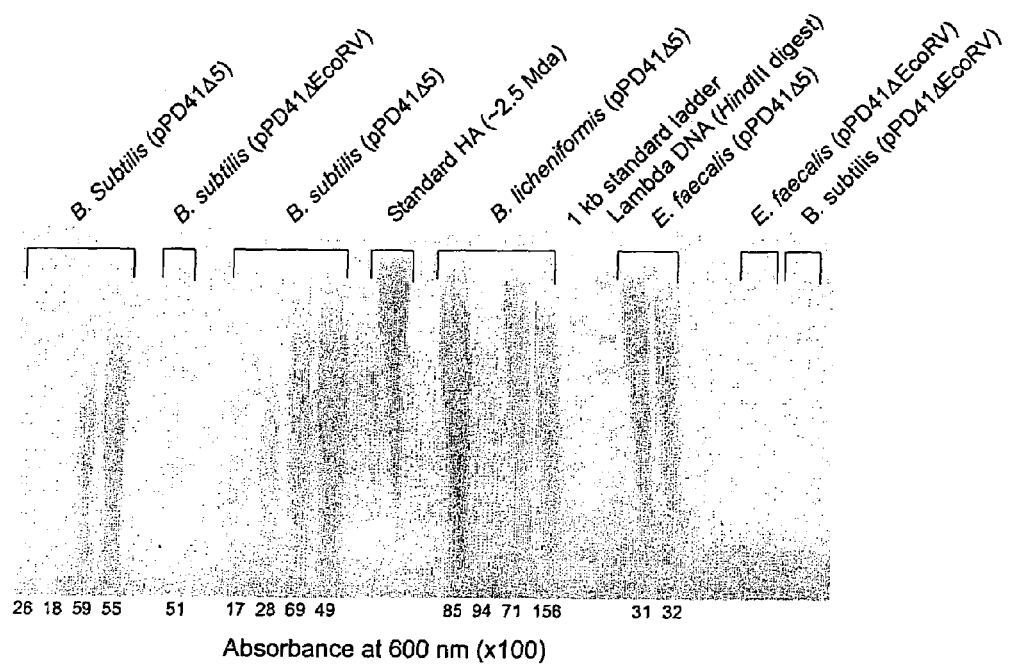

Recombinant HA production from the spHAS gene has also been demonstrated in *Bacillus licheniformis* and *Enterococcus faecalis*. FIG. 6 is a digital image of an agarose gel stained for HA. HA production can be seen in *B. subtilis*, *B. licheniformis* and *E. faecalis* strains having a plasmid encoding spHAS (pPD41Δ5) incorporated therein. As a negative control, a plasmid containing a nonfunctional hasA gene (pPD41ΔEcoRV) was introduced into each strain, and none of these strains was able to produce HA.

TABLE III

HA Production in *B. subtilis* 168 Containing spHAS and hasB genes

| Strain Number | Cells | Medium(*) (μg HA per ml of culture) | Strain with genes | Cell density (A$_{600}$) |
|---|---|---|---|---|
| 1 | 0 | 0 | hasB | 4.8 |
| 2 | 4 | 35 | SpHAS | 3.9 |
| 3 | ≧10 | ≧250 | SpHAS + hasB | 3.2 |

(*)Most HA is in media but some was cell-associated; HA was determined using the HA Test 50 kit from Pharmacia.

TABLE IV

Hyaluronan (HA) Produced in *B. subtilis* 168

| Recombinant Strains | HA (g/L) ELISA method |
|---|---|
| spHAS WT in pPD41Δ5 | 5.16 |
| SeHAS WT in pSM143 | 0.37 |
| SeHAS(C226A) in pSM143 | 0.25 |
| SeHAS(C281A) in pSM143 | 0.32 |
| pSM143 in *B. subtilis* 168 (vector alone) | 0.05 |

100 ml cultures were grown overnight; media was analyzed by HA Test Kit from Corgenix (Hyaluronic Acid "Chugai")

These experiments used the streptococcal promoters normally found with these genes to drive protein expression. It is expected that the construction of strains with the spHAS or seHAS reading frame under control of a Gram positive or *Bacillus*-compatible promoter would yield even more superior results. The vector used is a Gram positive/*E. coli* shuttle vector that has a medium copy number in *B. subtilis* and a gene for erythromycin resistance (enabling resistence to 8 μg/ml in *B. subtilis* or 175 μg/ml in *E. coli*). The *B. subtilis* host strain used is 1A1 from BGSC, which has a tryptophan requirement but otherwise is wildtype, and can sporulate. Cell growth and HA production was in Spizizens Minimal Media plus tryptophan, glucose, trace elements and erythromycin (8 µg/ml). Growth was at 32° C. with vigorous agitation until the medium was exhausted (~36 hours).

Tables III and IV demonstrate that these bioengineered cells, which would not normally make hyaluronic acid, became competent to do so when they are transformed with the spHAS or seHAS gene. Any one of the HAS genes described herein would also be capable of being introduced into a non-hyaluronic acid producing bacteria to create a bioengineered bacterial strain capable of producing hyaluronic acid.

Turning to the expression of one of the HAS genes described herein, whether from genomic DNA, or a cDNA, one may proceed to prepare an expression system for the recombinant preparation of the HAS protein. The engineering of DNA segment(s) for expression in a prokaryotic or eukaryotic system may be performed by techniques generally known to those of skill in recombinant expression.

HAS may be successfully expressed in eukaryotic expression systems, however, the inventors aver that bacterial expression systems can be used for the preparation of HAS for all purposes. It is believed that bacterial expression will ultimately have advantages over eukaryotic expression in terms of ease of use, cost of production, and quantity of material obtained thereby.

Figure 7:
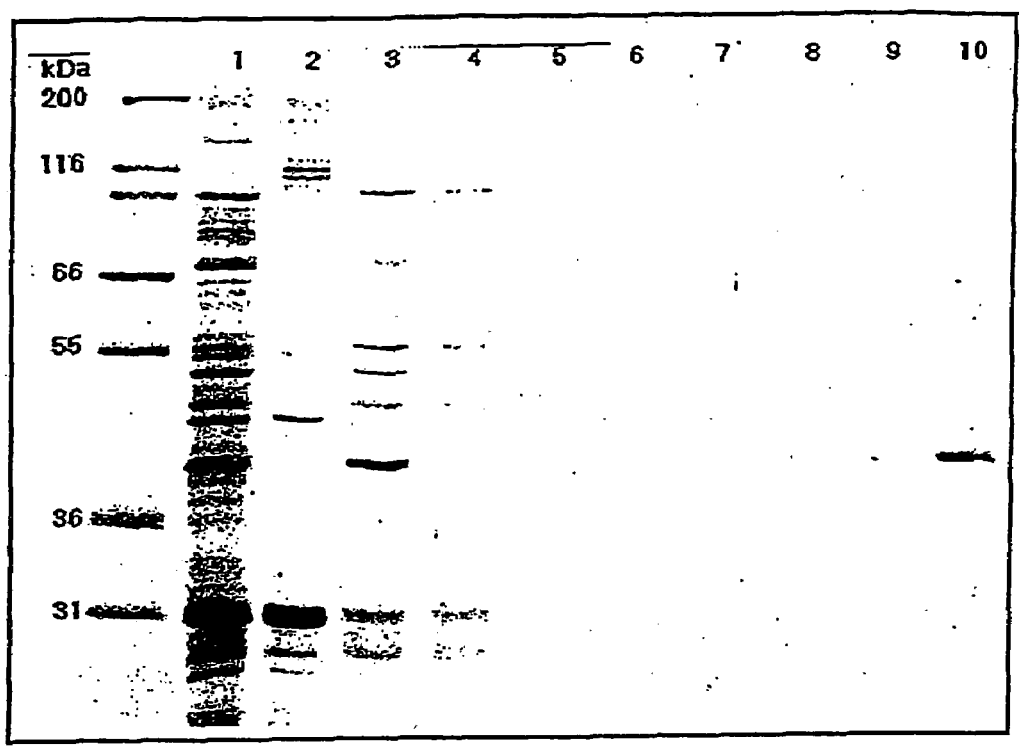
FIG. 7 depicts purification of Streptococcal HA synthase.

The purification of streptococcal hyaluronan synthase (seHAS) is shown in Table V and FIG. 7. Fractions from various stages of the purification scheme were analyzed by SDS-PAGE on a 12.5% gel, which was then stained with Coomassie Brilliant Blue R-250. Lanes: molecular weight markers; 1, whole E. coli membranes containing the recombinant seHAS-H6; 2, insoluble fraction after detergent solubilization of membranes; 3, detergent solubilized fraction; 4, flow-through from the Ni-NTA chromatography resin; 5–9, five successive washes of the column (two column volumes each); 10, the eluted pure HA synthase which is a single band. The purification of spHAS was identical to that shown for seHAS (Tlapak-Simmons, 1999).

TABLE V

| Step | Total Protein (ug) | Specific Activity (mmol/ug/hr) | Total Activity (nmol UDP-GlcUA) | Yield (%) | Purification (–fold) |
| --- | --- | --- | --- | --- | --- |
| Membranes | 3690 | 1.0 | 3649 | 100 | 1.0 |
| Extract | 2128 | 2.2 | 4725 | 129 | 2.2 |
| Affinity Column | 39 | 13 | 500 | 14 | 13.1 |

It is proposed that transformation of host cells with DNA segments encoding HAS will provide a convenient means for obtaining a HAS protein. It is also proposed that cDNA, genomic sequences, and combinations thereof, are suitable for eukaryotic expression, as the host cell will, of course, process the genomic transcripts to yield functional mRNA for translation into protein.

Another embodiment of the present invention is a method of preparing a protein composition comprising growing a recombinant host cell comprising a vector that encodes a protein which includes an amino acid sequence in accordance with SEQ ID NOS:2, 10, 12, 14, 16, 18 or 20 or functionally similar with conserved or semi-conserved amino acid changes. The host cell will be grown under conditions permitting nucleic acid expression and protein production followed by recovery of the protein so produced. The production of HAS and ultimately HA, including the host cell, conditions permitting nucleic acid expression, protein production and recovery will be known to those of skill in the art in light of the present disclosure and the methods described herein.

Preferred hosts for the expression of hyaluronic acid are prokaryotes, such as S. equisimilis, and other suitable members of the Streptococcus species. However, it is also known that HA may be synthesized by heterologous host cells expressing recombinant HA synthase, such as species members of the Bacillus, Enterococcus, or even Escherichia genus. A most preferred host for expression of the HA synthase of the present invention is a bacteria transformed with the HAS gene of the present invention, such as Lactococcus species, Bacillus subtilis or E. coli.

Most preferred hosts for use in the methods of expression of HA of the present invention include Bacillus species, because such cells are effective industrial secretors, and several species have been designated as GRAS organisms. Examples of Bacillus cells that may be utilized in the methods of the present invention include, but are not limited to, Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus metaterium, Bacillus pumilus, Bacillus stearothermophilus, Bacillus subtilis and Bacillus thuringienisis. A most preferred host is Bacillus subtilis.

Figure 8:
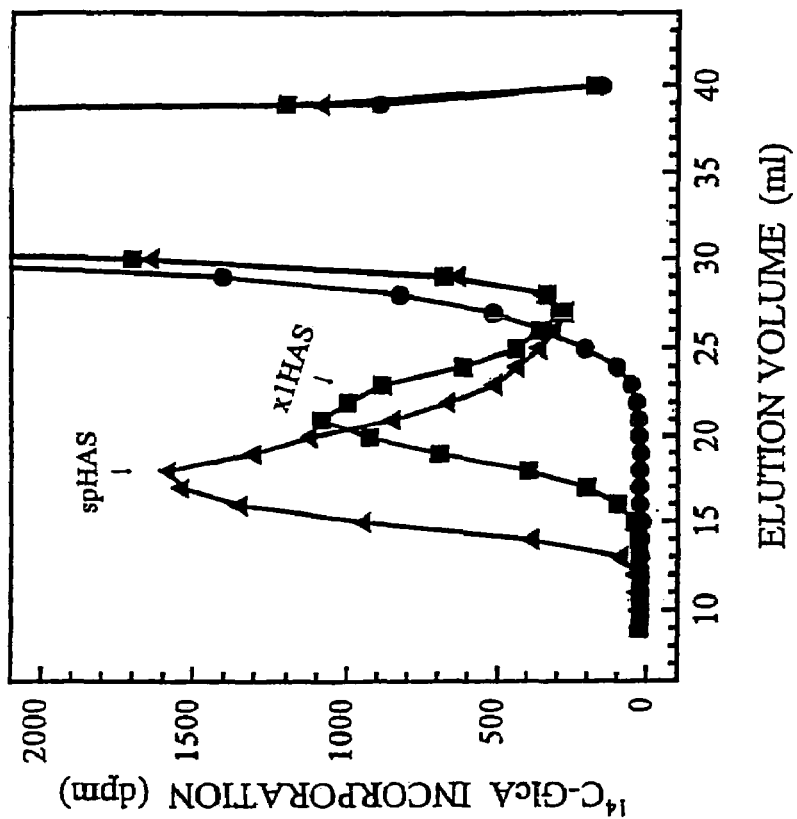
FIG. 8 depicts a gel filtration analysis of HA synthesized by recombinant streptococcal HAS expressed in yeast membranes.

It is similarly believed that almost any eukaryotic expression system may be utilized for the expression of HAS, e.g., baculovirus-based, glutamine synthase-based, dihydrofolate reductase-based systems, SV-40 based, adenovirus-based, cytomegalovirus-based, yeast-based, and the like, could be employed. For expression in this manner, one would position the coding sequences adjacent to and under the control of the promoter. It is understood in the art that to bring a coding sequence under the control of such a promoter, one positions the 5' end of the transcription initiation site of the transcriptional reading frame of the protein between about 1 and about 50 nucleotides "downstream" of (i.e., 3' of) the chosen promoter. Also, Saccharomyces cerevisiae yeast expression vector systems, such as pYES2, will also produce HAS under control of the GAL promoter as shown in FIG. 8. FIG. 8 shows that the spHAS or the x1HAS enzyme was produced in recombinant yeast using the pYES2 plasmid. When supplied with UDP-GlcUA and UDP-GlcNAc, either enzyme makes high molecular weight HA, as observed in these gel filtration chromatography profiles (the HA peak is from about 13 ml to about 25 ml).

FIG. 8 shows a gel filtration analysis of hyaluronic acid synthesized by recombinant HASs expressed in yeast membranes. A DNA fragment encoding (a) the open reading frame of 419 amino acid residues corresponding to spHAS (with the original Val codon switched to Met) or (b) the x1HAS protein was subcloned by standard methods in the pYES2 yeast expression vector (from Invitrogen) to produce pYES/HA. Membranes from cells with this construct were prepared by agitation with glass beads. The samples derived from pYES/HA constructs contained substantial HA synthase activity and the "42 kDa" HAS protein was detected by Western analysis using specific antibodies; membranes from cells with vector alone possessed neither activity nor the immunoreactive band (not shown). Membranes (315 µM protein) were first incubated with carrier free UDP-[$^{14}$C] GlcUA (1 µCi$^{14}$C) and 900 uM unlabeled UDP-GlcNAc in 50 mM Tris, pH 7, 20 mM MgCl2, 1 mM DTT, and 0.05 M Nacl (450 µl reaction volume) at 30 degrees Celsius for 1.5 minutes. After this pulse-label period nonradiolabeled UDP-GlcUA was then added to final concentrations of 900 uM. Samples (100 µL) were taken after the pulse at 1.5 min (dark circle), and 15 (black square), and 45 (black triangle) min after the "chase." The reactions were terminated by the addition of SDS to 2% and heating at 95 degrees Celsius for 1 min. The samples were clarified by centrifugation (10,000×g, 5 min) before injection of half of the sample onto a Sephacryl S-500HR gel filtration column (Pharmacia; 1×50 cm) equilibrated in 0.2 M Nacl, 5 mM Tris, pH 8.

The column was eluted at 0.5 ml/min and radioactivity in the fractions (1 ml) was quantitated by liquid scintillation counting after adding BioSafeII cocktail (4.5 ml, Research Products Intl.). The void volume and the totally included volumes were at elution volumes of 14 ml and 35.5 ml, respectively. The peak of blue dextran (average 2×10 6 Da) eluted at 25–27 ml. The recombinant HAS expressed in the eukaryotic yeast cells makes high molecular weight hyaluronic acid in vitro.

Where eukaryotic expression is contemplated, one will also typically desire to incorporate into the transcriptional unit which includes the HAS gene or DNA, an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

It is contemplated that virtually any of the commonly employed eukaryotic host cells can be used in connection with the expression of HAS in accordance herewith. Examples of preferred cell lines for expressing HAS cDNA of the present invention include cell lines typically employed for eukaryotic expression such as 293, AtT-20, HepG2, VERO, HeLa, CHO, WI 38, BHK, COS-7, RIN and MDCK cell lines. This will generally include the steps of providing a recombinant host bearing the recombinant DNA segment encoding the HAS enzyme and capable of expressing the enzyme; culturing the recombinant host in media under conditions that will allow for transcription of the cloned HAS gene or cDNA and appropriate for the production of the hyaluronic acid; and separating and purifying the HAS enzyme or the secreted hyaluronic acid from the recombinant host.

Figure 5:
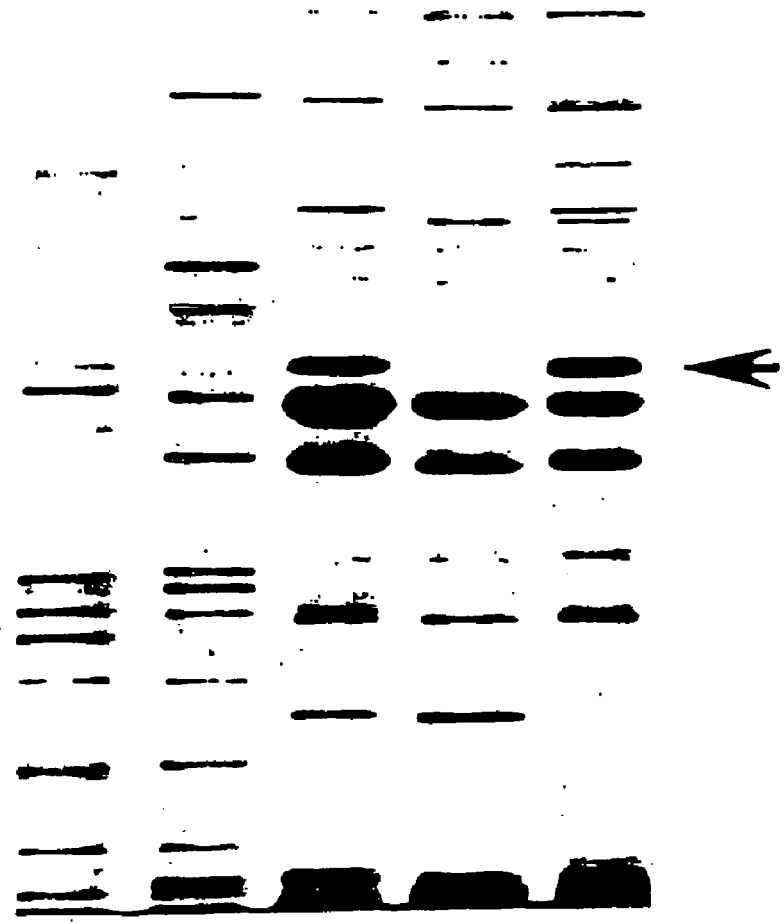

Generally, the conditions appropriate for expression of the cloned HAS gene or cDNA will depend upon the promoter, the vector, and the host system that is employed. For example, where one employs the lac promoter, one will desire to induce transcription through the inclusion of a material that will stimulate lac transcription, such as isopropylthiogalactoside. For example, the cloned seHAS and spHAS genes are expressed as $HIS_6$ containing proteins in E. coli for the purpose of purification of the HAS as shown in FIG. 5. Where other promoters are employed, different materials may be needed to induce or otherwise up-regulate transcription.

FIG. 5 depicts the overexpression of recombinant seHAS and spHAS in E. coli. Membrane proteins (5 μM per lane) were fractionated by SDS-PAGE using a 10% (w/v) gel under reducing conditions. The gel was stained with Coomassie blue R-250, photographed, scanned, and quantitated using a molecular dynamics personal densitometer (model PDSI P60). The position of HA synthase is marked by the arrow. Lane A is native spHAS (Group A); Lane C is native seHAS; Lane E is recombinant seHAS; Lane P is recombinant spHAS; Lane V is vector alone. Standards used were Bio-rad low Mr and shown in kDa.

In addition to obtaining expression of the synthase, one will preferably desire to provide an environment that is conducive to HA synthesis by including appropriate genes encoding enzymes needed for the biosynthesis of sugar nucleotide precursors, or by using growth media containing substrates for the precursor-supplying enzymes, such as N-acetylglucosamine or glucosamine (GlcNAc or $GlcNH_2$) and glucose (Glc).

One may further desire to incorporate the gene in a host which is defective in the enzyme hyaluronidase, so that the product synthesized by the enzyme will not be degraded in the medium. Furthermore, a host would be chosen to optimize production of HA. For example, a suitable host would be one that produced large quantities of the sugar nucleotide precursors to support the HAS enzyme and allow it to produce large quantities of HA. Such a host may be found naturally or may be made by a variety of techniques including mutagenesis or recombinant DNA technology. The genes for the sugar nucleotide synthesizing enzymes, particularly the UDP-Glc dehydrogenase required to produce UDP-GlcUA, could also be isolated and incorporated in a vector along with the HAS gene or cDNA. A preferred embodiment of the present invention is a host containing these ancillary recombinant genes or cDNAs, thereby allowing for increased production of the sugar nucleotides and thus HA.

The means employed for culturing of the host cell is not believed to be particularly crucial. For useful details, one may wish to refer to the disclosure of U.S. Pat. Nos. 4,517,295; 4,801,539; 4,784,990; or 4,780,414; all of which are expressly incorporated herein by reference in their entirety. Where a prokaryotic host is employed, such as S. equisimilis, one may desire to employ a fermentation of the bacteria under anaerobic conditions in $CO_2$-enriched broth growth media. This allows for a greater production of HA than under aerobic conditions. Another consideration is that Streptococcal cells grown anaerobically do not produce pyrogenic exotoxins. Appropriate growth conditions can be customized for other prokaryotic hosts, as will be known to those of skill in the art, in light of the present disclosure.

Once the appropriate host has been constructed and cultured under conditions appropriate for the production of HA, one will desire to separate the HA so produced. Typically, the HA will be secreted or otherwise shed by the recombinant organism into the surrounding media, allowing the ready isolation of HA from the media by known techniques. For example, HA can be separated from the cells and debris by at least one of filtration, centrifugation, and flocculation, and the addition of trichloroacetic acid may further facilitate in separating cells and debris from the hyaluronic acid. The HA is then separated from the media by at least one of precipitation, ultrafiltration and dialysis. Precipitation agents include alcohols such as ethanol and isopropanol, organic solvents or compounds such as acetone or quaternary organic ammonium (aliphatic positively-charged) salts such as cetyl pyridinium chloride (CPC) or cetyl triammonium bromide (CTB).

A preferred technique for isolation of HA is described in U.S. Pat. No. 4,517,295, which is expressly incorporated herein by reference, in which the organic carboxylic acid, trichloroacetic acid, is added to the bacterial suspension at the end of the fermentation. The trichloroacetic acid causes the bacterial cells to clump and die and facilitates the ease of separating these cells and associated debris from HA, the desired product. The clarified supernatant is concentrated and dialyzed to remove low molecular weight contaminants including the organic acid. The aforementioned procedure utilizes filtration through filter cassettes, such as those containing 0.22 μm pore size filters. Diafiltration is continued until the conductivity of the solution decreases to approximately 0.5 mega-ohms.

The concentrated HA is precipitated by adding an excess of reagent grade ethanol or other organic solvent and the precipitated HA is then dried by washing with ethanol and vacuum dried, lyophilized to remove alcohol. The HA can then be redissolved in a borate buffer, pH 8, and precipitated with CPC or certain other organic ammonium salts such as CETAB, a mixed trimethyl ammonium bromide solution at 4 degree(s) Celsius. The precipitated HA is recovered by coarse filtration, resuspended in 1 M NaCl, diafiltered and concentrated as further described in the above referenced patent. The resultant HA is filter sterilized and ready to be converted to an appropriate salt, dry powder or sterile solution, depending on the desired end use.

A. Typical Genetic Engineering Methods Which May Be Employed

If cells without formidable cell membrane barriers are used as host cells, transfection is carried out by the calcium phosphate precipitation method, well known to those of skill in the art. However, other methods may also be used for introducing DNA into cells, such as by nuclear injection, cationic lipids, electroporation, protoplast fusion or by the BIOLISTIC™ Bioparticle delivery system developed by DuPont (1989). The advantage of using the DuPont system is a high transformation efficiency. If prokaryotic cells or cells which contain substantial cell wall constructions are used, the preferred method of transfection is calcium treatment using calcium chloride to induce competence or electroporation.

Construction of suitable vectors containing the desired coding and control sequences employ standard ligation techniques. Isolated plasmids or DNA fragments are cleaved, tailored, and religated in the form desired to construct the plasmids required. Cleavage is performed by treating with restriction enzyme(s) in suitable buffer. In general, about 1 μM plasmid or DNA fragments are used with about 1 unit of enzyme in about 20 μl of buffer solution. Appropriate buffers and substrate amounts for particular restriction enzymes are specified by the manufacturer. Incubation times of about 1 hour at 37° C. are workable.

After incubations, protein is removed by extraction with phenol and chloroform, and the nucleic acid is recovered from the aqueous fraction by precipitation with ethanol. If blunt ends are required, the preparation is treated for 15 minutes at 15° C. with 10 units of Polymerase I (Klenow), phenol-chloroform extracted, and ethanol precipitated. For ligation approximately equimolar amounts of the desired components, suitably end tailored to provide correct matching are treated with about 10 units T4 DNA ligase per 0.5 μM DNA. When cleaved vectors are used as components, it may be useful to prevent religation of the cleaved vector by pretreatment with bacterial alkaline phosphatase.

For analysis to confirm functional sequences in constructed plasmids, the first step was to amplify the plasmid DNA by cloning into specifically competent *E. coli* SURE cells (Stratagene) by doing transformation at 30–32° C. Second, the recombinant plasmid is used to transform *E. coli* K5 strain Bi8337-41, which can produce the UDP-GlcUA precursor, and successful transformants selected by antibiotic resistance as appropriate. Plasmids from the library of transformants are then screened for bacterial colonies that exhibit HA production. These colonies are picked, amplified and the plasmids purified and analyzed by restriction mapping. The plasmids showing indications of a functional HAS gene are then further characterized by any number of sequence analysis techniques which are known by those of ordinary skill in the art.

B. Source and Host Cell Cultures and Vectors

In general, prokaryotes were used for the initial cloning of DNA sequences and construction of the vectors useful in the invention. It is believed that a suitable source may be Gram-positive cells, particularly those derived from the Group C Streptococcal strains. Bacteria with a single membrane, but a thick cell wall such as Staphylococci and Streptococci are Gram-positive. Gram-negative bacteria such as *E. coli* contain two discrete membranes rather than one surrounding the cell. Gram-negative organisms tend to have thinner cell walls. The single membrane of the Gram-positive organisms is analogous to the inner plasma membrane of Gram-negative bacteria.

In general, plasmid vectors containing origins of replication and control sequences which are derived from species compatible with the host cell are used in connection with these hosts. The vector ordinarily carries an origin of replication, as well as marking sequences which are capable of providing phenotypic selection in transformed cells. For example, *E. coli* is typically transformed using pBR322, a plasmid derived from an *E. coli* species. pBR322 contains genes for ampicillin and tetracycline resistance and thus provides easy means for identifying transformed cells. A pBR plasmid or a pUC plasmid, or other microbial plasmid or phage must also contain, or be modified to contain, promoters which can be used by the microbial organism for expression of its own proteins. Such promoters may be heterologous promoters, that is, promoters from another organism, as long as the promoter is compatible with the host cell, i.e., recognized by the RNA polymerase of the host cell such that the RNA polymerase transcribes the gene to which the host-compatible promoter is attached.

Those promoters most commonly used in recombinant DNA construction include the lacZ promoter, tac promoter, the T7 bacteriophage promoter, and tryptophan (trp) promoter system. While these are the most commonly used, other microbial promoters have been discovered and utilized, and details concerning their nucleotide sequences have been published, enabling a skilled worker to ligate them functionally with plasmid vectors.

In addition, the promoter may be a modified RNA polymerase promoter having increased promoter activity. The modification to the promoter may be a mutation, or the addition of two or more promoter elements in tandem. When two or more promoter elements are provided in tandem, the two or more tandem promoter elements may be the same promoter element or two or more different promoter elements. The term "tandem promoter elements" as used herein will be understood to mean two or more promoter sequences each of which is operably linked to a coding sequence such that the promoter sequences direct the production of a polypeptide encoded by the coding sequence by mediating the transcription of the coding sequence into mRNA. Tandem promoters, as well as constructs and methods for use thereof in expression in *Bacillus* cells, are described in detail in U.S. Pat. Nos. 5,955,310 and 6,255,076, issued to Widner et al. on Sep. 21, 1999 and Jul. 3, 2001, respectively, the contents of which are expressly incorporated herein in their entirety.

In addition, when a recombinant vector of the present invention contains more than one nucleic acid segment wherein each has a coding region encoding a protein, such as for example, a nucleic acid segment having a coding region encoding enzymatically active hyaluronan synthase and a nucleic acid segment having a coding region encoding enzymatically active UDP-glucose dehydrogenase, each of the nucleic acid segments are operably linked to a promoter. The two or more nucleic acid segments may be linked to the same promoter, and this single promoter may drive expression of both genes, or the two or more nucleic acid segments may be linked to different promoters.

In addition to prokaryotes, eukaryotic microbes, such as yeast cultures may also be used. *Saccharomyces cerevisiae,* or common baker's yeast is the most commonly used among eukaryotic microorganisms, although a number of other strains are commonly available. For expression in *Saccharomyces,* the plasmid YRp7, for example, is commonly used. This plasmid already contains the trp1 gene which provides a selection marker for a mutant strain of yeast lacking the ability to grow without tryptophan, for example, ATCC No. 44076 or PEP4-1. The presence of the trp1 lesion as a characteristic of the yeast host cell genome then provides an effective environment for detecting transformation by growth in the absence of tryptophan. Suitable promoting sequences in yeast vectors include the promoters for the galactose utilization genes, the 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter region for alcohol dehydrogenase 2, cytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture has become a routine procedure in recent years. Examples of such useful host cell lines are VERO and HeLa cells, Chinese hamster ovary (CHO) cell lines, and WI38, BHK, COS, and MDCK cell lines.

For use in mammalian cells, the control functions on the expression vectors are often provided by viral material. For example, commonly used promoters are derived from polyoma, Adenovirus 2, bovine papilloma virus and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the Hind III site toward the Bgl I site located in the viral origin of replication.

Further, it is also possible, and often desirable, to utilize promoter or control sequences normally associated with the desired gene sequence, provided such control sequences are compatible with the host cell systems. An origin of replication may be provided either by construction of the vector to include an exogenous origin, such as may be derived from SV40 or other viral (e.g., Polyoma, Adeno, BPV) source, or may be provided by the host cell chromosomal replication mechanism. If the vector is integrated into the host cell chromosome, the latter mechanism is often sufficient.

C. Isolation of a bona fide HA Synthase Gene from a Highly Encapsulated Strain of Group C *Streptococcus equisimilis*

Figure 9:
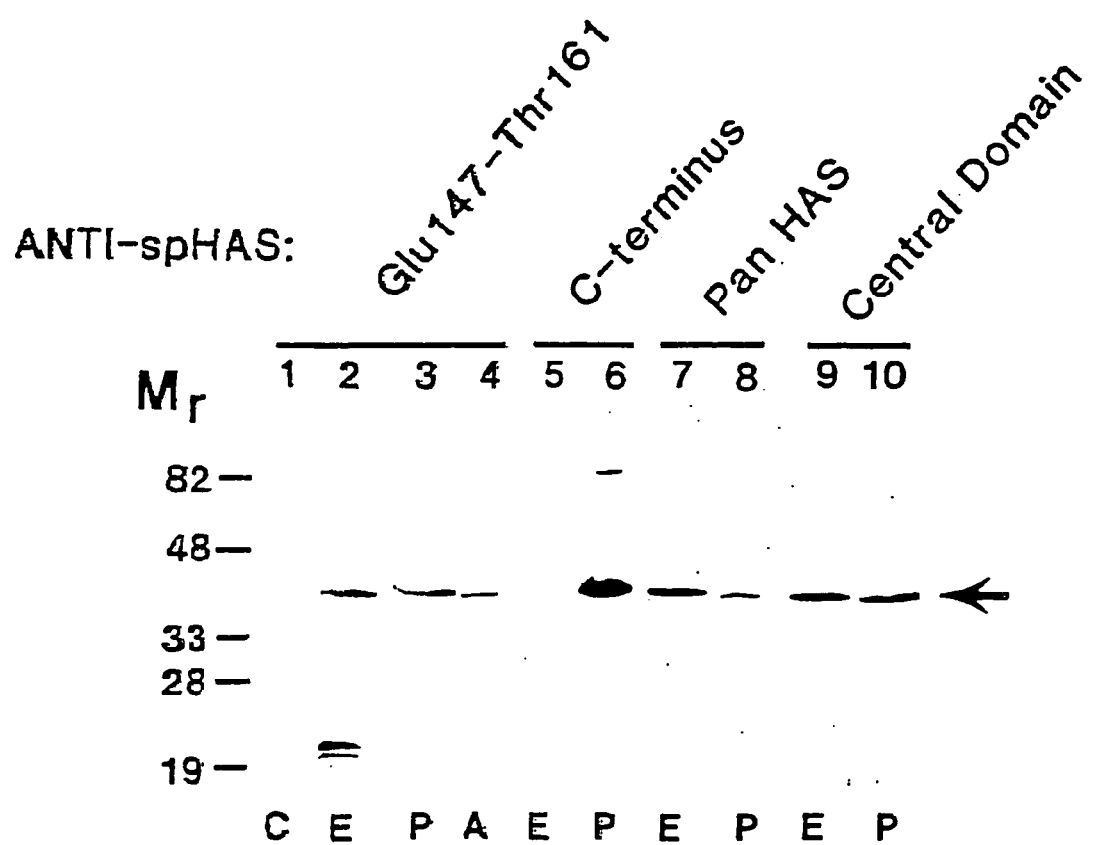
FIG. 9 is a Western blot analysis of recombinant seHAS using specific antibodies.

The encoded protein, designated seHAS, is 417 amino acids (calculated molecular weight of 47,778 and pI of 9.1) and is the smallest member of the HAS family identified thus far (FIG. 2). seHAS also migrates anomalously fast in SDS-PAGE ($M_r$~42 kDa) (FIGS. 5 and 9).

FIG. 9 is a graphical representation of a Western Blot analysis of recombinant seHAS using specific antibodies. Group C©; lane 1) or Group A (A; lane 4) Streptococcal membranes and *E. coli* membranes (9 µg/lane) containing recombinant seHAS (E; lanes 2, 7, and 9) or spHAS (P; lanes 3, 6, 8, and 10) were fractionated by reducing SDS-PAGE and electrotransferred to nitrocellulose. Strips of nitrocellulose were probed and developed as described in the application using purified IgG fractions raised to the following regions of spHAS: central domain peptide $E^{147}$-$T^{161}$ (lanes 1–4); C-terminus peptide (lanes 5–6); the complete protein (lanes 7 and 8); recombinant central domain (lanes 9 and 10). Nonimmune IgG or membranes from cells transformed with vector alone gave no staining as in lane 5.

The seHAS and spHAS protein-encoding sequences (SEQ ID NOS:1 and 13, respectively) are 72% identical. The deduced protein sequence of seHAS was confirmed by reactivity with a synthetic peptide antibody (FIG. 9). Recombinant seHAS expressed in *E. coli* was recovered in membranes as a major protein (FIG. 5) and synthesized very large molecular weight HA in the presence of UDP-GlcNAc and UDP-GlcUA in vitro (FIG. 10).

Figure 10:
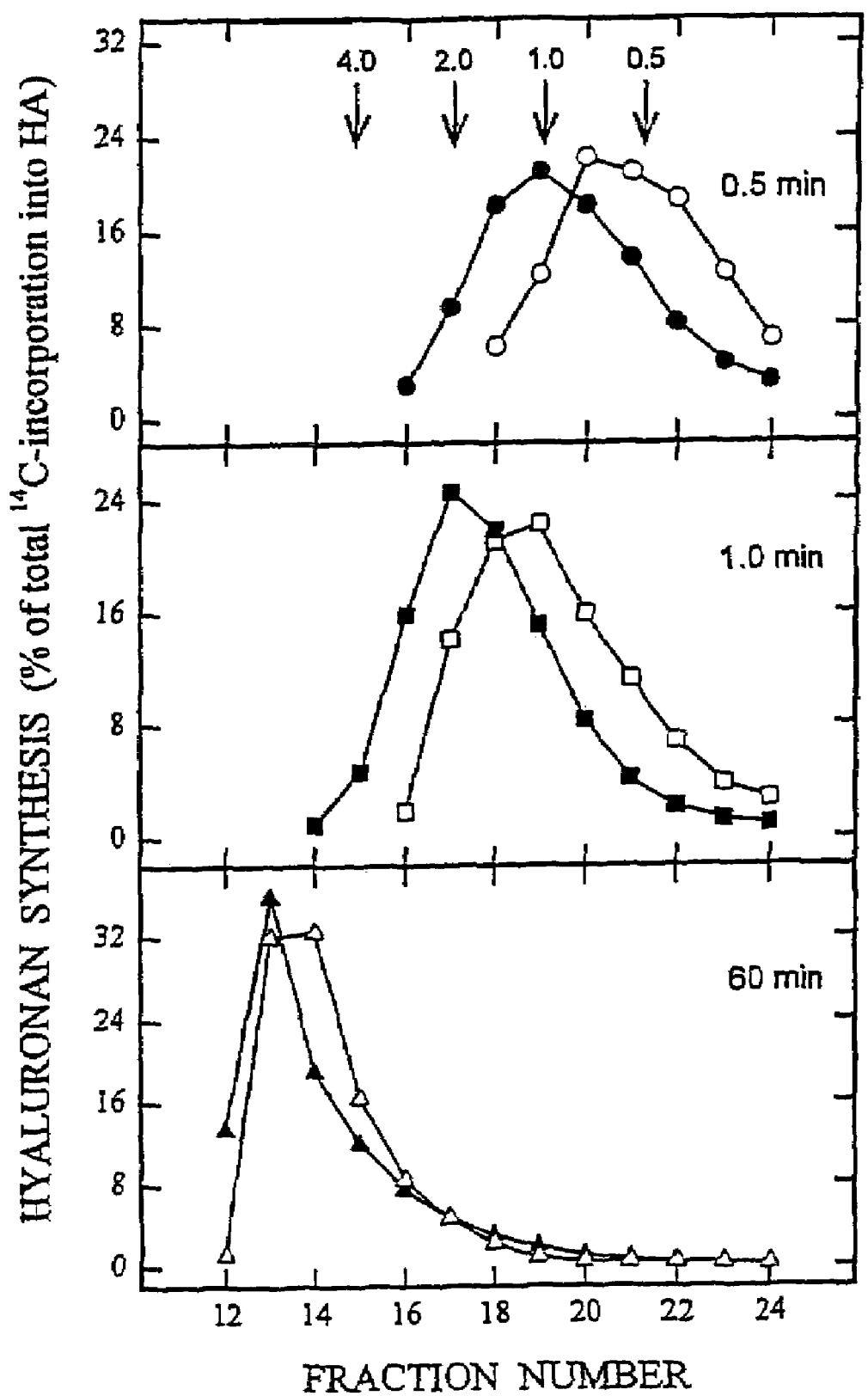
FIG. 10 is a kinetic analysis of the HA size distributions produced by recombinant seHAS and spHAS.

FIG. 10 shows a kinetic analysis of the HA size distributions produced by seHAS and spHAS. *E. coli* membranes containing equal amounts of seHAS or spHAS protein were incubated at 37° C. with 1.35 mM UDP-[$^{14}$C] GlcUA ($1.3 \times 10^3$ dpm/nmol) and 3.0 mM UDP-GlcNAc as described in the application. These substrate concentrations are greater than 15 times the respective Km values. Samples taken at 0.5, 1.0, and 60 min were treated with SDS and chromatographed over Sephacryl S400 HR. The HA profiles in the fractionation range of the column (fractions 12–24) are normalized to the percent of total HA in each fraction. The values above the arrows in the top panel are the MWs (in millions) of HA determined directly in a separate experiment using a Dawn multiangle laser light scattering instrument (Wyatt Technology Corp.). The size distributions of HA synthesized by seHAS (●, ■, ▲) and spHAS (○, □, △) at 0.5 min (○, ●), 1.0 min (□, ■) and 60 min (△, ▲) are shown as indicated. Analysis showed that seHAS and spHAS are essentially identical in the size distribution of HA chains they synthesize (FIG. 10). SeHAS is twice as fast as spHAS in its ability to make HA.

C.1 Bacterial Strains and Vectors

The mucoid group C strain D181; (*Streptococcus equisimilis*) was obtained from the Rockefeller University Collection. The *E. coli* host strains Sure and XL1-Blue MRF' were from Stratagene and strain Top10 F' was from Invitrogen. Unless otherwise noted, Streptococci were grown in THY and *E. coli* strains were grown in LB medium. pKK-223 Expression vector was from Pharmacia, PCR 2.1 cloning vector was from Invitrogen, and predigested λ Zap Express TM Bam HI/CIAP Vector was from Stratagene.

C.2 Recombinant DNA and Cloning

High molecular mass Genomic DNA from *Streptococcus equisimilis* isolated by the method of Caparon and Scott (as known by those with ordinary skill in the art) was partially digested with Sau3A1 to an average size of 2–12 kb. The digested DNA was precipitated with ethanol, washed and ligated to the Bam HI/CIAPλ Zap Express vector. Ligated DNA was packaged into phage with a Packagene™ extract obtained from Promega. The titer of the packaged phage library was checked using XL1-Blue MRF' *E. coli* as a host.

C.3 Degenerate PCR Amplification

Degenerate oligonucleotides were designed based upon conserved sequences among spHAS (*Streptococcus pyogenes*), DG42 (*Xenopus laevis* HAS; 19) and nodC (a *Rhizobium meliloti* nodulation factor; 20) and were used for PCR amplification with D181 genomic DNA as a template. Amplification conditions were 34 cycles at: 94° C. for 1 min, 44° C. for 1 min, 72° C. for 1.5 min followed by a final extension at 72° C. for 10 min. Oligonucleotide HADRF1. 5'-GAY MGA YRT YTX ACX AAT TAY GCT ATH GAY TTR GG-3' (sense strand) corresponds to the sequence $D^{259}$RCLTNYAIDL (spHAS). Oligonucleotide HACTR1, 5'-ACG WGT WCC CCA NTC XGY ATT TTT NAD XGT RCA-3' (antisense strand) corresponds to the region $C^{404}$TIKNTEWGTR (spHAS). The degeneracy of bases at some positions are represented by nomenclature adopted by the IUPAC in its codes for degenerate bases listed in Table VI.

TABLE VI

IUPAC Codes - Degenerate Bases
The International Union for Pure and Applied Chemistry (IUPAC) has established a standard single-letter designation for degenerate bases. These are:

| | |
|---|---|
| B = | C + G + T |
| D = | A + G + T |
| H = | A + C + T |
| K = | T + G |
| M = | A + C |
| N = | A + C + G + T |
| R = | A + G |
| S = | G + C |
| W = | A + T |
| V = | A + C + G |
| X = | a minor bases (specified elsewhere) |
| Y = | C + T |

These two oligonucleotides gave a 459 bp PCR product, which was separated on an agarose gel and purified using the BIO-101 Geneclean kit. This fragment was then cloned into PCR2.1 vector using TOP 10 F' cells as a host according to the manufacturer's directions. Double stranded plasmid DNA was purified from *E. coli* (Top 10 F') using the QIAfilter Plasmid Midi Kit (Qiagen). Two other degenerate sense primers were also synthesized: HAVAF1, 5'-GTN GCT GCT GTW RTX CCW WSX TWT AAY GAR GA-3' (corresponding to the region $V^{66}$AAVIPSYNE of spHAS) and HAVDF1, 5'-GTX RWT GAY GGN WSX WSN RAX GAT GAX GC-3' (based on $V^{100}$DDGSSNTD of spHAS).

Two unique antisense primers were synthesized based on the sequence of the 459 bp PCR product. These were: D181.2, 5'-GAA GGA CTT GTT CCA GCG GT-3' and D181.4, 5'-TGA ATG TTC CGA CAC AGG GC-3'. Each of the two degenerate sense primers, when used with either D181.2 or D181.4 to amplify D181 genomic DNA, gave expected size PCR products. The four PCR products were cloned and sequenced using the same strategy as above. For each PCR product, sequences obtained from six different clones were compared in order to derive a consensus sequence. Thus we obtained a 1042 bp sequence with a continuous ORF with high homology to spHAS.

C.4 Library Screening

Two molecular probes were used to screen the library; the cloned 459 bp PCR product and oligonucleotide D181.5 (5'-GCTTGATAGGTCACCAGTGTCACG-3'; derived from the 1042 bp sequence). The 459 bp PCR product was radiolabeled using the Prime-It 11 random primer labeling Kit (Stratagene) according to the manufacturers instructions. Oligonucleotides were labeled by Kinace-It Kinasing Kit (Stratagene) using $[\gamma^{32}P]$ATP. Radiolabeled products were separated from nonlabeled material on NucTrap Push columns (Stratagene). The oligoprobe hybridized specifically with a D181 genomic digest on Southern blots. To screen the λ phage library, XLBLUE MRF' was used as a host (3000 plaques/plate) on Nitrocellulose membranes containing adsorbed phage, were prehybridized at 60° C. and hybridized with 5'-end labeled oligonucleotide, D181.5, in QuikHyb Hybridization solution (Stratagene) at 80° C. according to instructions.

The membranes were then washed with 2×SSC buffer and 0.1% (w/v) SDS at room temperature for 15 min, at 60° C. with 0.1×SSC buffer and 0.1% SDS (w/v) for 30 min, dried and then exposed to Bio-Max MS film overnight at −70° C. Positive plaques were replated and rescreened twice. Pure positive phages were saved in SM buffer with chloroform. PCR on these phages with vector primers revealed 3 different insert sizes.

PCR with a combination of vector primers and primers from different regions of the cloned 1042 bp sequence revealed that only one of the three different phages had the complete HAS gene. The insert size in this phage was 6.5 kb. Attempts to subclone the insert into plasmid form by autoexcision from the selected phage library clone failed. Therefore, a PCR strategy was applied again on the pure positive phage DNA to obtain the 5' and 3' end of the ORF. Oligonucleotide primers D181.3 (5'-GCCCTGTGTCG-GAACATTCA-3') and T3 (vector primer) amplified a 3 kb product and oligonucleotides D181.5 and T7 (vector primer) amplified a 2.5 kb product. The 5' and 3'-end sequences of the ORF were obtained by sequencing these two above products. Analysis of all PCR product sequences allowed us to reconstruct the ORF of the 1254 bp seHAS gene.

C.5 Expression Cloning of the seHAS

Primers were designed at the start and stop codon regions of seHAS to contain an EcoR1 restriction site in the sense oligonucleotide (5'-AGGATCCGAATTCATGAGAACAT-TAAAAAACCTC-3') and a Pst1 site in the antisense oligonucleotide (5'-AGAATTCTGCAGTTATAATAATTTTT-TACGTGT-3'). These primers amplified a 1.2 kb PCR product from D181 genomic DNA as well as from pure hybridization-positive phage. The 1.2 kb product was purified by agarose gel electrophoresis, digested with Pst1 and EcoR1 and cloned directionally into Pst1-and EcoR1-digested pKK223 vector. The ligated vector was transformed into E. coli SURE cells that were then grown at 30° C. This step was practically important since other host cells or higher temperatures resulted in deletions of the cloned insert. Colonies were isolated and their pDNA purified. Out of six colonies (named a, b, c, d, e, and f), five had the correct size insert, while one had no insert.

C.6 HA Synthase Activity

HA synthase activity was assayed in membranes prepared from the 5 above clones. Fresh log phase cells were harvested at 3000 g, washed at 4° C. with PBS and membranes were isolated by a modification of a protoplast method as known by those of ordinary skill in the art. Membrane preparations from Streptococcus pyogenes and Streptococcus equisimilis were also obtained by modification of a different protoplast procedure. Membranes were incubated at 37° C. in 50 mM sodium and potassium phosphate, pH 7.0 with 20 mM $MgCl_2$, 1 mM DTE, 120 μM UDP-GlcUA and 300 μM UDP-GlcNAc. Incorporation of sugar was monitored by using UDP-[$^{14}$C]GlcUA (318 mCi/mmol; ICN) and/or UDP-[$^{3}$H]GlcNAc (29.2 Ci/mmol NEN). Reactions were terminated by addition of SDS to a final concentration of 2% (w/v). Product HA was separated from precursors by descending paper chromatography and measured by determining incorporated radioactivity at the origin.

C.7 Gel Filtration Analysis

Radiolabeled HA produced in vitro by membranes containing recombinant seHAS or spHAS was analyzed by chromatography on a column (0.9×40 cm) of Sephacryl S500 HR (Pharmacia Biotech Inc.). Samples (0.4 ml in 200 mM NaCl, 5 mM Tris-HCl, pH 8.0, plus 0.5% SDS) were eluted with 200 mM, NaCl, 5 mM Tris-HCL, and pH 8.0 and 0.5 ml fractions were assessed for $^{14}$C and/or $^{3}$H radioactivity. Authenticity of the HA polysaccharide was assessed by treatment of a separate identical sample with the HA-specific hyaluronate lyase of Streptomyces hyalurolyticus (EC 4.2.2.1) at 37° C. for 3 hrs. The digest was then subjected to gel filtration.

C.8 SDS-PAGE and Western Blotting

SDS-PAGE was performed according to the Laemmli method. Electrotransfers to nitrocellulose were performed within standard blotting buffer with 20% methanol using a Bio-Rad mini Transblot device. The blots were blocked with 2% BSA in TBS. Protein A/G alkaline phosphatase conjugate (Pierce) and p-nitroblue tetrazolium/5-bromo4-chloro-3 indolyl phosphate p-toluidine salt were used for detection.

C.9 DNA Sequence and Analysis

Plasmids were sequenced on both strands using fluorescent labeled vector primers. Sequencing reactions were performed using a Thermosequenase™ kit for fluorescent labeled primers (with 7-deazaG). Samples were electrophoresed on a Pharmacia ALF Express DNA Sequencer and data were analyzed by the ALF Manager Software v3.02. Internal regions of inserts were sequenced with internal primers using the ABI Prism 377 (Software version 2.1.1). Ambiguous regions were sequenced manually using Sequenase™ 7-deaza—DNA polymerase, 7-deaza GTP master mix (USB) and [α-$^{35}$S] dATP (Amersham Life Sciences). The sequences obtained were compiled and analyzed using DNASIS, v2.1 (Hitachi Software Engineering Co., Ltd.). The nucleotide and amino acid sequences were compared with other sequences in the Genbank and other databases.

C.10 Identification of seHAS

Identification of seHAS was accomplished by utilizing a PCR approach with oligonucleotide primers based on several regions of high identity among spHAS, DG42 (now known to be a developmentally regulated X. laevis HAS and designated xlHAS) and NodC (a Rhizobium β-GlcNAc transferase). The xlHAS and NodC proteins are, respectively, ~50% and ~10% identical to spHAS. This strategy yielded a 459 bp PCR product whose sequence was 66.4% identical to spHAS, indicating that a Group C homologue (seHAS) of the Group A (spHAS) HA synthase gene had been identified. The complete coding region of the gene was then reconstructed using a similar PCR-based strategy. A final set of PCR primers was then used to amplify the complete ORF from genomic DNA. When this 1.2 kb PCR fragment was incorporated into the expression vector pKK223 and transformed into E. coli SURE cells, HA synthetic activity was demonstrated in isolated membranes from 5 of the 5 colonies tested.

The ORF of the reconstructed gene encodes a novel predicted protein of 417 amino acids that was not in the database and it is two amino acids shorter than spHAS. The two bacterial proteins are 72% identical and the nucleic acid sequences are 70% identical. The predicted molecular weight of the seHAS protein is 47,778 and the predicted isoelectric point is at pH 9.1. Recently identified mammalian HASs, such as the mouse and human isozymes (mHAS1, 2, 3, and hHAS1, 2, 3, respectively, in FIG. 2) are similar to the bacterial proteins. The overall identity between the two groups is ~28–31%, and in addition many amino acids in seHAS are highly conserved with those of the eukaryotic HASs (e.g., K/R or D/E substitutions). A98R, the PBCY-1 HAS is 28–33 percent identical to the mammalian HASs, and is predicted to have a similar topology in the lipid membrane. Within mammalian species the same family members are almost completely identical (e.g., muHAS1 and huHAS1 are 95% identical; muHAS2 and huHAS2 are 98% identical). However, and as shown in FIG. 3, even within the same species the different HAS family members are more divergent (e.g., muHAS1 and muHAS2 are 53% identical; muHAS1 and muHAS3 are 57% identical; muHAS2 and muHAS3 are 71% identical).

FIG. 11 shows the hydropathy plot for seHAS and predicted membrane topology. The hydrophilicity plot for the Streptococcal Group C HAS was generated by the method of Kyte and Doolittle (J. Mol. Biol. 157, 105, 1982) using DNASIS. The protein is predicted to be an integral membrane protein.

FIG. 12 shows a model for the topologic organization of seHAS in the membrane. The proposed topology for the protein conforms to the charge-in rule and puts the large central domain inside. This domain is likely to contain most of the substrate binding and catalytic functions of the enzyme. $Cys^{226}$ in seHAS, which is conserved in all HAS family members, as well as the other three cysteines are shown in the central domain. $Cys^{281}$ is a critical residue whose alteration can dramatically alter the size distribution of HA product synthesized by the enzyme.

The overall membrane topology predicted for seHAS is identical to that for spHAS and the eukaryotic HASs reported thus far. The protein has two putative transmembrane domains at the amino terminus and 2–3 membrane-associated or transmembrane domains at the carboxyl end. The hydropathy plots for the two Streptococcal enzymes are virtually identical and illustrate the difficulty in predicting the topology of the extremely hydrophobic region of ~90 residues at $K^{313}$-$R^{406}$ in seHAS ($K^{313}$-$K^{405}$ in spHAS).

seHAS was efficiently expressed in *E. coli* cells. Roughly 10% of the total membrane protein was seHAS as assessed by staining of SDS-PAGE gels (FIG. 5). The prominent seHAS band at 42 kD is quantitatively missing in the vector-only control lane. This unusually high level of expression for a membrane protein is also found for spHAS, using the same vector in SURE cells. About 8% of the membrane protein is spHAS in *E. coli* SURE cells. In contrast, the amount of seHAS in Group C membranes is not more than 1% of the total membrane protein. The spHAS in Group A membranes is barely detectable. The recombinant seHAS expressed in *E. coli* SURE cells does not synthesize HA in vivo, since these cells lack UDP-GlcUA, one of the required substrates. However, membranes containing the recombinant seHAS protein synthesize HA when provided with the substrates UDP-GlcNAc and UDP-GlcUA (FIG. 13).

FIG. 13 shows the synthesis of authentic HA by recombinant seHAS. *E. coli* membranes (69 µg) prepared from cells containing recombinant seHAS or vector alone were incubated at 37° C. for 1 hour with 700 µM UDP-[$^3$H] GlcNAc (2.78×10$^3$ dpm/nmol; □, ■) and 300 µM UDP-[$^{14}$C]GlcUA (3.83×10$^3$ dpm/nmol; ○, ●) in a final volume of 200 µl as described herein. The enzyme reaction was stopped by addition of EDTA to a final concentration of 25 mM. Half the reaction mix was treated with *Streptomyces* hyaluronidase at 37° C. for 3 hours. SDS (2%, w/v) was added to hyaluronidase-treated (○, □) and untreated (●, ■) samples, which were heated at 90° C. for 1 min. The samples were diluted to 500 µl with column buffer (5 mM Tris, 0.2 M NaCl, pH 8.0), clarified by centrifugation and 200 µl was injected onto a Sephacryl S-500 HR column. Fractions (1 ml) were collected and radioactivity was determined. BD is the peak elution position of blue dextran (~2×10$^6$ DA; Pharmacia). $V_o$ marks the excluded volume and $V_i$ the included volume. The ratio of [$^{14}$c] GlcUA: [$^3$H] GlcNAc incorporated into the total amount of HA fractionated on the column is 1.4, which is identical to the ratio of specific activities of the two substrates. Therefore, the molar ratios of the sugars incorporated into product is 1:1 as predicted for authentic HA. Membranes from cells transformed with vector alone did not synthesize HA.

Using 120 µM UDP-GlcUA and 300 µM UDP-GlcNAc, HA synthesis was linear with membrane protein (at ≦0.2 µg) and for at least 1 hour. Also, membranes prepared from nontransformed cells or cells transformed with vector alone have no detectable HAS activity. HA synthesis is negligible if Mg$^{+2}$ is chelated with EDTA (<5% of control) or if either of the two substrates are omitted (~2% of control). Recombinant seHAS also showed the expected specificity for sugar nucleotide substrates, being unable to copolymerize either UDP-GalA, UDP-Glc or UDP-GalNAc with either of the two normal substrates (Table II).

Based on gel filtration analysis, the average mass of the HA synthesized by seHAS in isolated membranes is 5–10×10$^6$ Da. The product of the recombinant seHAS is judged to be authentic HA based on the equimolar incorporation of both sugars and its sensitivity to degradation by the specific *Streptomyces* hyaluronidase (FIG. 13). Although the conditions for total HA synthesis were not optimal (since ~90% of one substrate was incorporated into product), the enzyme produced a broad distribution of HA chain lengths. The peak fraction corresponds to an HA mass of 7.5×10$^6$ Da which is a polymer containing approximately 36,000 monomeric sugars. The distribution of HA sizes resolved on this column ranged from 2–20×10$^6$ Da.

The deduced protein sequence of seHAS was confirmed by the ability of antibodies to the spHAS protein to cross-react with the Group C protein (FIG. 9). Polyclonal antibodies to the whole spHAS protein or to just the central domain of spHAS also reacted with the seHAS protein. Antipeptide antibody to the C-terminus of spHAS did not cross-react with this somewhat divergent region in the seHAS protein. However, antipeptide antibody directed against the spHAS sequence $E^{147}$-$T^{161}$ recognized the same predicted sequence in seHAS. The antipeptide antibody also reacts with the native seHAS and spHAS proteins in Streptococcal membranes and confirms that the native and recombinant enzymes from both species are of identical size. Like the spHAS protein, seHAS migrates anomalously fast on SDS-PAGE. Although the calculated mass is 47,778 Da, the $M_r$ by SDS-PAGE is consistently ~42 kDa.

Because of the sequence identity within their central domain regions and the overall identical structure predicted for the two bacterial enzymes, the peptide-specific antibody against the region $E^{147}$-$T^{161}$ can be used to normalize for HAS protein expression in membranes prepared from cells transformed with genes for the two different enzymes. Using this approach, membranes with essentially identical amounts of recombinant spHAS or seHAS were compared with respect to the initial rate of HA synthesis and the distribution of HA product size.

As shown for spHAS, the synthesis of HA chains by seHAS is processive. The enzymes appear to stay associated with a growing HA chain until it is released as a final product. Therefore, it is possible to compare the rates of HA elongation by seHAS and spHAS by monitoring the size distribution of HA chains produced at early times, during the first round of HA chain synthesis. Based on gel filtration analysis of HA product sizes at various times, we estimated that the average rate elongation by seHAS is about 9,000 monosaccharides/minute at 37° C. (FIG. 10). In five minutes, the enzymes can polymerize an HA chain of 5–10×10$^6$ Da. During a 60 min incubation, therefore, each enzyme molecule could potentially initiate, complete and release on the order of 5–8 such large HA molecules. At early times (e.g., ≦1 min), reflecting elongation of the first HA chains, the size distribution of HA produced by seHAS was shifted to larger species compared to spHAS. By 60 min the two distributions of HA product sizes are indistinguishable.

The cloned seHAS represents the authentic Group C HA synthase. Previously reported or disclosed "Group C" proteins are, therefore, not the true Group C HAS. The seHAS protein is homologous to nine of the currently known HA synthases from bacteria, vertebrates, and a virus that now comprise this rapidly growing HA synthase family. This homology is shown particularly in FIG. 2. In mammals three genes, designated HAS1, HAS2 and HAS3, have been identified and mapped to three different chromosomes in both human and mouse. In amphibians the only HAS protein identified thus far is the developmentally regulated DG42, which was cloned in 1988 and recently shown to encode the HA synthase activity by analysis of the recombinant protein in yeast membranes. Probably other *X. laevis* HAS genes will soon be identified.

A divergent evolution model suggests that a primitive bacterial HAS precursor may have been usurped early during vertebrate development, or the bacterial pathogenic strategy of making an HA capsule was developed when a primitive bacteria captured a primordial HAS. Convergent evolution of the bacterial and eukaryotic HAS enzymes to a common structural solution seems unlikely, but may have occurred.

At least ten identified HAS proteins are predicted to be membrane proteins with a similar topology. HA synthesis occurs at the plasma membrane and the HA is either shed into the medium or remains cell associated to form the bacterial capsule or a eukaryotic pericellular coat. The sugar nucleotide substrates in the cytoplasm are utilized to assemble HA chains that are extruded through the membrane to the external space.

The protein topology in the very hydrophobic carboxyl portion of the HAS protein appears to be critical in understanding how the enzymes extend the growing HA chain as it is simultaneously extruded through the membrane. For example, the unprecedented enzymatic activity may require unusual and complex interactions of the protein with the lipid bilayer. Preliminary results based on analysis of spHAS-alkaline phosphatase fusion proteins indicate that the amino and carboxyl termini and the large central domains are all intracellular, as shown in FIGS. 11 and 12. The seHAS protein also contains a large central domain (~63% of the total protein) that appears to contain the two substrate binding sites and the two glycosyltransferase activities needed for HA synthesis. Although current software programs cannot reliably predict the number or nature of membrane-associated domains within the long C-terminal hydrophobic stretch, the proposed topological arrangement agrees with the present evidence and applies as well to the eukaryotic enzymes, which are ~40% larger primarily due to extension of the C-terminal end of the protein with 2 additional predicted transmembrane domains.

Four of the six Cys residues in spHAS are conserved with seHAS. Only Cys225 in spHAS and Cys224 in seHAS is conserved in all members of the HAS family. Since sulfhydryl reactive agents, such as p-mercurobenzoate or NEM, greatly inhibit HAS activity, it is likely that this conserved Cys is necessary or important for enzyme activity. Initial results from site-directed mutagenesis studies, however, indicate that a C225S mutant of spHAS is not inactive, it retains 5–10% of wildtype activity.

The recognition of nucleic acid sequences encoding only seHAS, only spHAS, or both seHAS and spHAS using specific oligonucleotides is shown in FIG. 14. Three pairs of sense-antisense oligonucleotides were designed based on the sequence of SEQ ID NO:1 and the coding sequence for spHAS. The seHAS based nucleic acid segments (se1-se2 and sesp1-sesp2, SEQ ID NOS:3–6, respectively) are indicated in FIG. 15. These three oligonucleotide pairs were hybridized undertypical PCR reactions with genomic DNA from either Group C (seHAS) (lanes 2, 4, and 6) or Group A (spHAS) (lanes 3, 5, and 7) streptococci. Lanes 1 and 8 indicate the positions of MW standards in kb (kilobases). The PCR reactions were performed using Taq DNA polymerase (from Promega) for 25 cycles as follows: 94 degrees Celsius for 1 minute to achieve DNA denaturation, 48 degrees Celsius (42 degrees Celsius for the smaller common sesp primers) for 1 minute to allow hybridization, and 72 degrees Celsius for 1.5 minutes for DNA synthesis. The PCR reaction mixtures were then separated by electrophoresis on a 1% agarose gel.

The se1-se2 primer pair was designed to be uniquely specific for the Group C HAS (seHAS). The sp1-sp2 primer pair was designed to be uniquely specific for the Group A HAS (spHAS). The sesp1-sesp2 primer pair was designed to hybridize to both the Group A and Group C HAS nucleic acid sequences. All three primer pairs behaved as expected, showing the appropriate ability to cross-hybridize and support the generation of PCR products that were specific and/or unique.

The oligonucleotides used for specific PCR or hybridization are shown in FIG. 15. Corresponding regions of SEQ ID NO:1 are indicated for each of the synthetic oligonucleotides of SEQ ID NOS: 3, 4, 5, and 6. Each of the four oligonucleotides will hybridize specifically with the seHAS sequence and the appropriate pairs of sense/antisense primers are suitable for use in the polymerase chain reaction as shown in FIG. 14.

Expression of seHAS in *Bacillus subtilis*

FIGS. 16A and 16B demonstrate recombinant HA production from seHAS in a *Bacillus subtilis* strain, *B. subtilis* 168, as evidenced by gel filtration chromatography. FIG. 16A is a plot that compares production of HA in *Bacillus subtilis* 168 transformed with pSM143 vector alone to a *Bacillus subtilis* 168 transformed with pSM143 containing seHAS. The production of HA can be visualized by the peak between about 13.5 minutes to about 16 minutes. FIG. 16B is an enlargement of this peak to omit the large peak caused by radiolabeled protein and sugar that was not incorporated into HA, which can be seen between about 16.5 minutes to about 20 minutes in FIG. 16A.

Gel Filtration Analysis of Recombinant HA Production by spHAS in *Bacillus subtilis*

FIG. 17A demonstrates nutritional control of the size distribution of recombinant HA produced by spHAS in *Bacillus subtilis*. *Bacillus subtilis* 168 (pPD41Δ5), encoding the spHAS enzyme, was cultured in Luria Bertani broth (LB) and produced HA that eluted out of the gel filtration column at an earlier time point (peaking at 13.48 minutes) than the same strain cultured in Spizzizens media (Sp) (peaking at about 14.43 minutes). These two cultures were grown in parallel, but larger HA is produced by the bacteria grown in LB. Radioactivity of the tritiated HA is quantitated by disintegration per second (DPS). This negative control show that normally *B. subtilis* does not produce HA. The HA peak made by *B. subtilis* transformed with spHAS is sensitive to the specific HA lyase but not protease.

Therefore, one can alter the molecular weight of HA produced in a recombinant host cell by varying the media in which the host cell is grown. For example, by growing the recombinant host cell in a complex media, such as LB (Luria-Bertani), Terrific Broth, NZCYM, SOB, SOC or 2xYT media, a larger molecular weight HA molecule will be produced as compared to HA produced by a recombinant host cell grown on a chemically defined media, such as Spizzizens media or M9 minimal media. The size of HA can also be varied by the carbon source supplied, such as glucose.

FIG. 17B shows the resulting difference in peak appearance when utilizing the *Bacillus subtilis* 168 containing spHAS and the *Bacillus subtilis* that contains the vector alone.

Media samples obtained after in vivo labeling of *Bacillus subtilis* with $^3$H glucosamine were analyzed by gel filtration analysis. By utilizing this method, it is possible to determine relative size and amount of hyaluronic acid (HA) produced by the bacteria. All samples were clarified by centrifugation at 16,000×g for 5 minutes prior to gel filtration. Radioactive components were detected with a LB508 Radioflow Detector (EG & G Berthold) and Zinsser cocktail (1.8 ml/min).

The size of HA polymers was analyzed by chromatography on a Phenomenex PolySep-GFC-P 5000 or 6000 column (300×7.8 mm) eluted with 0.2 M sodium nitrate at 0.6 ml/min on a Waters 600E system. The columns were standardized with various size dextrans (580, 145, 50, and 20 kDa) or MANT-labeled HA (DeAngelis, 2001) with average molecular weights of 600 and 80 kDa by MALLS. For the MALLS, the HA polymers (100 μg) were first loaded on two tandem Toso Biosep TSK-GEL columns (6000PWXL followed by 4000PWXL; each 7.8 mm 30 cm; Japan) and eluted in 50 mM sodium phosphate, 150 mM NaCl, pH 7 at 0.5 ml/min. The eluant flowed through an Optilab DSP interferometric refractometer and then a Dawn DSF laser photometer (632.8 nm; Wyatt Technology, Santa Barbara, Calif.) in the multi-angle mode. The manufacturer's software package was used to determine the absolute average molecular weight using a dn/dC coefficient of 0.153.

The HA standards were made by sub-stoichiometric labeling (1 MANT/~50 monosaccharides) of hydroxyl groups on the streptococcal HA polysaccharide with N-methylisatoic anhydride. The 600 kDa standard was obtained by subfractionation of bulk HA using preparative HPLC. Extended ultrasonication (2 minute intervals for 30 minutes total, 1 % acetone in water, on ice) of the bulk HA with a Heat Systems-Ultrasonic W-380 sonicator with a microtip (power setting 4) was used to produce the 80 kDa standard.

Heterologous Expression of *P. multocida* HAS

The PmHAS ORF in the pPm7A insert was amplified by 13 cycles of PCR with Taq polymerase (Fisher) and primers corresponding to the sequence near the deduced amino and carboxyl termini (codons in capitals: sense, 5'-gcgaattcaaag-gacagaaaATGAAcACATTATCACAAG-3', and antisense, 5'-gggaattctgcagttaTAGAGTTATACTATTAATAATGAAC-3'; start and stop codons, respectively, in bold). Codon 2 (T to C) was altered (italic lowercase) to increase protein production in *E. coli*. The primers also contained EcoRI and PstI restriction sites (underlined) to facilitate cloning into the expression plasmid pKK223-3 (tac promoter; Pharmacia). The resulting recombinant construct, pPmHAS, was transformed into *E. coli* SURE cells (Stratagene), and this strain was used as the source of membrane preparations for in vitro HAS assays. Log phase cultures (LB broth, 30° C.) were induced with 0.5 mM isopropylthiogalactoside for 3 hours before harvest. The plasmid was also transformed into *E. coli* K5; the resulting strain was examined for the presence of capsule by light microscopy and buoyant density centrifugation. The K5 bacterial cultures were not induced routinely as IPTG addition did not increase HA levels in LB or defined media significantly. The K5 bacteria are useful foreign hosts because they contain polysaccharide transport proteins and machinery that interact with pmHAS during HA synthesis; these proteins facilitate HA transport out of the cell.

Membranes derived from *E. coli* SURE cells containing the pPmHAS plasmid, but not samples from cells with the vector pKK223-3 alone, synthesized HA in vitro when supplied with both UDP-GlcUA and UDP-GlcNAc (25 vs. *1.5 pMol GlcUA transfer [mg of protein]-1[hr]-1, respectively). No incorporation of [$^{14}$C]GlcA was observed if UDP-GlcNAc was omitted or if divalent metal ions were chelated with EDTA. The HAS activity derived from recombinant HAS was similar to the enzyme obtained from wild-type *P. multocida* membranes as $Mn^{2+}$ stimulated at least ten-fold more activity than $Mg^{2+}$.

Cultures of recombinant *E. coli* were also tested for the presence of HA polysaccharide with a radiometric assay utilizing labeled HA-binding protein. *E. coli* K5 with pPmHAS produced 460 μg/ml HA per A600. K5 cells with pKK223–3 vector alone did not produce HA (*0.01 μg/ml HA per A600). For comparison, wild-type *P. multocida* P-1059 grown in the same media produced 1,100 μg/ml HA per A600. *E. coli* K5 with pPmHAS produced such high levels of HA that the cells became encapsulated (FIG. 18A). The radius of the capsule of the recombinant strain was ~0.2–0.5 μm (assuming a bacterial cell width of 0.5 μm). This capsule could be removed by treatment with either ovine testicular hyaluronidase or *Streptomyces* HA lyase (FIG. 18B). Neither the native K5 host strain nor transformants containing pKK223–3 vector possessed a readily observable capsule as determined by light microscopy. K5 cells with pPmHAS were also deemed encapsulated by buoyant density centrifugation. The recombinant cells floated on top of the 58% Percoll cushion, while the vector control cells or hyaluronidase-treated recombinant cells pelleted through the Percoll cushion (not shown).

Role of Glycosyltransferases in Transport During Capsular Biosynthesis

Glycosyltransferases catalyze the formation of the repeating GAG backbone, but in certain cases, these same polypeptides may also play roles in transporting the polymer across the cell membrane. The Gram-positive Group A and C *Streptococcus* possess only one lipid membrane and the capsule operon encodes the synthase and two enzymes for UDP-GlcUA production, UDP-glucose dehydrogenase and UDP-glucose pyrophosphorylase (~4 kilobases of DNA; Crater and van de Rijn, 1995). Topological analyses of a series of streptococcal spHAS fusion proteins containing reporter enzymes indicate that this synthase spans the bilayer at least four times and is intimately associated with the membrane (Heldermon et al., 2001) (FIG. 19). From biochemical and biophysical analyses, it appears that a complex composed of a monomer of the spHAS or seHAS polypeptide and ~16 lipid molecules catalyzes the transfer of both UDP-sugars to the nascent HA chain (Tlapak-Simmons et al., 1998). It was speculated that spHAS or seHAS, small integral membrane polypeptides, would require the assistance of the lipids to facilitate transport of the growing HA polymer chain across the hydrophobic core of the bilayer by creating a protein/lipid pore.

On the other hand, the Gram-negative bacteria capable of GAG biosynthesis, *Escherichia coli* and *Pasteurella multocida*, possess two lipid membranes, and their capsule loci encode many transport-associated proteins in addition to the glycosyltransferases and the UDP-GlcUA forming enzymes (~10–18 kilobases; Roberts, 1996; Townsend et al., 2001). Although many details are not well understood, in the best-studied model, the *E. coli* Group II capsular system, it appears that transport of the nascent polymer chain requires an apparatus composed of at least 7 distinct polypeptide species (Whitfield and Roberts, 1999; Silver et al., 2001). Briefly, a complex containing KpsC,M,S,T assembles on the inner membrane and interacts with the KfiA, B, C catalytic complex. KpsM and T form the ATP-binding cassette (ABC) transporter. A periplasmic protein, KpsD, and a dimer of another inner membrane protein, KpsE, help transport the polymer across the periplasmic space (Arrecubieta, 2001). A porin complex in the outer membrane is recruited to transport the growing polysaccharide chain out of the cell.

Certain Kps mutants polymerize the capsular polysaccharide chain, but possess faulty translocation resulting in polymer accumulation in the cytoplasm or periplasm. *P. multocida* is also thought to have a Group II-like transport system based on the sequence similarities and gene arrangement of its putative transport proteins to the *E. coli* proteins.

In the case of pmHAS and pmCS, the carboxyl-terminal tail is likely to contain a docking segment that interacts with the transport mechanism (Jing and DeAngelis, 2000) (FIG. 19), which is expressly incorporated herein in its entirety.

*Streptococcus uberis* HAS

FIG. 21 illustrates the PCR amplification of the HAS gene from four separate mucoid colonies of *S. uberis*. For each sample, a band was apparent at the expected size of about 1.25 kb, corresponding to the complete reading frame of suHAS plus restriction sites that were added by the PCR amplification.

FIG. 22 illustrates HA synthase activity from *S. pyogenes, S. equisimilis,* and *S. uberis*.

Other Identified HAS Sequences

In addition to the HAS sequences which have been disclosed herein and illustrated in the alignment of FIG. 2, other HAS sequences have been identified that may be utilized in the methods of production of HA in a *Bacillus* species of the present invention. For example, SEQ ID NOS:15 and 16 disclose the nucleotide and amino acid sequences, respectively, for an HA synthase found in the archaebacteria *Sulfolobus solfactaricus*. The isolation of this HA synthase from an extremophile provides a HAS having better stability and faster kinetics than the HA synthases previously described herein due to its ability to function in high temperatures, i.e., about 75° C.

A group of genes similar to the Streptococcal hasABC operon has been identified in the *Bacillus anthracis* plasmid pXO1, which harbors the anthrax toxin genes. However, the order of the genes in pXO1 are A, C, B. The complete sequence for the pXO1 plasmid is under Accession No. AF065404, and the sequence similar to hasA is ORF 93 of this sequence and starts at 111374 and stops at 112474. SEQ ID NOS:17 and 18 represent the nucleotide and amino acid sequences, respectively, of the gene similar to hasA identified in *B. anthracis* pXO1. There are no reports of a polysaccharide capsule in *B. anthracis,* and therefore Okinaka et al, the group that identified these genes, believes that pXO1 ORFs 93, 94 and 95 are examples of nonfunctional genes that have yet to decay away (*J. Bacteriol.* 181:6509 (1999)).

A third putative HAS has been identified in a virus that infects the brown algae *Ectocarpus siliculosus*. The amino acid and nucleotide sequences can be found in SEQ ID NOS:19 and 20, respectively. This case is probably similar to the cvHAS of PBCV-1 virus.

One method of demonstrating HA synthase activity (native or recombinant) for any putative HA synthase involves growing the bacteria in liquid culture, extracting the polysaccharide fraction (i.e., cationic detergent precipitation/high salt extraction/alcohol precipitation/redissolve in water/solvent extraction/alcohol precipitation), and analysis of the monosaccharide composition after acid hydrolysis. Further analysis includes agarose gel electrophoresis of intact polymers and enzyme-treated samples (HA lyase, chondroitinase, etc.). Also, biological assay using specific HA binding proteins in an ELISA or competition format are useful. To test for enzyme, membranes are prepared from cells, various UDP-sugar substrates are provided and then incorporation into polymer is analyzed, followed by chromatography and/or electrophoresis. Heterologous expression is observed by preparing a gene cassette using PCR with primers and genomic DNA that allows for cloning the ORF into an expression vector. Various hosts can be transformed with such vector, and the resulting recombinant cells can be analyzed for polysaccharide and/or enzyme as described herein previously.

Thus it should be apparent that there has been provided in accordance with the present invention a recombinant host cell having a purified nucleic acid segment having a coding region encoding enzymatically active HAS introduced therein, as well as methods of producing hyaluronic acid from the recombinant host cell, that fully satisfies the objectives and advantages set forth above. Although the invention has been described in conjunction with specific embodiments thereof, it is evident that many alternatives, modifications, and variations will be apparent to those skilled in the art. Accordingly, it is intended to embrace all such alternatives, modifications, and variations that fall within the spirit and broad scope of the appended claims.

What is claimed is:

1. A recombinant host cell, wherein the recombinant host cell is a *Bacillus* cell comprising a recombinant vector comprising a purified nucleic acid segment having a coding region encoding enzymatically active hyaluronan synthase, wherein the coding region is under control of a promoter, and wherein the coding region encoding enzymatically active hyaluronan synthase is selected from the group consisting of:
- (a) a coding region encoding enzymatically active hyaluronan synthase of SEQ ID NO:16;
- (b) a coding region encoding enzymatically active hyaluronan synthase of SEQ ID NO:8;
- (c) a nucleotide sequence in accordance with SEQ ID NO:15;
- (d) a nucleotide sequence in accordance with SEQ ID NO:7;
- (e) a coding region encoding enzymatically active hyaluronan synthase that is at least 70% identical to SEQ ID NO:14; and
- (f) a coding region encoding enzymatically active hyaluronan synthase, wherein the coding region is capable of hybridizing to a complementary sequence of SEQ ID NO:13.

2. The recombinant host cell of claim 1, wherein the recombinant host cell is a *Bacillus subtilis* or a *Bacillus licheniformis* cell.

3. The recombinant host cell of claim 1, wherein the host cell produces hyaluronic acid.

4. The recombinant host cell of claim 1, wherein the coding region encoding enzymatically active hyaluronan synthase of the purified nucleic acid segment is under control of a Gram positive bacterial-compatible promoter.

5. The recombinant host cell of claim 4, wherein the promoter is a *Bacillus* compatible promoter.

6. The recombinant host cell of claim 1, wherein the *Bacillus subtilis* cell further comprises a recombinant vector comprising a purified nucleic acid segment having a coding region encoding an enzymatically active UDP-GlcUA biosynthetic pathway enzyme, wherein the enzymatically active UDP-GlcUA biosynthetic pathway enzyme is selected from the group consisting of UDP-glucose dehydrogenase, UDP-glucose pyrophosphorylase, and combinations thereof.

7. The recombinant host cell of claim 1, wherein the recombinant vector further comprises a purified nucleic acid segment having a coding region encoding enzymatically active UDP-glucose dehydrogenase.

8. The recombinant host cell of claim 7, wherein the coding region encoding enzymatically active hyaluronan synthase and the coding region encoding enzymatically active UDP-glucose dehydrogenase are under the control of different promoters.

9. The recombinant host cell of claim 1, wherein the recombinant host cell has enhanced production of at least one of UDP-GlcUA and UDP-GlcNAc.

10. The recombinant host cell of claim 9, wherein the recombinant host cell further includes at least one modified RNA polymerase promoter wherein, when the modified RNA polymerase promoter is recognized by an RNA polymerase, the RNA polymerase is capable of expressing RNA in an amount greater than an endogenous RNA polymerase promoter.

11. The recombinant host cell of claim 10, wherein the modification is a mutation.

12. The recombinant host cell of claim 10, wherein the modification is tandem promoter elements.

13. The recombinant host cell of claim 9, wherein the recombinant host cell further includes at least one additional messenger RNA stabilizing element than is found in a native *Bacillus* cell.

14. The recombinant host cell of claim 9, wherein the recombinant host cell further includes at least one less messenger RNA destabilizing element than is found in a native *Bacillus* cell.

15. The recombinant host cell of claim 9, wherein the recombinant host cell further includes at least one nucleic acid segment having a coding region encoding a functionally active enzyme in a UDP-sugar precursor biosynthesis pathway such that the recombinant host cell has an activity greater than a native host cell expressing an endogenous UDP-sugar precursor biosynthesis pathway enzyme.

16. The recombinant host cell of claim 9, wherein the recombinant host cell further includes at least one mutated UDP-sugar precursor biosynthesis gene, wherein the mutated UDP-sugar precursor gene increases a half-life of a transcribed messenger RNA.

17. The recombinant host cell of claim 9, wherein the recombinant host cell further includes at least one mutated UDP-sugar precursor biosynthesis gene encoding a messenger RNA having an increased translational efficiency.

18. The recombinant host cell of claim 17, wherein the mutation in the UDP-sugar precursor biosynthesis gene occurs in a ribosome binding site in the UDP-sugar precursor biosynthesis gene such that a ribosome has an increased binding affinity for the ribosome binding site.

19. A method for producing hyaluronic acid, comprising the steps of:
- introducing a purified nucleic acid segment having a coding region encoding enzymatically active hyaluronan synthase into a *Bacillus* host wherein the coding region is under control of a promoter, and wherein the coding region encoding enzymatically active hyaluronan synthase is selected from the group consisting of:
  - (a) a coding region encoding enzymatically active hyaluronan synthase of SEQ ID NO:16;
  - (b) a coding region encoding enzymatically active hyaluronan synthase of SEQ ID NO:8;
  - (c) a nucleotide sequence in accordance with SEQ ID NO:15;
  - (d) a nucleotide sequence in accordance with SEQ ID NO:7;
  - (e) a coding region encoding enzymatically active hyaluronan synthase that is at least 70% identical to SEQ ID NO:14; and (f) a coding region encoding enzymatically active hyaluronan synthase, wherein the coding region is capable of hybridizing to a complementary sequence of SEQ ID NO:13;

growing the *Bacillus* host in a medium to secrete hyaluronic acid; and recovering the secreted hyaluronic acid.

20. The method of claim 19, wherein the *Bacillus* host is *Bacillus subtilis* or *Bacillus licheniformis*.

21. The method according to claim 19, wherein the step of recovering the secreted hyaluronic acid comprises extracting the secreted hyaluronic acid from the medium.

22. The method according to claim 21, further comprising the step of purifying the extracted hyaluronic acid.

23. The method of claim 19, further comprising the step of introducing a purified nucleic acid segment having a coding region encoding enzymatically active UDP-glucose dehydrogenase into the *Bacillus* host.

24. The method of claim 23, wherein the coding region encoding enzymatically active hyaluronan synthase and the coding region encoding enzymatically active UDP-glucose dehydrogenase are under the control of the same promoter.

25. The method of claim 23, wherein the coding region encoding enzymatically active hyaluronan synthase and the coding region encoding enzymatically active UDP-glucose dehydrogenase are under the control of different promoters.

26. The method of claim 19, wherein, in the step of introducing a purified nucleic acid segment having a coding region encoding enzymatically active hyaluronan synthase into a *Bacillus* host, the coding region encoding enzymatically active hyaluronan synthase of the purified nucleic acid segment is under control of a Gram positive bacterial-compatible promoter.

27. The method of claim 26, wherein the promoter is a *Bacillus*-compatible promoter.

28. The method of claim 19 wherein, in the step of introducing a purified nucleic acid segment having a coding region encoding enzymatically active hyaluronan synthase into a *Bacillus* host, the *Bacillus* host has an enhanced production of at least one of UDP-GlcUA and UDP-GlcNAc.

29. The method of claim 28 wherein, in the step of introducing a purified nucleic acid segment having a coding region encoding enzymatically active hyaluronan synthase into a *Bacillus* host, the *Bacillus* host further includes at least one modified RNA polymerase promoter having an increased promoter activity.

30. The method of claim 29, wherein the modification of the RNA polymerase promoter is a mutation.

31. The method of claim 29, wherein the modification of the RNA polymerase promoter is tandem promoter elements.

32. The method of claim 28 wherein, in the step of introducing a purified nucleic acid segment having a coding region encoding enzymatically active hyaluronan synthase into a *Bacillus* host, the *Bacillus* host further includes at least one additional messenger RNA stabilizing element than is found in a native *Bacillus* host.

33. The method of claim 28 wherein, in the step of introducing a purified nucleic acid segment having a coding region encoding enzymatically active hyaluronan synthase into a *Bacillus* host, the *Bacillus* host further includes at least one less messenger RNA destabilizing element than is found in a native *Bacillus* host.

34. The method of claim 28 wherein, in the step of introducing a purified nucleic acid segment having a coding region encoding enzymatically active hyaluronan synthase into a *Bacillus* host, the *Bacillus* host further includes at least one nucleic acid segment having a coding region encoding a UDP-sugar precursor biosynthesis pathway enzyme such that the recombinant host cell has an activity greater than a native host cell expressing an endogenous UDP-sugar precursor biosynthesis pathway enzyme.

35. The method of claim 28 wherein, in the step of introducing a purified nucleic acid segment having a coding region encoding enzymatically active hyaluronan synthase into a *Bacillus* host, the *Bacillus* host comprises at least one mutated endogenous UDP-sugar precursor biosynthesis gene wherein the mutation results in an increase of a half-life of a messenger RNA transcribed from the mutated UDP-sugar precursor gene.

36. The method of claim 19 wherein, in the step of introducing a purified nucleic acid segment having a coding region encoding enzymatically active hyaluronan synthase into a *Bacillus* host, the *Bacillus* host comprises at least one mutated UDP-sugar precursor biosynthesis gene encoding a messenger RNA having an increased translational efficiency.

37. The method according to claim 36, wherein the mutation in the UDP-sugar precursor biosynthesis gene occurs in a ribosome binding site in the UDP-sugar precursor biosynthesis gene such that a ribosome has an increased binding affinity for the ribosome binding site.

* * * * *

UNITED STATES PATENT AND TRADEMARK OFFICE
CERTIFICATE OF CORRECTION

PATENT NO. : 7,229,796 B2  Page 1 of 1
APPLICATION NO. : 11/474663
DATED : June 12, 2007
INVENTOR(S) : Paul DeAngelis et al.

It is certified that error appears in the above-identified patent and that said Letters Patent is hereby corrected as shown below:

In the Specification:
Column 3, line 47: Delete "Triscoft" and replace with -- Triscott --.

Column 6, line 51: After "motif" insert a closed parantheses -- ) --.

Signed and Sealed this

First Day of April, 2008

JON W. DUDAS
*Director of the United States Patent and Trademark Office*

UNITED STATES PATENT AND TRADEMARK OFFICE
CERTIFICATE OF CORRECTION

PATENT NO.       : 7,229,796 B2                                        Page 1 of 1
APPLICATION NO.  : 11/474663
DATED            : June 12, 2007
INVENTOR(S)      : Paul De Angelis, Paul H. Weigel and Kshama Kumari It is certified that error appears in the above-identified patent and that said Letters Patent is hereby corrected as shown below:

On the Title Page, item 73: Add the following Assignee -- The Board of Regents of the University of Oklahoma, The 1000 Stanton L. Young Blvd., Room 121, Oklahoma City, Oklahoma 73114 --.

Signed and Sealed this

Fourth Day of November, 2008

JON W. DUDAS
*Director of the United States Patent and Trademark Office*

UNITED STATES PATENT AND TRADEMARK OFFICE
CERTIFICATE OF CORRECTION

PATENT NO. : 7,229,796 B2
APPLICATION NO. : 11/474663
DATED : June 12, 2007
INVENTOR(S) : Paul H. Weigel, Paul L. DeAngelis and Kshama Kumari It is certified that error appears in the above-identified patent and that said Letters Patent is hereby corrected as shown below:

Column 1, lines 36-38: Delete entirety of paragraph and replace with -- This invention was made with government support under Contract Number GM035978 awarded by the National Institutes of Health. The government has certain rights in the invention. --

Signed and Sealed this

Fifth Day of October, 2010

David J. Kappos
*Director of the United States Patent and Trademark Office*

SEQUENCE LISTING

<160> NUMBER OF SEQ ID NOS: 20

<210> SEQ ID NO 1
<211> LENGTH: 1254
<212> TYPE: DNA
<213> ORGANISM: Streptococcus equisimilis

<400> SEQUENCE: 1

```
atgagaacat taaaaaacct cataactgtt gtggccttta gtatttttttg ggtactgttg      60 atttacgtca atgtttatct ctttggtgct aaaggaagct tgtcaatttta tggcttttttg     120 ctgatagctt acctattagt caaaatgtcc ttatccttttt tttacaagcc atttaaggga     180
agggctgggc aatataaggt tgcagccatt attccctctt ataacgaaga tgctgagtca     240
```

```
ttgctagaga ccttaaaaag tgttcagcag caaacctatc ccctagcaga aatttatgtt      300
gttgacgatg gaagtgctga tgagacaggt attaagcgca ttgaagacta tgtgcgtgac      360
actggtgacc tatcaagcaa tgtcattgtt catcggtcag agaaaaatca aggaaagcgt      420
catgcacagg cctgggcctt tgaaagatca gacgctgatg tcttttttgac cgttgactca     480 gatacttata tctaccctga tgctttagag gagttgttaa aaacctttaa tgacccaact      540 gttttttgctg cgacgggtca ccttaatgtc agaaatagac aaaccaatct cttaacacgc     600
ttgacagata ttcgctatga taatgctttt ggcgttgaac gagctgccca atccgttaca     660
ggtaatatcc ttgtttgctc aggtccgctt agcgtttaca dacgcgaggt ggttgttcct     720
aacatagata gatacatcaa ccagaccttc ctgggtattc ctgtaagtat tggtgatgac     780
aggtgcttga ccaactatgc aactgattta ggaaagactg tttatcaatc cactgctaaa     840
tgtattacag atgttcctga caagatgtct acttacttga agcagcaaaa ccgctggaac     900
aagtccttct ttagagagtc cattatttct gttaagaaaa tcatgaacaa tccttttgta     960
gccctatgga ccatacttga ggtgtctatg tttatgatgc ttgtttattc tgtggtggat     1020
ttctttgtag gcaatgtcag agaatttgat tggctcaggg ttttagcctt tctggtgatt    1080
atcttcattg ttgccctgtg tcggaacatt cattacatgc ttaagcaccc gctgtccttc    1140
ttgttatctc cgttttatgg ggtgctgcat ttgtttgtcc tacagccctt gaaattatat    1200 tctctttta ctattagaaa tgctgactgg ggaacacgta aaaaattatt ataa            1254
```

<210> SEQ ID NO 2
<211> LENGTH: 417
<212> TYPE: PRT
<213> ORGANISM: Streptococcus equisimilis

<400> SEQUENCE: 2

```
Met Arg Thr Leu Lys Asn Leu Ile Thr Val Val Ala Phe Ser Ile Phe
1               5                   10                  15

Trp Val Leu Leu Ile Tyr Val Asn Val Tyr Leu Phe Gly Ala Lys Gly
            20                  25                  30

Ser Leu Ser Ile Tyr Gly Phe Leu Leu Ile Ala Tyr Leu Leu Val Lys
        35                  40                  45

Met Ser Leu Ser Phe Phe Tyr Lys Pro Phe Lys Gly Arg Ala Gly Gln
    50                  55                  60

Tyr Lys Val Ala Ala Ile Ile Pro Ser Tyr Asn Glu Asp Ala Glu Ser
65                  70                  75                  80

Leu Leu Glu Thr Leu Lys Ser Val Gln Gln Gln Thr Tyr Pro Leu Ala
                85                  90                  95

Glu Ile Tyr Val Val Asp Asp Gly Ser Ala Asp Glu Thr Gly Ile Lys
            100                 105                 110

Arg Ile Glu Asp Tyr Val Arg Asp Thr Gly Asp Leu Ser Ser Asn Val
        115                 120                 125

Ile Val His Arg Ser Glu Lys Asn Gln Gly Lys Arg His Ala Gln Ala
    130                 135                 140

Trp Ala Phe Glu Arg Ser Asp Ala Asp Val Phe Leu Thr Val Asp Ser
145                 150                 155                 160

Asp Thr Tyr Ile Tyr Pro Asp Ala Leu Glu Glu Leu Leu Lys Thr Phe
                165                 170                 175

Asn Asp Pro Thr Val Phe Ala Ala Thr Gly His Leu Asn Val Arg Asn
            180                 185                 190
```

```
Arg Gln Thr Asn Leu Leu Thr Arg Leu Thr Asp Ile Arg Tyr Asp Asn
        195                 200                 205

Ala Phe Gly Val Glu Arg Ala Ala Gln Ser Val Thr Gly Asn Ile Leu
    210                 215                 220

Val Cys Ser Gly Pro Leu Ser Val Tyr Arg Arg Glu Val Val Val Pro
225                 230                 235                 240

Asn Ile Asp Arg Tyr Ile Asn Gln Thr Phe Leu Gly Ile Pro Val Ser
                245                 250                 255

Ile Gly Asp Asp Arg Cys Leu Thr Asn Tyr Ala Thr Asp Leu Gly Lys
            260                 265                 270

Thr Val Tyr Gln Ser Thr Ala Lys Cys Ile Thr Asp Val Pro Asp Lys
        275                 280                 285

Met Ser Thr Tyr Leu Lys Gln Gln Asn Arg Trp Asn Lys Ser Phe Phe
    290                 295                 300

Arg Glu Ser Ile Ile Ser Val Lys Lys Ile Met Asn Asn Pro Phe Val
305                 310                 315                 320

Ala Leu Trp Thr Ile Leu Glu Val Ser Met Phe Met Met Leu Val Tyr
                325                 330                 335

Ser Val Val Asp Phe Phe Val Gly Asn Val Arg Glu Phe Asp Trp Leu
            340                 345                 350

Arg Val Leu Ala Phe Leu Val Ile Ile Phe Ile Val Ala Leu Cys Arg
        355                 360                 365

Asn Ile His Tyr Met Leu Lys His Pro Leu Ser Phe Leu Leu Ser Pro
    370                 375                 380

Phe Tyr Gly Val Leu His Leu Phe Val Leu Gln Pro Leu Lys Leu Tyr
385                 390                 395                 400

Ser Leu Phe Thr Ile Arg Asn Ala Asp Trp Gly Thr Arg Lys Lys Leu
                405                 410                 415

Leu

<210> SEQ ID NO 3
<211> LENGTH: 22
<212> TYPE: DNA
<213> ORGANISM: Sreptococcus equisimilis

<400> SEQUENCE: 3
gctgatgaga caggtattaa gc                                          22

<210> SEQ ID NO 4
<211> LENGTH: 20
<212> TYPE: DNA
<213> ORGANISM: Streptococcus equisimilis

<400> SEQUENCE: 4
atcaaattct ctgacattgc                                             20

<210> SEQ ID NO 5
<211> LENGTH: 20
<212> TYPE: DNA
<213> ORGANISM: Streptococcus equisimilis

<400> SEQUENCE: 5
gactcagata cttatatcta                                             20

<210> SEQ ID NO 6
<211> LENGTH: 17
<212> TYPE: DNA
<213> ORGANISM: Streptococcus equisimilis
```

<400> SEQUENCE: 6 ttttacgtg ttccca                                                        17

<210> SEQ ID NO 7
<211> LENGTH: 567
<212> TYPE: PRT
<213> ORGANISM: Chlorella virus PBCV-1

<400> SEQUENCE: 7

```
Met Gly Lys Asn Ile Ile Met Val Ser Trp Tyr Thr Ile Ile Thr
 1               5                  10                  15

Ser Asn Leu Ile Ala Val Gly Ala Ser Leu Ile Leu Ala Pro Ala
            20                  25                  30

Ile Thr Gly Tyr Val Leu His Trp Asn Ile Ala Leu Ser Thr Ile Trp
        35                  40                  45

Gly Val Ser Ala Tyr Gly Ile Phe Val Phe Gly Phe Phe Leu Ala Gln
     50                  55                  60

Val Leu Phe Ser Glu Leu Asn Arg Lys Arg Leu Arg Lys Trp Ile Ser
65                  70                  75                  80

Leu Arg Pro Lys Gly Trp Asn Asp Val Arg Leu Ala Val Ile Ile Ala
                85                  90                  95

Gly Tyr Arg Glu Asp Pro Tyr Met Phe Gln Lys Cys Leu Glu Ser Val
            100                 105                 110

Arg Asp Ser Asp Tyr Gly Asn Val Ala Arg Leu Ile Cys Val Ile Asp
        115                 120                 125

Gly Asp Glu Asp Asp Met Arg Met Ala Ala Val Tyr Lys Ala Ile
    130                 135                 140

Tyr Asn Asp Asn Ile Lys Lys Pro Glu Phe Val Leu Cys Glu Ser Asp
145                 150                 155                 160

Asp Lys Glu Gly Glu Arg Ile Asp Ser Asp Phe Ser Arg Asp Ile Cys
                165                 170                 175

Val Leu Gln Pro His Arg Gly Lys Arg Glu Cys Leu Tyr Thr Gly Phe
            180                 185                 190

Gln Leu Ala Lys Met Asp Pro Ser Val Asn Ala Val Leu Ile Asp
        195                 200                 205

Ser Asp Thr Val Leu Glu Lys Asp Ala Ile Leu Glu Val Val Tyr Pro
    210                 215                 220

Leu Ala Cys Asp Pro Glu Ile Gln Ala Val Ala Gly Glu Cys Lys Ile
225                 230                 235                 240

Trp Asn Thr Asp Thr Leu Leu Ser Leu Leu Val Ala Trp Arg Tyr Tyr
                245                 250                 255

Ser Ala Phe Cys Val Glu Arg Ser Ala Gln Ser Phe Phe Arg Thr Val
            260                 265                 270

Gln Cys Val Gly Gly Pro Leu Gly Ala Tyr Lys Asp Ile Ile Lys Glu
        275                 280                 285

Ile Lys Asp Pro Trp Ile Ser Gln Arg Phe Leu Gly Gln Lys Cys Thr
    290                 295                 300

Tyr Gly Asp Asp Arg Arg Leu Thr Asn Glu Ile Leu Met Arg Gly Lys
305                 310                 315                 320

Lys Val Val Phe Thr Pro Phe Ala Val Gly Trp Ser Asp Ser Pro Thr
                325                 330                 335

Asn Val Phe Arg Tyr Ile Val Gln Gln Thr Arg Trp Ser Lys Ser Trp
            340                 345                 350
```

-continued

```
Cys Arg Glu Ile Trp Tyr Thr Leu Phe Ala Ala Trp Lys His Gly Leu
        355                 360                 365
Ser Gly Ile Trp Leu Ala Phe Glu Cys Leu Tyr Gln Ile Thr Tyr Phe
    370                 375                 380
Phe Leu Val Ile Tyr Leu Phe Ser Arg Leu Ala Val Glu Ala Asp Pro
385                 390                 395                 400
Arg Ala Gln Thr Ala Thr Val Ile Val Ser Thr Thr Val Ala Leu Ile
                405                 410                 415
Lys Cys Gly Tyr Phe Ser Phe Arg Ala Lys Asp Ile Arg Ala Phe Tyr
            420                 425                 430
Phe Val Leu Tyr Thr Phe Val Tyr Phe Cys Met Ile Pro Ala Arg
        435                 440                 445
Ile Thr Ala Met Met Thr Leu Trp Asp Ile Gly Trp Asp Thr Arg Gly
    450                 455                 460
Gly Asn Glu Lys Pro Ser Val Gly Thr Arg Val Ala Leu Trp Ala Lys
465                 470                 475                 480
Gln Tyr Leu Ile Ala Tyr Met Trp Trp Ala Ala Val Val Gly Ala Gly
                485                 490                 495
Val Tyr Ser Ile Val His Asn Trp Met Phe Asp Trp Asn Ser Leu Ser
            500                 505                 510
Tyr Arg Phe Ala Leu Val Gly Ile Cys Ser Tyr Ile Val Phe Ile Val
        515                 520                 525
Ile Val Leu Val Val Tyr Phe Thr Gly Lys Ile Thr Thr Trp Asn Phe
    530                 535                 540
Thr Lys Leu Gln Lys Glu Leu Ile Glu Asp Arg Val Leu Tyr Asp Ala
545                 550                 555                 560
Thr Thr Asn Ala Gln Ser Val
                565
```

<210> SEQ ID NO 8
<211> LENGTH: 1740
<212> TYPE: DNA
<213> ORGANISM: Chlorella virus PBCV-1

<400> SEQUENCE: 8

```
aagacttctt gaaagttaca atgggtaaaa atataatcat aatggtttcg tggtacacca      60
tcataacttc aaatctaatc gcggttggag gagcctctct aatcttggct ccggcaatta     120
ctgggtatgt tctacattgg aatattgctc tctcgacaat ctggggagta tcagcttatg     180
gtattttcgt ttttgggttt ttccttgcac aagtttttatt ttcagaactg aacaggaaac     240
gtcttcgcaa gtggatttct ctcagaccta agggttggaa tgatgttcgt ttggctgtga     300
tcattgctgg atatcgcgag gatccttata tgttccagaa gtgcctcgag tctgtacgtg     360
actctgatta tggcaacgtt gcccgtctga tttgtgtgat tgacggtgat gaggacgatg     420
atatgaggat ggctgccgtt tacaaggcga tctacaatga taatatcaag aagcccgagt     480
ttgttctgtg tgagtcagac gacaaggaag gtgaacgcat cgactctgat ttctctcgcg     540
acatttgtgt cctccagcct catcgtggaa acgggagtg tctttatact gggtttcaac     600
ttgcaaagat ggaccccagt gtcaatgctg tcgttctgat tgacagcgat accgttctcg     660
agaaggatgc tattctggaa gttgtatacc cacttgcatg cgatcccgag atccaagccg     720
ttgcaggtga gtgtaagatt tggaacacag acactctttt gagtcttctc gtcgcttggc     780
ggtactattc tgcgttttgt gtggagagga gtgcccagtc ttttttcagg actgttcagt     840
gcgttggggg gccactgggt gcctacaaga ttgatatcat taaggagatt aaggacccct     900
```

-continued ggatttccca gcgctttctt ggtcagaagt gtacttacgg tgacgaccgc cggctaacca 960
acgagatctt gatgcgtggt aaaaaggttg tgttcactcc atttgctgtt ggttggtctg 1020
acagtccgac caatgtgttt cggtacatcg ttcagcagac ccgctggagt aagtcgtggt 1080
gccgcgaaat ttggtacacc ctcttcgccg cgtggaagca cggtttgtct ggaatttggc 1140
tggcctttga atgtttgtat caaattacat acttcttcct cgtgatttac ctcttttctc 1200
gcctagccgt tgaggccgac cctcgcgccc agacagccac ggtgattgtg agcaccacgg 1260
ttgcattgat taagtgtggg tatttttcat tccgagccaa ggatattcgg gcgttttact 1320
ttgtgcttta tacatttgtt tacttttctt gtatgattcc ggccaggatt actgcaatga 1380
tgacgctttg ggacattggc tgggatactc gcggtggaaa cgagaagcct tccgttggca 1440
cccgggtcgc tctgtgggca aagcaatatc tcattgcata tatgtggtgg gccgcggttg 1500
ttggcgctgg agtttacagc atcgtccata actggatgtt cgattggaat tctctttctt 1560
atcgttttgc tttggttggt atttgttctt acattgtttt tattgttatt gtgctggtgg 1620
tttatttcac cggcaaaatt acgacttgga atttcacgaa gcttcagaag gagctaatcg 1680
aggatcgcgt tctgtacgat gcaactacca atgctcagtc tgtgtgattt ttcctgcaag 1740

<210> SEQ ID NO 9
<211> LENGTH: 2937
<212> TYPE: DNA
<213> ORGANISM: pasteurella multocida

<400> SEQUENCE: 9 atttttaag gacagaaaat gaatacatta tcacaagcaa taaaagcata taacagcaat 60
gactatcaat tagcactcaa attatttgaa aagtcggcgg aaatctatgg acggaaaatt 120
gttgaatttc aaattaccaa atgccaagaa aaactctcag cacatccttc tgttaattca 180
gcacatcttt ctgtaaataa agaagaaaaa gtcaatgttt gcgatagtcc gttagatatt 240
gcaacacaac tgttactttc caacgtaaaa aaattagtac tttctgactc ggaaaaaaac 300
acgttaaaaa ataaatggaa attgctcact gagaagaaat ctgaaaatgc ggaggtaaga 360
gcggtcgccc ttgtaccaaa agattttccc aaagatctgg ttttagcgcc tttacctgat 420
catgttaatg attttacatg gtacaaaaag cgaaagaaaa gacttggcat aaaacctgaa 480
catcaacatg ttggtctttc tattatcgtt acaacattca atcgaccagc aattttatcg 540
attacattag cctgtttagt aaaccaaaaa acacattacc cgtttgaagt tatcgtgaca 600
gatgatggta gtcaggaaga tctatcaccg atcattcgcc aatatgaaaa taaattggat 660
attcgctacg tcagacaaaa agataacggt tttcaagcca gtgccgctcg gaatatggga 720
ttacgcttag caaaatatga ctttattggc ttactcgact gtgatatggc gccaaatcca 780
ttatgggttc attcttatgt tgcagagcta ttagaagatg atgatttaac aatcattggt 840
ccaagaaaat acatcgatac acaacatatt gacccaaaag acttcttaaa taacgcgagt 900
ttgcttgaat cattaccaga agtgaaaacc aataatagtg ttgccgcaaa aggggaagga 960
acagtttctc tggattggcg cttagaacaa ttcgaaaaaa cagaaaatct ccgcttatcc 1020
gattcgcctt tccgtttttt tgcggcgggt aatgttgctt tcgctaaaaa atggctaaat 1080
aaatccggtt tctttgatga ggaatttaat cactggggtg gagaagatgt ggaatttgga 1140
tatcgcttat tccgttacgg tagtttcttt aaaactattg atggcattat ggcctaccat 1200
caagagccac caggtaaaga aaatgaaacc gatcgtgaag cgggaaaaaa tattacgctc 1260

-continued

```
gatattatga gagaaaaggt cccttatatc tatagaaaac ttttaccaat agaagattcg   1320
catatcaata gagtaccttt agtttcaatt tatatcccag cttataactg tgcaaactat   1380
attcaacgtt gcgtagatag tgcactgaat cagactgttg ttgatctcga ggtttgtatt   1440
tgtaacgatg gttcaacaga taatacctta gaagtgatca ataagcttta tggtaataat   1500
cctagggtac gcatcatgtc taaaccaaat ggcggaatag cctcagcatc aaatgcagcc   1560
gtttcttttg ctaaaggtta ttacattggg cagttagatt cagatgatta tcttgagcct   1620
gatgcagttg aactgtgttt aaaagaattt ttaaaagata aacgctagc ttgtgtttat    1680 accactaata gaaacgtcaa tccggatggt agcttaatcg ctaatggtta caattggcca   1740
gaattttcac gagaaaaact cacaacggct atgattgctc accactttag aatgttcacg   1800
attagagctt ggcatttaac tgatggattc aatgaaaaaa ttgaaaatgc cgtagactat   1860
gacatgttcc tcaaactcag tgaagttgga aaatttaaac atcttaataa aatctgctat   1920
aaccgtgtat tacatggtga taacacatca attaagaaac ttggcattca aaagaaaaac   1980
cattttgttg tagtcaatca gtcattaaat agacaaggca taacttatta taattatgac   2040
gaatttgatg atttagatga aagtagaaag tatattttca ataaaaccgc tgaatatcaa   2100
gaagagattg atatcttaaa agatattaaa atcatccaga ataaagatgc caaaatcgca   2160
gtcagtattt tttatcccaa tacattaaac ggcttagtga aaaaactaaa caatattatt   2220
gaatataata aaaatatatt cgttattgtt ctacatgttg ataagaatca tcttacacca   2280
gatatcaaaa aagaaatact agccttctat cataaacatc aagtgaatat tttactaaat   2340
aatgatatct catattacac gagtaataga ttaataaaaa ctgaggcgca tttaagtaat   2400
attaataaat taagtcagtt aaatctaaat tgtgaataca tcatttttga taatcatgac   2460
agcctattcg ttaaaaatga cagctatgct tatatgaaaa aatatgatgt cggcatgaat   2520
ttctcagcat taacacatga ttggatcgag aaaatcaatg cgcatccacc atttaaaaag   2580
ctcattaaaa cttattttaa tgacaatgac ttaaaaagta tgaatgtgaa aggggcatca   2640
caaggtatgt ttatgacgta tgcgctagcg catgagcttc tgacgattat taaagaagtc   2700
atcacatctt gccagtcaat tgatagtgtg ccagaatata acactgagga tatttggttc   2760
caatttgcac ttttaatctt agaaaagaaa accggccatg tatttaataa aacatcgacc   2820
ctgacttata tgccttggga acgaaaatta caatggacaa atgaacaaat tgaaagtgca   2880
aaaagaggag aaaatatacc tgttaacaag ttcattatta atagtataac tctataa      2937
```

<210> SEQ ID NO 10
<211> LENGTH: 972
<212> TYPE: PRT
<213> ORGANISM: pasteurella multocida

<400> SEQUENCE: 10

```
Met Asn Thr Leu Ser Gln Ala Ile Lys Ala Tyr Asn Ser Asn Asp Tyr
1               5                   10                  15

Gln Leu Ala Leu Lys Leu Phe Glu Lys Ser Ala Glu Ile Tyr Gly Arg
            20                  25                  30

Lys Ile Val Glu Phe Gln Ile Thr Lys Cys Gln Glu Lys Leu Ser Ala
        35                  40                  45

His Pro Ser Val Asn Ser Ala His Leu Ser Val Asn Lys Glu Glu Lys
    50                  55                  60

Val Asn Val Cys Asp Ser Pro Leu Asp Ile Ala Thr Gln Leu Leu Leu
65                  70                  75                  80
```

-continued

```
Ser Asn Val Lys Lys Leu Val Leu Ser Asp Ser Glu Lys Asn Thr Leu
             85                  90                  95

Lys Asn Lys Trp Lys Leu Leu Thr Glu Lys Lys Ser Glu Asn Ala Glu
            100                 105                 110

Val Arg Ala Val Ala Leu Val Pro Lys Asp Phe Pro Lys Asp Leu Val
            115                 120                 125

Leu Ala Pro Leu Pro Asp His Val Asn Asp Phe Thr Trp Tyr Lys Lys
        130                 135                 140

Arg Lys Lys Arg Leu Gly Ile Lys Pro Glu His Gln His Val Gly Leu
145                 150                 155                 160

Ser Ile Ile Val Thr Thr Phe Asn Arg Pro Ala Ile Leu Ser Ile Thr
                165                 170                 175

Leu Ala Cys Leu Val Asn Gln Lys Thr His Tyr Pro Phe Glu Val Ile
            180                 185                 190

Val Thr Asp Asp Gly Ser Gln Glu Asp Leu Ser Pro Ile Ile Arg Gln
        195                 200                 205

Tyr Glu Asn Lys Leu Asp Ile Arg Tyr Val Arg Gln Lys Asp Asn Gly
    210                 215                 220

Phe Gln Ala Ser Ala Ala Arg Asn Met Gly Leu Arg Leu Ala Lys Tyr
225                 230                 235                 240

Asp Phe Ile Gly Leu Leu Asp Cys Asp Met Ala Pro Asn Pro Leu Trp
                245                 250                 255

Val His Ser Tyr Val Ala Glu Leu Leu Glu Asp Asp Asp Leu Thr Ile
            260                 265                 270

Ile Gly Pro Arg Lys Tyr Ile Asp Thr Gln His Ile Asp Pro Lys Asp
        275                 280                 285

Phe Leu Asn Asn Ala Ser Leu Leu Glu Ser Leu Pro Glu Val Lys Thr
    290                 295                 300

Asn Asn Ser Val Ala Ala Lys Gly Glu Gly Thr Val Ser Leu Asp Trp
305                 310                 315                 320

Arg Leu Glu Gln Phe Glu Lys Thr Glu Asn Leu Arg Leu Ser Asp Ser
                325                 330                 335

Pro Phe Arg Phe Phe Ala Ala Gly Asn Val Ala Phe Ala Lys Lys Trp
            340                 345                 350

Leu Asn Lys Ser Gly Phe Phe Asp Glu Glu Phe Asn His Trp Gly Gly
        355                 360                 365

Glu Asp Val Glu Phe Gly Tyr Arg Leu Phe Arg Tyr Gly Ser Phe Phe
    370                 375                 380

Lys Thr Ile Asp Gly Ile Met Ala Tyr His Gln Glu Pro Pro Gly Lys
385                 390                 395                 400

Glu Asn Glu Thr Asp Arg Glu Ala Gly Lys Asn Ile Thr Leu Asp Ile
                405                 410                 415

Met Arg Glu Lys Val Pro Tyr Ile Tyr Arg Lys Leu Leu Pro Ile Glu
            420                 425                 430

Asp Ser His Ile Asn Arg Val Pro Leu Val Ser Ile Tyr Ile Pro Ala
        435                 440                 445

Tyr Asn Cys Ala Asn Tyr Ile Gln Arg Cys Val Asp Ser Ala Leu Asn
    450                 455                 460

Gln Thr Val Val Asp Leu Glu Val Cys Ile Cys Asn Asp Gly Ser Thr
465                 470                 475                 480

Asp Asn Thr Leu Glu Val Ile Asn Lys Leu Tyr Gly Asn Asn Pro Arg
                485                 490                 495

Val Arg Ile Met Ser Lys Pro Asn Gly Gly Ile Ala Ser Ala Ser Asn
```

-continued

```
                500                 505                 510
Ala Ala Val Ser Phe Ala Lys Gly Tyr Tyr Ile Gly Gln Leu Asp Ser
            515                 520                 525

Asp Asp Tyr Leu Glu Pro Asp Ala Val Glu Leu Cys Leu Lys Glu Phe
            530                 535                 540

Leu Lys Asp Lys Thr Leu Ala Cys Val Tyr Thr Thr Asn Arg Asn Val
545                 550                 555                 560

Asn Pro Asp Gly Ser Leu Ile Ala Asn Gly Tyr Asn Trp Pro Glu Phe
            565                 570                 575

Ser Arg Glu Lys Leu Thr Thr Ala Met Ile Ala His His Phe Arg Met
            580                 585                 590

Phe Thr Ile Arg Ala Trp His Leu Thr Asp Gly Phe Asn Glu Lys Ile
            595                 600                 605

Glu Asn Ala Val Asp Tyr Asp Met Phe Leu Lys Leu Ser Glu Val Gly
            610                 615                 620

Lys Phe Lys His Leu Asn Lys Ile Cys Tyr Asn Arg Val Leu His Gly
625                 630                 635                 640

Asp Asn Thr Ser Ile Lys Lys Leu Gly Ile Gln Lys Lys Asn His Phe
            645                 650                 655

Val Val Val Asn Gln Ser Leu Asn Arg Gln Gly Ile Thr Tyr Tyr Asn
            660                 665                 670

Tyr Asp Glu Phe Asp Asp Leu Asp Glu Ser Arg Lys Tyr Ile Phe Asn
            675                 680                 685

Lys Thr Ala Glu Tyr Gln Glu Glu Ile Asp Ile Leu Lys Asp Ile Lys
            690                 695                 700

Ile Ile Gln Asn Lys Asp Ala Lys Ile Ala Val Ser Ile Phe Tyr Pro
705                 710                 715                 720

Asn Thr Leu Asn Gly Leu Val Lys Lys Leu Asn Asn Ile Ile Glu Tyr
            725                 730                 735

Asn Lys Asn Ile Phe Val Ile Val Leu His Val Asp Lys Asn His Leu
            740                 745                 750

Thr Pro Asp Ile Lys Lys Glu Ile Leu Ala Phe Tyr His Lys His Gln
            755                 760                 765

Val Asn Ile Leu Leu Asn Asn Asp Ile Ser Tyr Tyr Thr Ser Asn Arg
770                 775                 780

Leu Ile Lys Thr Glu Ala His Leu Ser Asn Ile Asn Lys Leu Ser Gln
785                 790                 795                 800

Leu Asn Leu Asn Cys Glu Tyr Ile Ile Phe Asp Asn His Asp Ser Leu
            805                 810                 815

Phe Val Lys Asn Asp Ser Tyr Ala Tyr Met Lys Lys Tyr Asp Val Gly
            820                 825                 830

Met Asn Phe Ser Ala Leu Thr His Asp Trp Ile Glu Lys Ile Asn Ala
            835                 840                 845

His Pro Pro Phe Lys Lys Leu Ile Lys Thr Tyr Phe Asn Asp Asn Asp
            850                 855                 860

Leu Lys Ser Met Asn Val Lys Gly Ala Ser Gln Gly Met Phe Met Thr
865                 870                 875                 880

Tyr Ala Leu Ala His Glu Leu Leu Thr Ile Ile Lys Glu Val Ile Thr
            885                 890                 895

Ser Cys Gln Ser Ile Asp Ser Val Pro Glu Tyr Asn Thr Glu Asp Ile
            900                 905                 910

Trp Phe Gln Phe Ala Leu Leu Ile Leu Glu Lys Lys Thr Gly His Val
            915                 920                 925
```

```
Phe Asn Lys Thr Ser Thr Leu Thr Tyr Met Pro Trp Glu Arg Lys Leu
    930                 935                 940

Gln Trp Thr Asn Glu Gln Ile Glu Ser Ala Lys Arg Gly Glu Asn Ile
945                 950                 955                 960

Pro Val Asn Lys Phe Ile Ile Asn Ser Ile Thr Leu
                965                 970

<210> SEQ ID NO 11
<211> LENGTH: 3466
<212> TYPE: DNA
<213> ORGANISM: Streptococcus uberis

<400> SEQUENCE: 11
gcaaaagttt aaaggaggaa ttatggaaaa actaaaaaat ctcattacat ttatgacttt      60
tattttcctg tggctcataa ttattgggct taatgttttt gtatttggaa ctaaaggaag     120
tctaacagtg tatgggatta ttctattaac ctatttgtcg ataaaaatgg gattatcttt     180
tttttatcgt ccctataaag gaagtgtagg tcaatataag gtagcagcta ttatcccatc     240
ttataatgag gatggtgtcg gtttactaga aactctaaag agtgttcaaa acaaacata     300 tccaattgca gaaattttcg taattgacga tgggtcagta gataaaacag gtataaaatt     360
ggtcgaagac tatgtgaagt taaatggctt ggagaccaa gttatcgttc atcagatgcc     420
tgaaaatgtt ggtaaaagac atgctcaggc ttgggcattt gaaaggtctg atgctgatgt     480
tttcttaaca gtggattcag atacctacat ctatcctgat gctcttgaag aattattaaa     540
gacatttaat gatccagagg tctacgctgc aactggtcat ttaaatgcaa gaaatagaca     600
aactaatctc ttaactagac tgactgatat tcgttacgat aatgcatttg gtgtagaacg     660
tgctgctcag tctgttacgg gaaatatttt ggtttgttcc ggacctttaa gtatttatag     720
acgttccgtc ggtattccaa atcttgaacg ctatacctca caaacatttc ttggtgtccc     780
tgtaagcata ggggatgacc gttgtttgac aaattatgca actgatttgg gaaaaacggt     840
ttatcagtca actgcaagat gtgatactga cgttccagat aagtttaagg ttttcatcaa     900
acaacaaaat cgttggaata agtcattttt tagggagtct attatctctg ttaagaagtt     960
attagccaca ccaagtgttg ctgtttggac tattacagaa gtttccatgt tcatcatgct    1020
agtttattct atctttagct tattgatagg agaggctcaa gaatttaatc tcataaaact    1080
ggttgctttt ttagttatta ttttcatagt agctctttgt agaaatgttc attacatggt    1140
taagcatcca tttgcttttt tattgtcacc gttttatgga ttgatacatc tattcgtttt    1200
gcaacctctt aagatatatt cgttatttac tataagaaat gctacatggg gaactcgtaa    1260
aaagacaagt aaataattca attagagaaa ggacaaaata gtgaaaattg cagttgcagg    1320
ttctggctat gttggcctat cattaagtgt attattagca cagaaaaatc ctgttacagt    1380
tgtagatatt attgagaaga agtaaatct cataaatcaa aaacaatcac caatccagga    1440
tgttgatatt gaaaactatt taaagaaaa aagttacaa ttaagagcta ctctagacgc    1500
cgatcaagca tttagggatg cagatatact aattattgct acaccaacca attatgatgt    1560
ggagaagaat ttttttgata ctagtcatgt tgagactgta attgagaaag ctttagcttt    1620
aaatagtcag gctttgttag ttattaaatc aacgatacca cttggtttta ttaaaaagat    1680
gcgtcaaaaa tatcagacag accgtattat ttttagtccc gaatttctta gagagtctaa    1740
agctttaaaa gataatcttt atcctagtcg aataattgtt tcctttgaag atgatgattc    1800
tatggaagta atagaagcag caaagacttt tgctcaattg ttaaaagatg gttctttgga    1860
```

```
taaagatgtt cctgtacttt ttatgggttc agcagaggct gaagcagtaa aattatttgc    1920
caatacctat ttagctatgc gtgtctccta ttttaatgag ttagatacat atgctgaaaa    1980
gaatggttta cgtgtggata atattattga gggcgtttgc catgatcgac gcataggaat    2040
tcattataat aacccttctt ttggctatgg aggatactgc ttacctaaag ataccaaaca    2100
gttgctagca ggctatgatg gtattcctca atcgcttata aaagcaattg ttgattctaa    2160
taaaattcgt aaagagtata tcgcatcaca aattttacaa caattgagtg atattaatgt    2220
agatcctaaa gatgcaacga ttggtattta ccgccttatc atgaaaagta actctgataa    2280
tttcagagag agtgcaataa aagatattat tgatcatatt aagagctatc aaattaatat    2340
agtcttgtat gagccaatga tgaatgaaga ttttgattta ccaatcattg atgatttatc    2400
tgacttcaaa gccatgtcac atattatcgt ttcaaataga tatgatttag ccttagaaga    2460
tgttaaagaa aaagtttaca ccagagatat ttacggtgtg gattaagttt gattttaac    2520 aaatctccaa aaatagata aaaaaaacag actctgataa aagagtctgt ttttaaaag    2580 tgtgagcatc ctattgctag gatgctcagg aaatttatga aaaggagat aagagggaac    2640 ttatcttccc caacggtttg ggagaccatt atttaggata gtcttatcat aagctatcaa    2700
ccttaaagat ttcttaactc gttttcgttt gggtcttgtc tttttaattt tttgatgaga    2760
attaaacttg atggaatgag aatcaggaca ctgcctatcc aggctgctgg attagctgaa    2820
gccacaccaa caaaaccaaa gtataacagg ccaataatgg cgactcctgc tctcatgact    2880
aattccataa tgccagctaa agtaggaaca aaaccgtatc cgagaccttg aatgaaactt    2940
cttagtataa ataggatggc taaaatccaa taaagagagc cattaatcag ataatagaa    3000 taggctaaat ggaaaacagc tggatcagcc ttactaatga aaatgccaga gaaaagcgg    3060 tgttggaaaa ttaacagaat agcaaaaaga acagaccaaa taatacagat aatgagtgaa    3120
tctttaagac cctcaaggat tcttttataa gctttagcgc catagttctg agctgtaaag    3180
gttgacaagg ctaagcccag atttaacatc ggtagcatgg ccagttggtc tgttttactg    3240
gcaatagcaa tagctgcgat agcttcggtc cccaacttat taatggttac ctgcagtgta    3300
atggctccaa tggctataat actagcctga atgccatgg gaaaaccaag gcgagcatga    3360
tttctgagat tttccctatc aagagtcaaa tcgtctttct tcagtcggaa atggggatc    3420 tttttgttga tgtaaaggac caaatagagt acggagaaag cttgca              3466
```

<210> SEQ ID NO 12
<211> LENGTH: 417
<212> TYPE: PRT
<213> ORGANISM: Streptococcus uberis

<400> SEQUENCE: 12

```
Met Glu Lys Leu Lys Asn Leu Ile Thr Phe Met Thr Phe Ile Phe Leu
1               5                   10                  15

Trp Leu Ile Ile Ile Gly Leu Asn Val Phe Val Phe Gly Thr Lys Gly
                20                  25                  30

Ser Leu Thr Val Tyr Gly Ile Ile Leu Leu Thr Tyr Leu Ser Ile Lys
            35                  40                  45

Met Gly Leu Ser Phe Phe Tyr Arg Pro Tyr Lys Gly Ser Val Gly Gln
        50                  55                  60

Tyr Lys Val Ala Ala Ile Ile Pro Ser Tyr Asn Glu Asp Gly Val Gly
65                  70                  75                  80

Leu Leu Glu Thr Leu Lys Ser Val Gln Lys Gln Thr Tyr Pro Ile Ala
```

```
                        85                  90                  95
Glu Ile Phe Val Ile Asp Asp Gly Ser Val Asp Lys Thr Gly Ile Lys
                100                 105                 110
Leu Val Glu Asp Tyr Val Lys Leu Asn Gly Phe Gly Asp Gln Val Ile
            115                 120                 125
Val His Gln Met Pro Glu Asn Val Gly Lys Arg His Ala Gln Ala Trp
        130                 135                 140
Ala Phe Glu Arg Ser Asp Ala Asp Val Phe Leu Thr Val Asp Ser Asp
145                 150                 155                 160
Thr Tyr Ile Tyr Pro Asp Ala Leu Glu Glu Leu Leu Lys Thr Phe Asn
                165                 170                 175
Asp Pro Glu Val Tyr Ala Ala Thr Gly His Leu Asn Ala Arg Asn Arg
            180                 185                 190
Gln Thr Asn Leu Leu Thr Arg Leu Thr Asp Ile Arg Tyr Asp Asn Ala
        195                 200                 205
Phe Gly Val Glu Arg Ala Ala Gln Ser Val Thr Gly Asn Ile Leu Val
210                 215                 220
Cys Ser Gly Pro Leu Ser Ile Tyr Arg Arg Ser Val Gly Ile Pro Asn
225                 230                 235                 240
Leu Glu Arg Tyr Thr Ser Gln Thr Phe Leu Gly Val Pro Val Ser Ile
                245                 250                 255
Gly Asp Asp Arg Cys Leu Thr Asn Tyr Ala Thr Asp Leu Gly Lys Thr
            260                 265                 270
Val Tyr Gln Ser Thr Ala Arg Cys Asp Thr Asp Val Pro Asp Lys Phe
        275                 280                 285
Lys Val Phe Ile Lys Gln Gln Asn Arg Trp Asn Lys Ser Phe Phe Arg
290                 295                 300
Glu Ser Ile Ile Ser Val Lys Lys Leu Leu Ala Thr Pro Ser Val Ala
305                 310                 315                 320
Val Trp Thr Ile Thr Glu Val Ser Met Phe Ile Met Leu Val Tyr Ser
                325                 330                 335
Ile Phe Ser Leu Leu Ile Gly Glu Ala Gln Glu Phe Asn Leu Ile Lys
            340                 345                 350
Leu Val Ala Phe Leu Val Ile Ile Phe Ile Val Ala Leu Cys Arg Asn
        355                 360                 365
Val His Tyr Met Val Lys His Pro Phe Ala Phe Leu Leu Ser Pro Phe
370                 375                 380
Tyr Gly Leu Ile His Leu Phe Val Leu Gln Pro Leu Lys Ile Tyr Ser
385                 390                 395                 400
Leu Phe Thr Ile Arg Asn Ala Thr Trp Gly Thr Arg Lys Lys Thr Ser
                405                 410                 415
Lys
```

<210> SEQ ID NO 13
<211> LENGTH: 1440
<212> TYPE: DNA
<213> ORGANISM: Streptococcus pyogenes

<400> SEQUENCE: 13

```
tttaatggaa acacaatttt attaaaaata tctctatatc tagttgacat tatttcttat      60
ttatattata atattgaggt cctttctttc aaggaaatta aaaagaaag aggtgtaatt     120
gtgcctattt ttaaaaaaac tttaattgtt ttatcctttta ttttttttgat atctatcttg   180
atttatctaa atatgtatct atttggaaca tcaactgtag gaatttatgg agtaatatta    240
```

-continued

```
ataacctatc tagttatcaa acttggatta tctttcctttt atgagccatt taaaggaaat      300
ccacatgact ataaagttgc tgctgtaatt ccttcttata atgaagatgc cgagtcatta      360
ttagaaacac ttaaaagtgt gttagcacag acctatccgt tatcagaaat ttatattgtt      420
gatgatggga gttcaaacac agatgcaata caattaattg aagagtatgt aaatagagaa      480
gtggatattt gtcgaaacgt tatcgttcac cgttcccttg tcaataaagg aaaacgccat      540
gctcaagcgt gggcatttga agatctgac gctgacgttt ttttaaccgt agactcagat      600
acttatatct atccaaatgc cttagaagaa ctcctaaaaa gcttcaatga tgagacagtt      660
tatgctgcaa caggacattt gaatgctaga acagacaaa ctaatctatt aacgcgactt      720
acagatatcc gttacgataa tgcctttggg gtggagcgtg ctgctcaatc attaacaggt      780
aatatttttag tttgctcagg accattgagt atttatcgac gtgaagtgat tattcctaac      840
ttagagcgct ataaaaatca aacattccta ggtttacctg ttagcattgg ggatgatcga      900
tgtttaacaa attatgctat tgatttagga cgcactgtct accaatcaac agctagatgt      960
gatactgatg tacctttcca attaaaaagt tatttaaagc aacaaaatcg atggaataaa     1020
tcttttttta gagaatctat tatttctgtt aaaaaaattc tttctaatcc catcgttgcc     1080
ttatggacta ttttcgaagt cgttatgttt atgatgttga ttgtcgcaat tgggaatctt     1140
ttgtttaatc aagctattca attagacctt attaaacttt ttgcctttt atccatcatc     1200
tttatcgttg ctttatgtcg taatgttcat tatatggtca aacatcctgc tagttttttg     1260
ttatctcctc tgtatggaat attacacttg tttgtcttac agcccctaaa actttattct     1320
ttatgcacca ttaaaaatac ggaatgggga acacgtaaaa aggtcactat ttttaaataa     1380
tatatgcatc gagtagttag agaaggagta attttatgaa aatagcagtt gctggatcag     1440
```

<210> SEQ ID NO 14
<211> LENGTH: 419
<212> TYPE: PRT
<213> ORGANISM: Streptococcus pyogenes

<400> SEQUENCE: 14

```
Met Pro Ile Phe Lys Lys Thr Leu Ile Val Leu Ser Phe Ile Phe Leu
1               5                   10                  15

Ile Ser Ile Leu Ile Tyr Leu Asn Met Tyr Leu Phe Gly Thr Ser Thr
            20                  25                  30

Val Gly Ile Tyr Gly Val Ile Leu Ile Thr Tyr Leu Val Ile Lys Leu
        35                  40                  45

Gly Leu Ser Phe Leu Tyr Glu Pro Phe Lys Gly Asn Pro His Asp Tyr
    50                  55                  60

Lys Val Ala Ala Val Ile Pro Ser Tyr Asn Glu Asp Ala Glu Ser Leu
65                  70                  75                  80

Leu Glu Thr Leu Lys Ser Val Leu Ala Gln Thr Tyr Pro Leu Ser Glu
                85                  90                  95

Ile Tyr Ile Val Asp Asp Gly Ser Ser Asn Thr Asp Ala Ile Gln Leu
            100                 105                 110

Ile Glu Glu Tyr Val Asn Arg Glu Val Asp Ile Cys Arg Asn Val Ile
        115                 120                 125

Val His Arg Ser Leu Val Asn Lys Gly Lys Arg His Ala Gln Ala Trp
    130                 135                 140

Ala Phe Glu Arg Ser Asp Ala Asp Val Phe Leu Thr Val Asp Ser Asp
145                 150                 155                 160
```

-continued

```
Thr Tyr Ile Tyr Pro Asn Ala Leu Glu Glu Leu Leu Lys Ser Phe Asn
            165                 170                 175

Asp Glu Thr Val Tyr Ala Ala Thr Gly His Leu Asn Ala Arg Asn Arg
        180                 185                 190

Gln Thr Asn Leu Leu Thr Arg Leu Thr Asp Ile Arg Tyr Asp Asn Ala
    195                 200                 205

Phe Gly Val Glu Arg Ala Ala Gln Ser Leu Thr Gly Asn Ile Leu Val
210                 215                 220

Cys Ser Gly Pro Leu Ser Ile Tyr Arg Arg Glu Val Ile Ile Pro Asn
225                 230                 235                 240

Leu Glu Arg Tyr Lys Asn Gln Thr Phe Leu Gly Leu Pro Val Ser Ile
                245                 250                 255

Gly Asp Asp Arg Cys Leu Thr Asn Tyr Ala Ile Asp Leu Gly Arg Thr
            260                 265                 270

Val Tyr Gln Ser Thr Ala Arg Cys Asp Thr Asp Val Pro Phe Gln Leu
        275                 280                 285

Lys Ser Tyr Leu Lys Gln Gln Asn Arg Trp Asn Lys Ser Phe Phe Arg
    290                 295                 300

Glu Ser Ile Ile Ser Val Lys Lys Ile Leu Ser Asn Pro Ile Val Ala
305                 310                 315                 320

Leu Trp Thr Ile Phe Glu Val Val Met Phe Met Met Leu Ile Val Ala
                325                 330                 335

Ile Gly Asn Leu Leu Phe Asn Gln Ala Ile Gln Leu Asp Leu Ile Lys
            340                 345                 350

Leu Phe Ala Phe Leu Ser Ile Ile Phe Ile Val Ala Leu Cys Arg Asn
        355                 360                 365

Val His Tyr Met Val Lys His Pro Ala Ser Phe Leu Leu Ser Pro Leu
    370                 375                 380

Tyr Gly Ile Leu His Leu Phe Val Leu Gln Pro Leu Lys Leu Tyr Ser
385                 390                 395                 400

Leu Cys Thr Ile Lys Asn Thr Glu Trp Gly Thr Arg Lys Lys Val Thr
                405                 410                 415

Ile Phe Lys

<210> SEQ ID NO 15
<211> LENGTH: 1380
<212> TYPE: DNA
<213> ORGANISM: Sulfolobus solfataricus

<400> SEQUENCE: 15
tgccctcatg cggttaagct tgaaatggcc ttttttagaa agagaaagga gttatctagt      60
taaccaatct tgccaccaga aagttatcat agcatatagg gaagcaatat attgcactgc     120
tagtgcgata gaaccgtata ttagagtttt caatttatct tctggaatta aataaatcat     180
ggtcattaca aagggtatta tagctataaa tcctccgtaa tgcaagaata ataaaagat      240 aaagaagtcg gaatggtaac gggttggcag atacaatagt aataagagct tagtattaat     300
tacattaatt gaggaataga tcttaagaat tctagtgaaa ctcatataaa ggaacaagag     360
cgtaaataat ggtaacagat tggtgtatat catattaaaa acgtataatg aaccccttt      420 acttatacta ccgtcagcta tctcccttat aaaattaaga taatttgctc ttgtccatct     480
agttacttgt ttcgtaaaca ttttttatgtc tctaggggt tttgtatatg ccactgcatc      540
aaagactttt acagccctat accctttttt tataacaaaa tcggttaaat ctctatcatc     600
ggaaatttta attggtcttc caaacatttt cggctctaaa aactctttag ataatatata     660
```

-continued

```
tggttttacg agttcggtcc tatatattac acattgtcca cttaatatta tagcacttcc    720
aaaatagttt accgccctgt ttactatctc acttattctc tcaaagaatt caccataata    780
atatgcatat ttattttct cgtcatacat aattctaata tttggcccta ctccacctac     840
tgactcatca aaaacactta acatctttag tatagagtct ttataaataa tcgtatcact    900
atctagaaac atcactagag gagatcttac atacttaact ccctcggcta acgcgtatct    960
tttcccctta tgttcacgca tataaataaa tttaccacca tatctttccg taattgattt   1020
gtatggttct agaacactat cccctacaac aataaattct aaccttgtgt catataaagt   1080
ccttatcact ttttcaaaaa tatctatttc tccttataa actggtatca caactgtaag    1140
atcagagaga ttataaaaac ttgagtgttg agttttcta ttattactta ttactgcaaa    1200
aaatgaattc aaaagaaat aagaatagt tataattgtg aatgaaagag aataaatgaa     1260
atatgagact ccgtgaaata agtgaaacat aatcaccact ataatgctcg atatcgaaat   1320
atataacgat ttttcctaat tcaccattcg aattctccgt tcaaaaaggg gttagttaac   1380
```

<210> SEQ ID NO 16
<211> LENGTH: 415
<212> TYPE: PRT
<213> ORGANISM: Sulfolobus solfataricus

<400> SEQUENCE: 16

```
Met Val Ile Met Phe His Leu Phe His Gly Val Ser Tyr Phe Ile Tyr
1               5                   10                  15

Ser Leu Ser Phe Thr Ile Ile Thr Ile Leu Tyr Phe Phe Leu Asn Ser
                20                  25                  30

Phe Phe Ala Val Ile Ser Asn Asn Arg Lys Thr Gln His Ser Ser Phe
            35                  40                  45

Tyr Asn Leu Ser Asp Leu Thr Val Val Ile Pro Val Tyr Lys Glu Glu
        50                  55                  60

Ile Asp Ile Phe Glu Lys Val Ile Arg Thr Leu Tyr Asp Thr Arg Leu
65                  70                  75                  80

Glu Phe Ile Val Val Gly Asp Ser Val Leu Glu Pro Tyr Lys Ser Ile
                85                  90                  95

Thr Glu Arg Tyr Gly Gly Lys Phe Ile Tyr Met Arg Glu His Lys Gly
                100                 105                 110

Lys Arg Tyr Ala Leu Ala Glu Gly Val Lys Tyr Val Arg Ser Pro Leu
            115                 120                 125

Val Met Phe Leu Asp Ser Asp Thr Ile Ile Tyr Lys Asp Ser Ile Leu
        130                 135                 140

Lys Met Leu Ser Val Phe Asp Glu Ser Val Gly Gly Val Gly Pro Asn
145                 150                 155                 160

Ile Arg Ile Met Tyr Asp Glu Lys Asn Lys Tyr Ala Tyr Tyr Gly
                165                 170                 175

Glu Phe Phe Glu Arg Ile Ser Glu Ile Val Asn Arg Ala Val Asn Tyr
            180                 185                 190

Phe Gly Ser Ala Ile Ile Leu Ser Gly Gln Cys Val Ile Tyr Arg Thr
        195                 200                 205

Glu Leu Val Lys Pro Tyr Ile Leu Ser Lys Glu Phe Leu Glu Pro Lys
    210                 215                 220

Met Phe Gly Arg Pro Ile Lys Ile Ser Asp Asp Arg Asp Leu Thr Asp
225                 230                 235                 240

Phe Val Ile Lys Lys Gly Tyr Arg Ala Val Lys Val Phe Asp Ala Val
```

```
                245                 250                 255
Ala Tyr Thr Lys Pro Pro Arg Asp Ile Lys Met Phe Thr Lys Gln Val
                    260                 265                 270

Thr Arg Trp Thr Arg Ala Asn Tyr Leu Asn Phe Ile Arg Glu Ile Ala
            275                 280                 285

Asp Gly Ser Ile Ser Lys Arg Gly Ser Leu Tyr Val Phe Asn Met Ile
        290                 295                 300

Tyr Thr Asn Leu Leu Pro Leu Phe Thr Leu Leu Phe Leu Tyr Met Ser
305                 310                 315                 320

Phe Thr Arg Ile Leu Lys Ile Tyr Ser Ser Ile Asn Val Ile Asn Thr
                325                 330                 335

Lys Leu Leu Leu Leu Tyr Leu Pro Thr Arg Tyr His Ser Asp Phe
                    340                 345                 350

Phe Ile Phe Tyr Leu Phe Leu His Tyr Gly Gly Phe Ile Ala Ile Ile
            355                 360                 365

Pro Phe Val Met Thr Met Ile Tyr Leu Ile Pro Glu Asp Lys Leu Lys
        370                 375                 380

Thr Leu Ile Tyr Gly Ser Ile Ala Leu Ala Val Gln Tyr Ile Ala Ser
385                 390                 395                 400

Leu Tyr Ala Met Ile Thr Phe Trp Trp Gln Asp Trp Leu Thr Arg
                405                 410                 415

<210> SEQ ID NO 17
<211> LENGTH: 1200
<212> TYPE: DNA
<213> ORGANISM: Bacillus anthracis pXO1

<400> SEQUENCE: 17
taaggttcca aatatgaaag tggcagtagt ggtcccctca tataatgaaa gtgcaagtgc      60
tattgttaat acaattaata gcgttttagc tcaagattat ccaattcatg aaatttcctt     120
tgttgatgat ggtagtaagg ataaatcggc ttatgaagta gcacttaaaa tgagggagga     180
acttcttaga actcaacgag aaattgctgc tacaactaag aatatttgtt ctgaaatatt     240
aggtattcct gacttaatcg tacatcgttt acctaagaat gcgggaaaa gacatgctca     300 attatgggct tttaaacgga caacagcaga tgctattgtt accattgatt cagatggtga     360
tttgttccca aatgctgtta gagagttatt gaaaccctt aatgatgaaa agtaatggc      420 cacaactggt cacgtgaaca ttcgtaatag aaatgataat ttattaacaa actaattga     480 tatgcgttat gacaatgcgt tccgtgtgga gcgtgcagca cagtccgtaa caggaaatgt     540
tcttgtttgt agtgggccgt taagttgtta tcgtagagaa gtaataactg aaaatttaga     600
acattatgga agtcagatgt tccttggtga ggaggtgcag tttggagatg atagatgtct     660
aactaattat gctatttga aagggaaaac agtttatcaa tccactgctc gatgtattac     720
tgatgctcca actacattaa acaatttct taaacagcaa ctacgttgga caagtcatt     780 ttttagagaa agtttaattt cacttggcat tggtatgaaa aaaccaaatg ttcttgtttg     840
gacaattttc gaaatatcgt tatggatttt atttgggctt tccctacttc taagtattat     900
tctcaaggca agtcatgtag ggttaatttt ggctgtttat tatttgggtt atatttcatt     960
agctgtatat gctagaaatg tattttatct attaaaacat ccccttactt tcttactggc    1020
gccattatat ggaattctcc atgtattagc actattacct atacgctttt atgctttact    1080
aactattaaa tctaatggtt ggggaacacg ttaattacag taattttatg tatttttta    1140 ggaggatatt attaagtgaa gattagaaaa gcgattatcc cagcagcggg attaggcaca    1200
```

<210> SEQ ID NO 18
<211> LENGTH: 366
<212> TYPE: PRT
<213> ORGANISM: Bacillus anthracis pXO1

<400> SEQUENCE: 18

```
Met Lys Val Ala Val Val Pro Ser Tyr Asn Glu Ser Ala Ser Ala
 1               5                  10                  15

Ile Val Asn Thr Ile Asn Ser Val Leu Ala Gln Asp Tyr Pro Ile His
                20                  25                  30

Glu Ile Phe Phe Val Asp Asp Gly Ser Lys Asp Lys Ser Ala Tyr Glu
            35                  40                  45

Val Ala Leu Lys Met Arg Glu Glu Leu Leu Arg Thr Gln Arg Glu Ile
 50                  55                  60

Ala Ala Thr Thr Lys Asn Ile Cys Ser Glu Ile Leu Gly Ile Pro Asp
 65                  70                  75                  80

Leu Ile Val His Arg Leu Pro Lys Asn Cys Gly Lys Arg His Ala Gln
                 85                  90                  95

Leu Trp Ala Phe Lys Arg Thr Thr Ala Asp Ala Ile Val Thr Ile Asp
            100                 105                 110

Ser Asp Gly Asp Leu Phe Pro Asn Ala Val Arg Glu Leu Leu Lys Pro
            115                 120                 125

Phe Asn Asp Glu Lys Val Met Ala Thr Thr Gly His Val Asn Ile Arg
130                 135                 140

Asn Arg Asn Asp Asn Leu Leu Thr Lys Leu Ile Asp Met Arg Tyr Asp
145                 150                 155                 160

Asn Ala Phe Arg Val Glu Arg Ala Ala Gln Ser Val Thr Gly Asn Val
                165                 170                 175

Leu Val Cys Ser Gly Pro Leu Ser Cys Tyr Arg Arg Glu Val Ile Thr
            180                 185                 190

Glu Asn Leu Glu His Tyr Gly Ser Gln Met Phe Leu Gly Glu Glu Val
            195                 200                 205

Gln Phe Gly Asp Asp Arg Cys Leu Thr Asn Tyr Ala Ile Leu Lys Gly
210                 215                 220

Lys Thr Val Tyr Gln Ser Thr Ala Arg Cys Ile Thr Asp Ala Pro Thr
225                 230                 235                 240

Thr Leu Lys Gln Phe Leu Lys Gln Gln Leu Arg Trp Asn Lys Ser Phe
                245                 250                 255

Phe Arg Glu Ser Leu Ile Ser Leu Gly Ile Gly Met Lys Lys Pro Asn
            260                 265                 270

Val Leu Val Trp Thr Ile Phe Glu Ile Ser Leu Trp Ile Leu Phe Gly
            275                 280                 285

Leu Ser Leu Leu Leu Ser Ile Ile Leu Lys Ala Ser His Val Gly Leu
290                 295                 300

Ile Leu Ala Val Tyr Tyr Leu Gly Tyr Ile Ser Leu Ala Val Tyr Ala
305                 310                 315                 320

Arg Asn Val Phe Tyr Leu Leu Lys His Pro Leu Thr Phe Leu Leu Ala
                325                 330                 335

Pro Leu Tyr Gly Ile Leu His Val Leu Ala Leu Leu Pro Ile Arg Phe
            340                 345                 350

Tyr Ala Leu Leu Thr Ile Lys Ser Asn Gly Trp Gly Thr Arg
355                 360                 365
```

<210> SEQ ID NO 19
<211> LENGTH: 1680
<212> TYPE: DNA
<213> ORGANISM: Ectocarpus siliculosus virus

<400> SEQUENCE: 19

```
gccatttaca tcttggcgcg atcgttgcaa agtaaaaata atgttttctg tgacggaaac      60
aggggcatga catgcttctc ggcctgaaga aaaacctctt gttcattgcg tatctgttct     120
tcaatgccct tttaacgctt ttgttgcttg gattcgatta cggctacatc atcgtatcga     180
tattcgttgt cggcggacac ttcagagatg tgatcaacgt agcataccaa ttacttcaca     240
tgcacaggat actcaggcgt tgtgccgaca tcccggaaga cgatgccaag atagttattt     300
gttgcttggt tccggtgtac aacgagaagc cttcgatgtt aaagaagaat cttgatgctc     360
tgacgacaca gaagctatcg gaaaacacca agttggtggt gatgcttctc tttgacggac     420
tgaacaacca caacgcagat ctcttcaatg ccgtcgtcga tgccattggc cttgacaccg     480
gatgcggaga agagcaatgg tttccgaatt ggaagagcaa gctgctgaag aagttggtgt     540
acaaaatcgg catatacaat gacacgtcgg tcatcctgtc gtacaaggag aacaattcgg     600
gaaaaaaaga ctctctcatc atcggggaaa acttcatcgt gctcggcatc ccgaggatcg     660
aatctctgga cgtacgacaa gtggatttca tctatcacac ggacggcgac accatttccg     720
acgaaaactg tttgaacgag atggtgaagt ctctcgtgga tgatccagac ctcgacggcg     780
tctctggcct cctgagaaca tacctcaagg acgacgcgac ttgctcggaa agtgcgttcg     840
tagcgatgca agactttcag tacttcttct ccattgttgt ccgtaggatg acggagagca     900
taatgaattc aactacctgc ctcccggggt gctccaacat gatcaggata agcgaaaaga     960
ctcacgctgc gattgaaaaa tacggaaacc ttccggtcaa gaagagcggt ctggtgcaga    1020
cagtcacgcg gatgcaagga accgaccgac gatacaccac gctcttgctg agacagggtt    1080
ccaagctaca gatgaattgg cgtgcgtttg ttcacacgga gccaccgctg aacgcgacgg    1140
cgtttgtgaa tcaacgcaga cgatggtctt caaactcctt cttcaattcc atgatcacgc    1200
tgtactccaa caacatcccg atgtacatca agctatcgaa ccttgtcgac atcgcccgag    1260
tcttcaccac gatctttcgc gtgatatcgt acttgtgctt ttgggtttac gtcaagaatt    1320
tttcccttgt caacatcgtt ttttttctcta tatttatcgc ccttccctac ctctatgcct    1380
tcgcctggat attctgtatc gttccagagt ggaagcagat gatagccggt ttttttttga    1440
acaaaatctt cacgccttt ttatctgtga tcgcggtcac aaagatgttc ttcacttcaa    1500
ccgatttcgc ttggggcagt acgcggttga caccaccgga tgcagcgtct taaactcaac    1560
caacaatcgt ctctattaat aaacctgatt cgtgattttg ggttcgattc tcctgtttcc    1620
tttttttcct ttttttcctt ttttttcctttt tttttcctatt ttcctttttg attttgtttt    1680
```

<210> SEQ ID NO 20
<211> LENGTH: 493
<212> TYPE: PRT
<213> ORGANISM: Ectocarpus siliculosus virus

<400> SEQUENCE: 20

```
Met Leu Leu Gly Leu Lys Lys Asn Leu Leu Phe Ile Ala Tyr Leu Phe
1               5                  10                  15

Phe Asn Ala Leu Leu Thr Leu Leu Leu Gly Phe Asp Tyr Gly Tyr
            20                  25                  30

Ile Ile Val Ser Ile Phe Val Val Gly Gly His Phe Arg Asp Val Ile
        35                  40                  45
```

-continued

```
Asn Val Ala Tyr Gln Leu Leu His Met His Arg Ile Leu Arg Arg Cys
     50                  55                  60

Ala Asp Ile Pro Glu Asp Asp Ala Lys Ile Val Ile Cys Cys Leu Val
65                  70                  75                  80

Pro Val Tyr Asn Glu Lys Pro Ser Met Leu Lys Lys Asn Leu Asp Ala
             85                   90                  95

Leu Thr Thr Gln Lys Leu Ser Glu Asn Thr Lys Leu Val Val Met Leu
            100                  105                 110

Leu Phe Asp Gly Leu Asn Asn His Asn Ala Asp Leu Phe Asn Ala Val
        115                  120                 125

Val Asp Ala Ile Gly Leu Asp Thr Gly Cys Gly Glu Glu Gln Trp Phe
    130                 135                 140

Pro Asn Trp Lys Ser Lys Leu Leu Lys Lys Leu Val Tyr Lys Ile Gly
145                 150                 155                 160

Ile Tyr Asn Asp Thr Ser Val Ile Leu Ser Tyr Lys Glu Asn Asn Ser
                165                 170                 175

Gly Lys Lys Asp Ser Leu Ile Ile Gly Glu Asn Phe Ile Val Leu Gly
            180                 185                 190

Ile Pro Arg Ile Glu Ser Leu Asp Val Arg Gln Val Asp Phe Ile Tyr
        195                 200                 205

His Thr Asp Gly Asp Thr Ile Ser Asp Glu Asn Cys Leu Asn Glu Met
    210                 215                 220

Val Lys Ser Leu Val Asp Asp Pro Asp Leu Asp Gly Val Ser Gly Leu
225                 230                 235                 240

Leu Arg Thr Tyr Leu Lys Asp Asp Ala Thr Cys Ser Glu Ser Ala Phe
                245                 250                 255

Val Ala Met Gln Asp Phe Gln Tyr Phe Ser Ile Val Val Arg Arg
            260                 265                 270

Met Thr Glu Ser Ile Met Asn Ser Thr Thr Cys Leu Pro Gly Cys Ser
        275                 280                 285

Asn Met Ile Arg Ile Ser Glu Lys Thr His Ala Ala Ile Glu Lys Tyr
    290                 295                 300

Gly Asn Leu Pro Val Lys Lys Ser Gly Leu Val Gln Thr Val Thr Arg
305                 310                 315                 320

Met Gln Gly Thr Asp Arg Arg Tyr Thr Thr Leu Leu Arg Gln Gly
                325                 330                 335

Ser Lys Leu Gln Met Asn Trp Arg Ala Phe Val His Thr Glu Pro Pro
            340                 345                 350

Leu Asn Ala Thr Ala Phe Val Asn Gln Arg Arg Trp Ser Ser Asn
        355                 360                 365

Ser Phe Phe Asn Ser Met Ile Thr Leu Tyr Ser Asn Asn Ile Pro Met
    370                 375                 380

Tyr Ile Lys Leu Ser Asn Leu Val Asp Ile Ala Arg Val Phe Thr Thr
385                 390                 395                 400

Ile Phe Arg Val Ile Ser Tyr Leu Cys Phe Trp Val Tyr Val Lys Asn
                405                 410                 415

Phe Ser Leu Val Asn Ile Val Phe Phe Ser Ile Phe Ile Ala Leu Pro
            420                 425                 430

Tyr Leu Tyr Ala Phe Ala Trp Ile Phe Cys Ile Val Pro Glu Trp Lys
        435                 440                 445

Gln Met Ile Ala Gly Phe Phe Leu Asn Lys Ile Phe Thr Pro Phe Leu
    450                 455                 460
```

```
Ser Val Ile Ala Val Thr Lys Met Phe Phe Ser Thr Asp Phe Ala
465                 470                 475                 480

Trp Gly Ser Thr Arg Leu Thr Pro Pro Asp Ala Ala Ser
                485                 490
```